United States Patent
Shah et al.

(10) Patent No.: US 12,364,415 B2
(45) Date of Patent: *Jul. 22, 2025

(54) SYSTEMS AND METHODS RELATING TO AN ANALYTE SENSOR SYSTEM HAVING A BATTERY LOCATED WITHIN A DISPOSABLE BASE

(71) Applicant: DexCom, Inc., San Diego, CA (US)

(72) Inventors: Neel Narayan Shah, Carlsbad, CA (US); John Michael Gray, San Diego, CA (US); Jason Halac, San Diego, CA (US); Carl Erich Hoffmeier, Solana Beach, CA (US); Neal Davis Johnston, Dallas, TX (US); Nicholas Kalfas, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/124,502

(22) Filed: Mar. 21, 2023

(65) Prior Publication Data
US 2023/0218203 A1    Jul. 13, 2023

Related U.S. Application Data

(63) Continuation of application No. 16/403,338, filed on May 3, 2019, now Pat. No. 11,642,048, which is a
(Continued)

(51) Int. Cl.
*A61B 5/00* (2006.01)
*A61B 5/145* (2006.01)
(Continued)

(52) U.S. Cl.
CPC ............ *A61B 5/145* (2013.01); *A61B 5/0002* (2013.01); *A61B 5/0004* (2013.01);
(Continued)

(58) Field of Classification Search
None
See application file for complete search history.

(56) References Cited

U.S. PATENT DOCUMENTS

| 4,992,987 A | 2/1991 | Echols et al. |
| 5,445,609 A | 8/1995 | Lattin et al. |

(Continued)

FOREIGN PATENT DOCUMENTS

| CA | 2806765 A1 | 9/2013 |
| EP | 1682203 B1 | 1/2010 |

(Continued)

OTHER PUBLICATIONS

International Search Report and Written opinion for Application No. PCT/US2019/030719 mailed Sep. 11, 2019, 13 pages.
(Continued)

*Primary Examiner* — Etsub D Berhanu
(74) *Attorney, Agent, or Firm* — Snell & Wilmer LLP

(57) ABSTRACT

An analyte sensor system is provided. The system includes a base configured to attach to a skin of a host. The base includes an analyte sensor configured to generate a sensor signal indicative of an analyte concentration level of the host, a battery, and a first plurality of contacts. The system includes a sensor electronics module configured to releasably couple to the base. The sensor electronics module includes a second plurality of contacts, each configured to make electrical contact with a respective one of the first plurality of contacts, and a wireless transceiver configured to transmit a wireless signal based at least in part on the sensor signal. The system includes a first sealing member configured to provide a seal around the first and second plurality of contacts within a first cavity. Related analyte sensor systems, analyte sensor base assemblies and methods are also provided.

16 Claims, 32 Drawing Sheets

Related U.S. Application Data continuation of application No. 16/403,037, filed on May 3, 2019, now Pat. No. 11,690,537.

(60) Provisional application No. 62/667,348, filed on May 4, 2018.

(51) Int. Cl.
  *H01M 50/543* (2021.01)
  *H04W 12/06* (2021.01)
  *H04W 52/02* (2009.01)
  *A61B 5/1486* (2006.01)
  *A61B 5/1495* (2006.01)

(52) U.S. Cl.
  CPC .......... *A61B 5/0015* (2013.01); *A61B 5/6801* (2013.01); *A61B 5/681* (2013.01); *A61B 5/683* (2013.01); *A61B 5/6831* (2013.01); *H01M 50/543* (2021.01); *H04W 12/06* (2013.01); *H04W 52/02* (2013.01); *H04W 52/0232* (2013.01); *A61B 5/0022* (2013.01); *A61B 5/0031* (2013.01); *A61B 5/14532* (2013.01); *A61B 5/14546* (2013.01); *A61B 5/1486* (2013.01); *A61B 5/1495* (2013.01); *A61B 5/6833* (2013.01); *A61B 2560/0209* (2013.01); *A61B 2560/0214* (2013.01); *A61B 2560/0223* (2013.01); *A61B 2560/0443* (2013.01); *H01M 2220/30* (2013.01)

(56) References Cited

U.S. PATENT DOCUMENTS

| | | |
|---|---|---|
| 5,669,790 A | 9/1997 | Carson et al. |
| 6,001,067 A | 12/1999 | Shults et al. |
| 6,424,847 B1 | 7/2002 | Mastrototaro et al. |
| 6,477,395 B2 | 11/2002 | Schulman et al. |
| 6,484,046 B1 | 11/2002 | Say et al. |
| 6,512,939 B1 | 1/2003 | Colvin et al. |
| 6,565,509 B1 | 5/2003 | Say et al. |
| 6,579,690 B1 | 6/2003 | Bonnecaze et al. |
| 6,749,587 B2 | 6/2004 | Flaherty |
| 7,756,561 B2 | 7/2010 | Reggiardo et al. |
| 7,885,697 B2 | 2/2011 | Brister et al. |
| 7,949,381 B2 | 5/2011 | Brister et al. |
| 8,512,276 B2 | 8/2013 | Talbot et al. |
| 8,929,963 B2 | 1/2015 | Lisogurski |
| 11,690,537 B2 | 7/2023 | Shah et al. |
| 2003/0100821 A1 | 5/2003 | Heller et al. |
| 2004/0122353 A1 | 6/2004 | Shahmirian et al. |
| 2005/0027462 A1 | 2/2005 | Goode, Jr. et al. |
| 2005/0027463 A1 | 2/2005 | Goode, Jr. et al. |
| 2005/0065464 A1 | 3/2005 | Talbot et al. |
| 2006/0020186 A1 | 1/2006 | Brister et al. |
| 2006/0020187 A1 | 1/2006 | Brister et al. |
| 2006/0036142 A1 | 2/2006 | Brister et al. |
| 2007/0027385 A1 | 2/2007 | Brister et al. |
| 2007/0073129 A1 | 3/2007 | Shah et al. |
| 2007/0197890 A1 | 8/2007 | Boock et al. |
| 2007/0212906 A1 | 9/2007 | Clayton et al. |
| 2007/0254593 A1 | 11/2007 | Jollota et al. |
| 2008/0108942 A1 | 5/2008 | Brister et al. |
| 2008/0119703 A1 | 5/2008 | Brister et al. |
| 2008/0139910 A1 | 6/2008 | Mastrototaro et al. |
| 2008/0312512 A1 | 12/2008 | Brukalo et al. |
| 2009/0089999 A1 | 4/2009 | Say et al. |
| 2009/0105636 A1 | 4/2009 | Hayter et al. |
| 2009/0216100 A1 | 8/2009 | Ebner et al. |
| 2010/0168545 A1 | 7/2010 | Kamath et al. |
| 2010/0330935 A1 | 12/2010 | Maggert et al. |
| 2011/0058485 A1 | 3/2011 | Sloan |
| 2011/0181127 A1 | 7/2011 | Safabakhsh |
| 2011/0191044 A1 | 8/2011 | Stafford |
| 2012/0059231 A1 | 3/2012 | Frey et al. |
| 2012/0078071 A1 | 3/2012 | Bohm et al. |
| 2012/0082879 A1 | 4/2012 | Petrie et al. |
| 2013/0103424 A1 | 4/2013 | Brown |
| 2013/0150691 A1 | 6/2013 | Pace et al. |
| 2013/0267811 A1 | 10/2013 | Pryor et al. |
| 2013/0344813 A1 | 12/2013 | Ebner et al. |
| 2014/0066730 A1 | 3/2014 | Roesicke et al. |
| 2014/0121989 A1 | 5/2014 | Kamath et al. |
| 2014/0266776 A1 | 9/2014 | Miller et al. |
| 2014/0273645 A1 | 9/2014 | Glick et al. |
| 2015/0094559 A1 | 4/2015 | Russell |
| 2015/0164392 A1 | 6/2015 | Taub et al. |
| 2015/0289788 A1 | 10/2015 | Simpson et al. |
| 2016/0058375 A1 | 3/2016 | Rothkopf |
| 2016/0058380 A1 | 3/2016 | Lee et al. |
| 2016/0198988 A1 | 7/2016 | Bhavaraju et al. |
| 2017/0020456 A1 | 1/2017 | Pace |
| 2017/0112534 A1 | 4/2017 | Schoonmaker et al. |
| 2017/0181628 A1 | 6/2017 | Burnette et al. |
| 2017/0188910 A1 | 7/2017 | Halac et al. |
| 2017/0188912 A1 | 7/2017 | Halac et al. |
| 2017/0251922 A1 | 9/2017 | Roesicke et al. |
| 2017/0290533 A1 | 10/2017 | Antonio et al. |
| 2018/0027104 A1 | 1/2018 | Mandapaka et al. |
| 2018/0027412 A1 | 1/2018 | Mandapaka et al. |
| 2018/0110078 A1 | 4/2018 | Mandapaka et al. |
| 2018/0116572 A1 | 5/2018 | Simpson et al. |
| 2019/0125224 A1 | 5/2019 | Kamath et al. |
| 2019/0133638 A1 | 5/2019 | Ii et al. |
| 2019/0184093 A1 | 6/2019 | Sjolund et al. |
| 2019/0336048 A1 | 11/2019 | Halac et al. |
| 2019/0336049 A1 | 11/2019 | Shah et al. |
| 2019/0336054 A1 | 11/2019 | Shah et al. |
| 2019/0336055 A1 | 11/2019 | Shah et al. |

FOREIGN PATENT DOCUMENTS

| | | |
|---|---|---|
| EP | 2636372 A1 | 9/2013 |
| EP | 1606758 B1 | 11/2015 |
| EP | 2179754 B1 | 6/2016 |
| GB | 2452158 A | 2/2009 |
| JP | 2008246204 A | 10/2008 |
| JP | 2013184061 A | 9/2013 |
| WO | WO-03026726 A1 | 4/2003 |
| WO | WO-2014162383 A1 | 10/2014 |
| WO | WO-2017070360 A1 | 4/2017 |
| WO | WO-2017127349 A1 | 7/2017 |
| WO | WO-2017187943 A1 | 11/2017 |

OTHER PUBLICATIONS

International Search Report and Written opinion for Application No. PCT/US2019/030745 mailed Sep. 30, 2019, 13 pages.

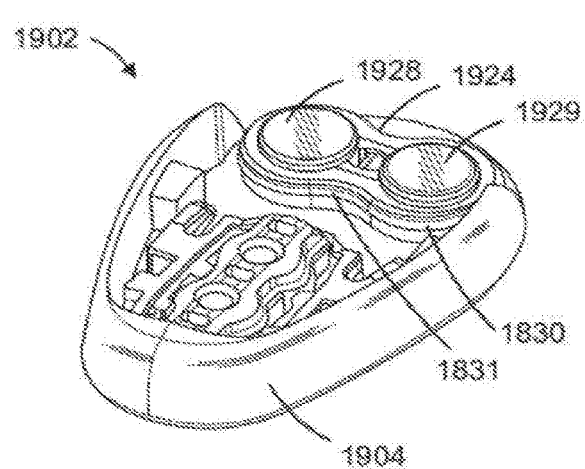
FIG. 19A
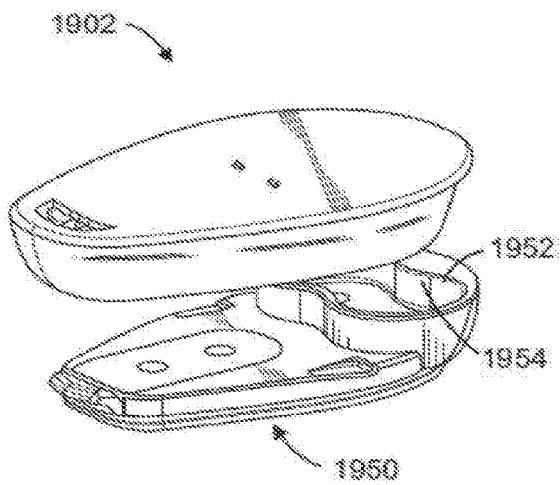
FIG. 19B
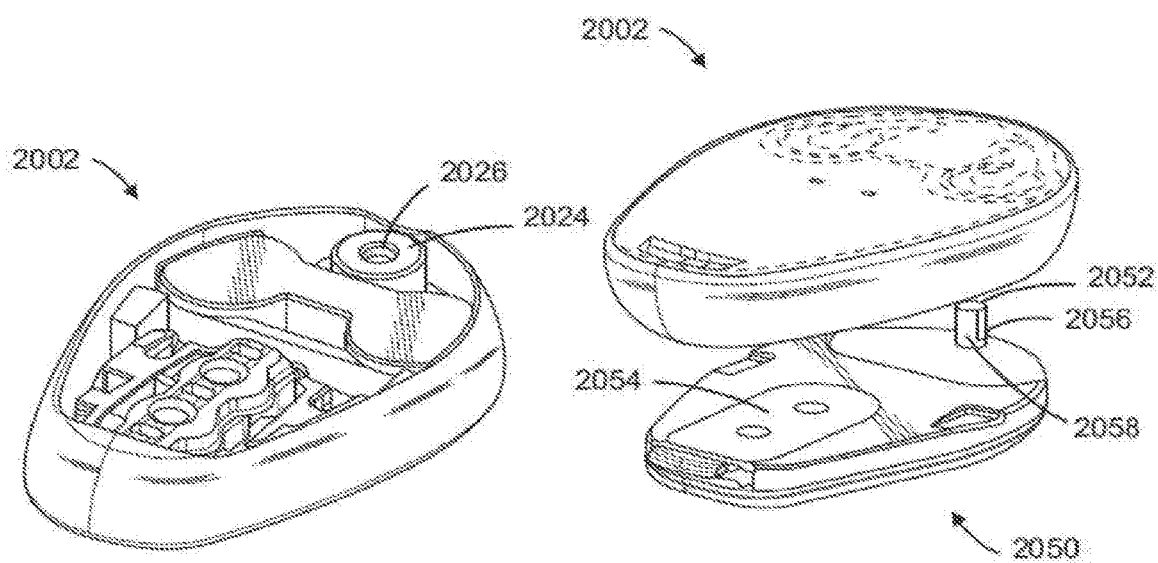
FIG. 20A
FIG. 20B

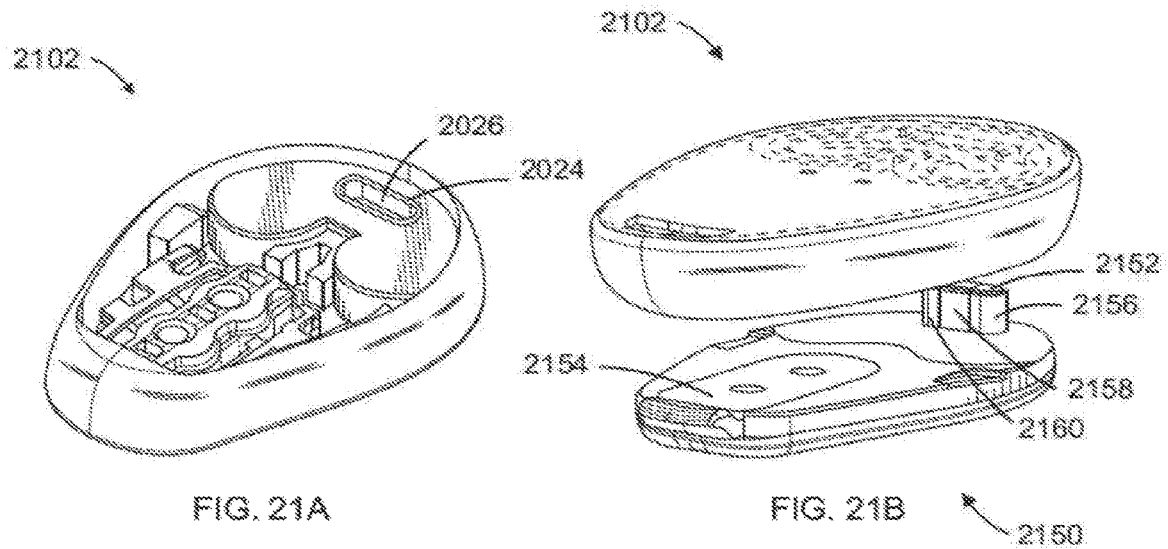
FIG. 21A
FIG. 21B
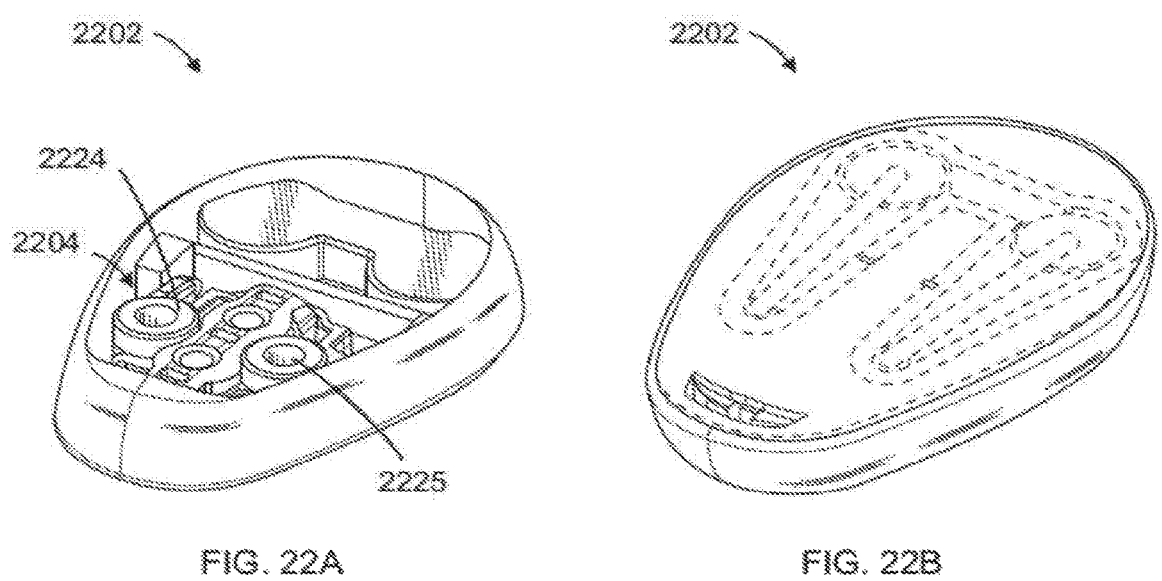
FIG. 22A
FIG. 22B

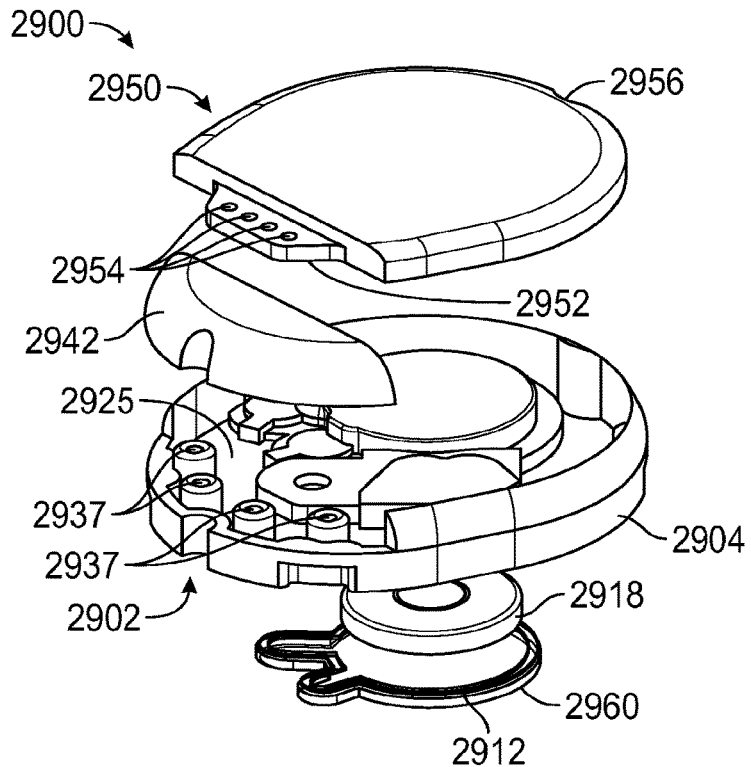
FIG. 29A
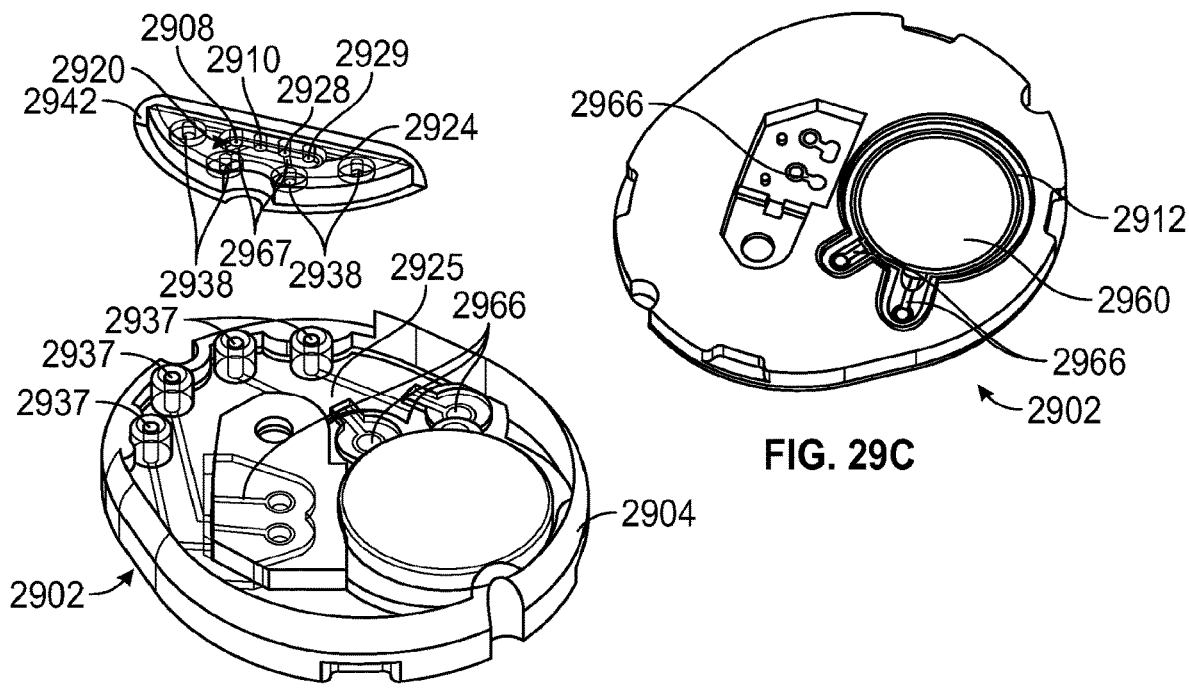
FIG. 29B
FIG. 29C

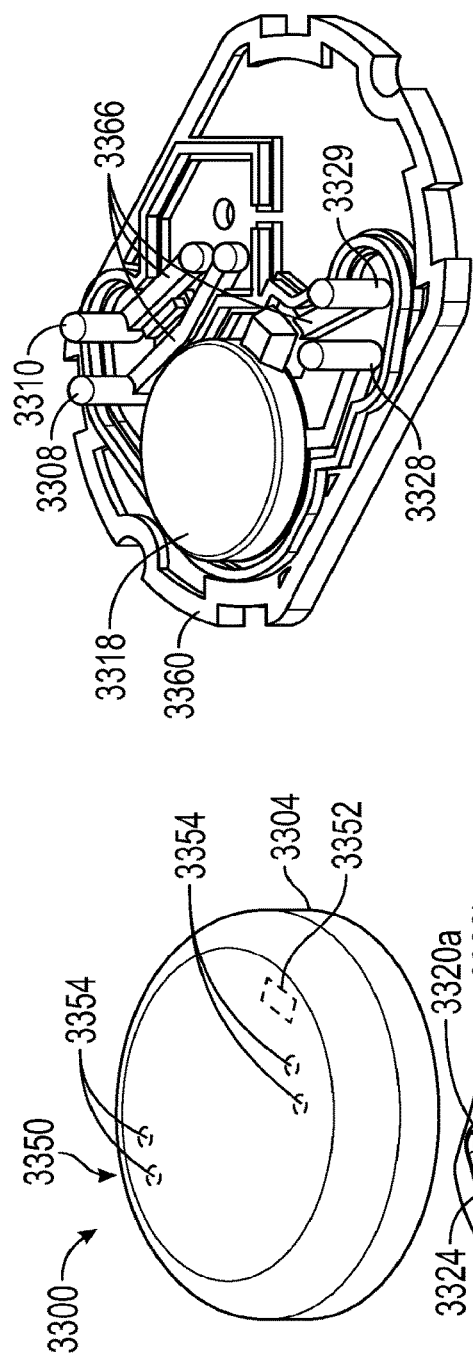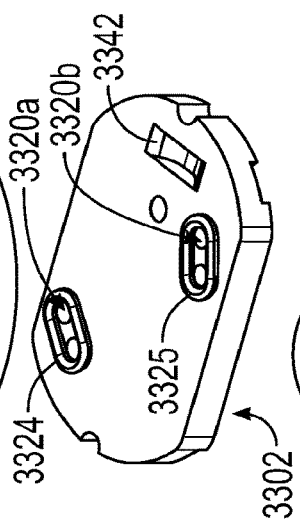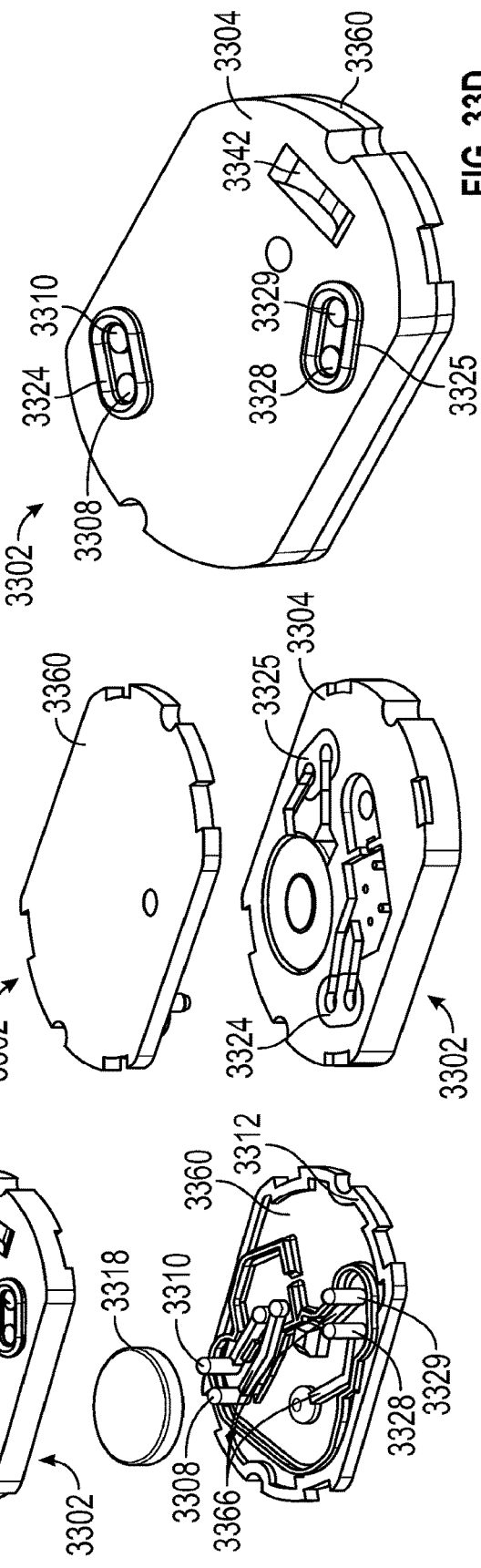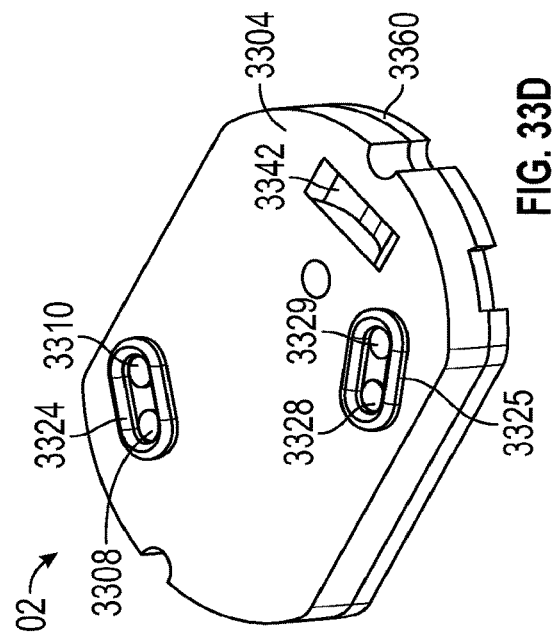

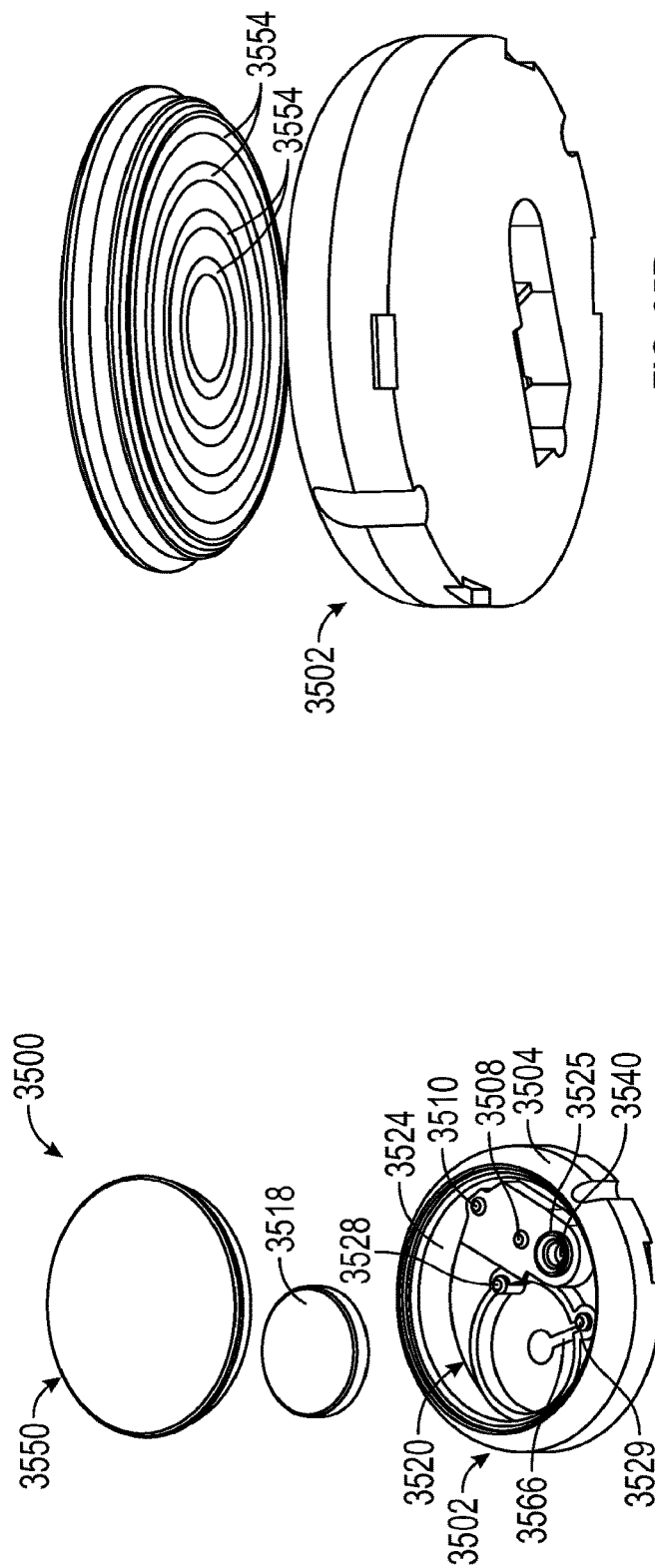
FIG. 35A
FIG. 35B
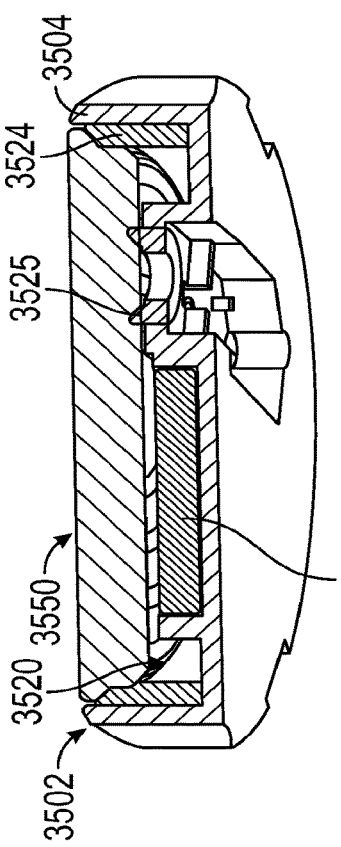
FIG. 35C
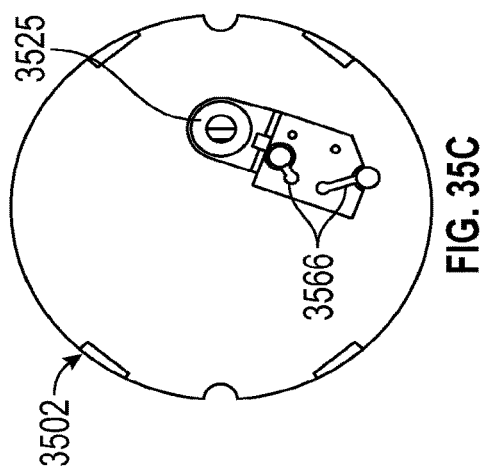
FIG. 35D

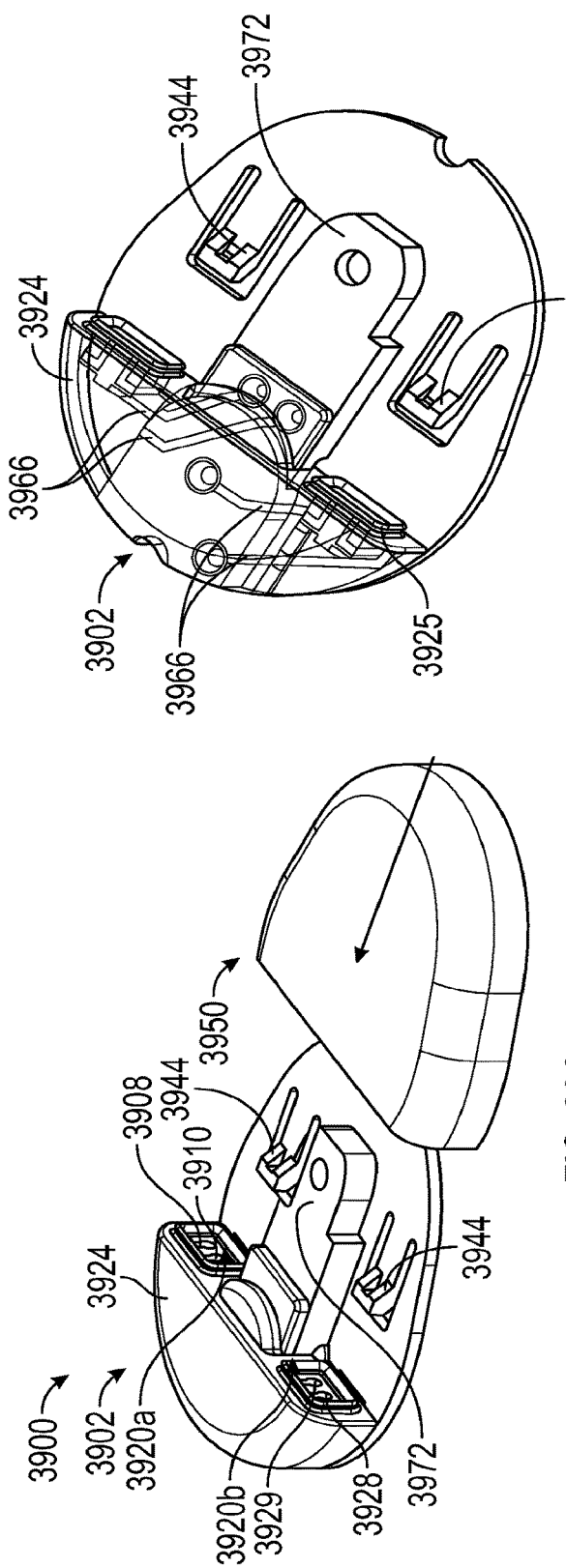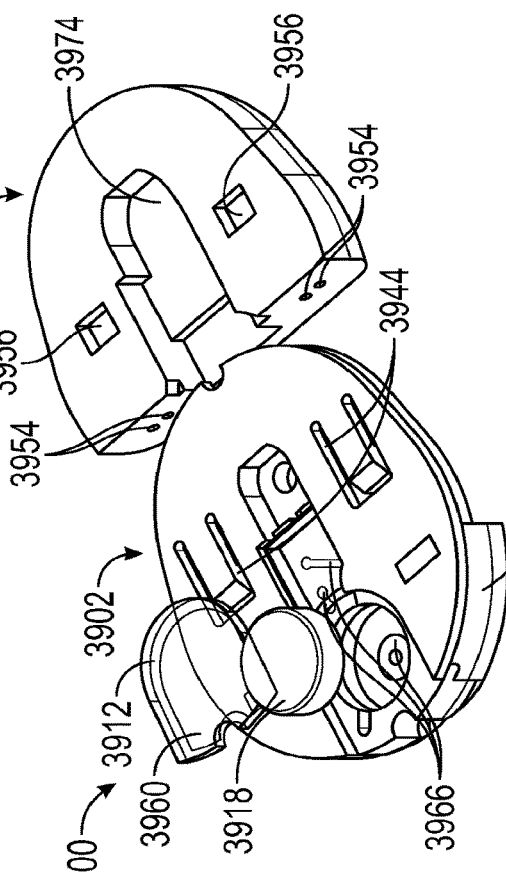

ID
SYSTEMS AND METHODS RELATING TO AN ANALYTE SENSOR SYSTEM HAVING A BATTERY LOCATED WITHIN A DISPOSABLE BASE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/403,338, filed May 3, 2019, which is a continuation of U.S. application Ser. No. 16/403,037, filed May 3, 2019, which claims priority to U.S. Provisional Application No. 62/667,348, filed May 4, 2018. Each of the aforementioned applications are incorporated by reference herein in their entireties, and each is hereby expressly made a part of this specification.

TECHNICAL FIELD

The present development relates generally to medical devices such as analyte sensors, and more particularly, but not by way of limitation, to systems, devices, and methods related to disposable analyte sensor bases having a battery disposed therein and reusable sensor electronics modules configure to releasably couple to the bases.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels. A glucose sensor can provide an estimated glucose concentration level, which can be used as guidance by a patient or caregiver.

Diabetes conditions are sometimes referred to as "Type 1" and "Type 2". A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Blood sugar concentration levels may be monitored with an analyte sensor, such as a continuous glucose monitor. A wearable continuous glucose monitor may be powered by a battery that powers the sensor and other components, such as wireless communication circuitry. It is important that battery power be consistently available to assure that analyte concentration levels can be sensed and communicated by the analyte sensor.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

According to some embodiments, an analyte sensor system is provided. The system includes a base configured to attach to a skin of a host. The base includes an analyte sensor configured to generate a sensor signal indicative of an analyte concentration level of the host, a battery, and a first plurality of contacts. The system includes a sensor electronics module configured to releasably couple to the base. The sensor electronics module includes a second plurality of contacts, each configured to make electrical contact with a respective one of the first plurality of contacts, and a wireless transceiver configured to transmit a wireless signal based at least in part on the sensor signal. The system includes a first sealing member configured to provide a seal around the first and second plurality of contacts within a first cavity.

In some embodiments, the base is disposable. In some embodiments, the sensor electronics module is reusable. In some embodiments, the battery is configured to provide power to the analyte sensor and to the sensor electronics module. In some embodiments, the first plurality of contacts includes a first sensor contact and a second sensor contact, each configured to be electrically coupled to a respective terminal of the analyte sensor. In some embodiments, the second plurality of contacts includes a first signal contact configured to make electrical contact with the first sensor contact and a second signal contact configured to make electrical contact with the second sensor contact.

In some embodiments, the first plurality of contacts further includes a first battery contact and a second battery contact, each configured to be electrically coupled to a respective terminal of the battery. In some embodiments, the second plurality of contacts further includes a first power contact configured to make electrical contact with the first battery contact and a second power contact configured to make electrical contact with the second battery contact. In some embodiments, the first and second signal contacts are configured to receive the sensor signal via the first and second sensor contacts and the first and second power contacts are configured to receive power from the battery.

In some embodiments, the base further includes a first retaining member and a second retaining member, and the sensor electronics module further includes a securement feature configured to mate with the first retaining member and a retention feature configured to mate with the second retaining member, thereby releasably coupling the sensor electronics module to the base. In some embodiments, the second retaining member is frangible and configured to be separable from the base.

In some embodiments, the base further includes a cover configured to secure to the base and configured to secure the battery within the base. In some embodiments, the cover includes a first plurality of conductive traces configured to couple at least some of the first plurality of contacts to one of the analyte sensor and the battery. In some embodiments, the cover includes a recess configured to receive the battery. In some embodiments, the cover includes a weld line configured to secure the cover to the base. In some embodiments, the first sealing member is configured as a portion of the cover. In some embodiments, the cover is configured to be disposed between the base and the sensor electronics module. In some embodiments, the cover is configured to secure to a bottom of the base.

In some embodiments, the base includes a first plurality of conductive traces configured to couple at least some of the first plurality of contacts to one of the analyte sensor and the battery. In some embodiments, the first sealing member extends over the first plurality of conductive traces, thereby sealing the first plurality of conductive traces from moisture ingress. In some embodiments, the first sealing member extends over the battery, thereby sealing the battery from moisture ingress. In some embodiments, at least some of the second plurality of contacts are in direct electrical contact with the analyte sensor or the battery.

In some embodiments, the second plurality of contacts are disposed on the securement feature. In some embodiments, the second plurality of contacts include at least one signal contact configured to electrically connect with the analyte sensor and at least one power contact configured to electrically connect with the battery. In some embodiments, the second plurality of contacts include at least two signal contacts configured to electrically connect with the analyte sensor and at least two power contacts configured to electrically connect with the battery. In some embodiments, the first retaining member includes a hood and the first plurality of contacts are disposed within the hood. In some embodiments, the first sealing member is disposed around a circumference of the securement feature such that the first cavity is disposed within the hood. In some embodiments, the first sealing member is disposed on an inner surface of the hood. In some embodiments, the sensor electronics module is configured to releasably couple to the base by mating the securement feature with the first retaining member while the sensor electronics module is disposed at an elevated angle with respect to the base, and pivoting the sensor electronics module, about the first retaining member, toward the base until the retention feature mates with the second retaining member.

In some embodiments, the sensor electronics module includes an aperture and the base includes a raised portion configured to fit within the aperture, an outer perimeter of the raised portion complimenting an inner perimeter of the aperture. In some embodiments, the first plurality of contacts is disposed on the raised portion. In some embodiments, the aperture is symmetrical about at least one axis parallel to a top surface of the sensor electronics module and asymmetrical about at least one other axis parallel to the top surface of the sensor electronics module. In some embodiments, a top surface of the raised portion sits substantially flush with a top surface of the sensor electronics module. In some embodiments, the sensor electronics module is configured to releasably couple to the base by fitting the raised portion of the base within the aperture of the sensor electronics module and pressing the sensor electronics module against the base in a direction substantially perpendicular to a bottom surface of the base until the one or more retention features of the sensor electronics module couple with one or more corresponding retaining members of the base. In some embodiments, the base includes a recess disposed in a top surface of the base and the sensor electronics module includes a protrusion configured to mate with the recess, thereby aligning the sensor electronics module with the base.

In some embodiments, the base further includes a third plurality of contacts, the sensor electronics module further includes a fourth plurality of contacts, each configured to make electrical contact with a respective one of the third plurality of contacts, and the system further includes a second sealing member configured to provide a continuous seal around the third and fourth plurality of contacts within a second cavity. In some embodiments, the third plurality of contacts includes a first battery contact and a second battery contact, each configured to be electrically coupled to a respective terminal of the battery. In some embodiments, the fourth plurality of contacts includes a first power contact configured to make electrical contact with the first battery contact and a second power contact configured to make electrical contact with the second battery contact. In some embodiments, the second plurality of contacts include concentric, circular contacts. In some embodiments, the concentric, circular contacts are disposed around a center of the sensor electronics module. In some embodiments, each of the second plurality of contacts are configured to make electrical contact with the respective one of the first plurality of contacts when the sensor electronics module is secured to the base in any of a plurality of radial orientations.

In some embodiments, the base includes an aperture and the sensor electronics module includes a raised portion configured to fit within the aperture, an outer perimeter of the raised portion complimenting an inner perimeter of the aperture. In some embodiments, the aperture and the raised portion each have a substantially circular shape. In some embodiments, the sensor electronics module is configured to releasably couple to the base by fitting the raised portion of the sensor electronics module within the aperture of the base and pressing the sensor electronics module against the base in a direction substantially perpendicular to a bottom surface of the base until the one or more retention features of the sensor electronics module couple with one or more corresponding retaining members of the base.

In some embodiments, the base includes a raised rail and the sensor electronics module includes a channel having a shape that compliments a shape of the raised rail. In some embodiments, the raised rail has a constant width along a length of the raised rail. In some embodiments, a width of the raised rail tapers along a length of the raised rail. In some embodiments, the first plurality of contacts is disposed on a sidewall of the raised rail and the second plurality of contacts is disposed on a sidewall of the channel. In some embodiments, the first and third plurality of contacts are disposed on a sidewall of the base and the second and fourth plurality of contacts are disposed on a sidewall of the sensor electronics module. In some embodiments, the sensor electronics module is configured to releasably couple to the base by aligning the channel of the sensor electronics module with the raised rail of the base, and sliding the sensor electronics module, along the raised rail, in a direction parallel to the host's body until the sensor electronics module is seated against the base, and one or more retention features of the sensor electronics module couple with one or more corresponding retaining members of the base.

According to some embodiments, an analyte sensor system is provided. The system includes a base configured to attach to a skin of a host. The base includes an analyte sensor configured to generate a sensor signal indicative of an analyte concentration level of the host, a battery, and a first plurality of contacts. The system includes a sensor electronics module configured to releasably couple to the base. The sensor electronics module includes a second plurality of contacts, each configured to make electrical contact with a respective one of the first plurality of contacts when the sensor electronics module is secured to the base in any of a plurality of radial orientations, and a wireless transceiver configured to transmit a wireless signal based at least in part on the sensor signal.

In some embodiments, the second plurality of contacts are concentric and annularly spaced apart from one another. In some embodiments, a respective one of the second plurality of contacts is configured to make electrical contact with the respective one of the first plurality of contacts at any point along the respective one of the second plurality of contacts. In some embodiments, the second plurality of contacts are formed by laser direct structuring. In some embodiments, the system further comprises a first sealing member configured to provide a seal around the first and second plurality of contacts within a first cavity.

In some embodiments, the base is disposable. In some embodiments, the sensor electronics module is reusable. In some embodiments, the battery is configured to provide power to the analyte sensor and to the sensor electronics module. In some embodiments, the first plurality of contacts comprises a first sensor contact and a second sensor contact, each configured to be electrically coupled to a respective terminal of the analyte sensor. In some embodiments, the second plurality of contacts comprises a first signal contact configured to make electrical contact with the first sensor contact and a second signal contact configured to make electrical contact with the second sensor contact. In some embodiments, the first plurality of contacts further comprises a first battery contact and a second battery contact, each configured to be electrically coupled to a respective terminal of the battery.

According to some embodiments, an analyte sensor base assembly is provided. The assembly includes a base configured to attach to a skin of a host. The assembly includes an analyte sensor configured to generate a sensor signal indicative of an analyte concentration level of the host. The assembly includes at least one battery. The assembly includes at least one sensor contact. The assembly includes at least one battery contact. The assembly includes a sealing member configured to provide a seal around at least the at least one battery contact.

In some embodiments, the sealing member is further configured to provide the seal around at least the at least one sensor contact. In some embodiments, the assembly includes at least two sensor contacts and at least two battery contacts, wherein the sealing member is configured to provide the seal around the at least two sensor contacts and the at least two battery contacts. In some embodiments, the base further includes a plurality of conductive traces configured to electrically connect the battery to the at least one battery contact. In some embodiments, the base further includes a plurality of conductive traces configured to electrically connect the analyte sensor to the at least one sensor contact. In some embodiments, the assembly is disposable. In some embodiments, the battery is configured to provide power to the analyte sensor and to a sensor electronics module that is couplable to the base.

In some embodiments, the base further includes a first retaining member configured to mate with a securement feature of a couplable sensor electronics module, and a second retaining member configured to mate with a retention feature of the couplable sensor electronics module. In some embodiments, the second retaining member is frangible and configured to be separable from the base. In some embodiments, the base further includes a cover configured to secure to the base and configured to secure the battery within the base. In some embodiments, the first retaining member includes a hood and the at least one sensor contact and the at least one battery contact are disposed within the hood. In some embodiments, the sealing member is disposed within the hood.

According to some embodiments, an analyte monitoring system is provided. The system may include a base configured to connect to a host, a reusable portion, and a battery assembly. The base may include an analyte sensor configured to detect a sensor signal indicative of an analyte concentration level of the host. The reusable portion may be configured to couple to the base may include a wireless transceiver, wherein the reusable portion receives a signal from the base and transmits a wireless signal based at least in part on the sensor signal. The battery assembly may include a battery housing and one or more batteries. The battery assembly may be configured to mechanically couple with the base or the reusable portion and electrically couple with the base or the reusable portion, wherein the batteries deliver power to the analyte sensor and the wireless transceiver.

According to some embodiments, an analyte monitoring kit is provided. The kit may include a sensor electronics package including a processor and a communication circuit, and a plurality of sensor devices, each sensor device including a sensor device battery and a sensor configured to generate a signal indicative of an analyte concentration level of a host, wherein the sensor electronics package is configured to electrically and mechanically couple with each of the plurality of sensor devices and draw power from the sensor device battery to power the processor and the communication circuit, wherein the sensor electronics package is reusable with the plurality of sensor devices.

According to some embodiments, a biosensor device is provided. The device may include an analyte sensor configured to generate a signal a sensor signal representative of a concentration level of a substance in a fluid of a host, a processor configured to receive the sensor signal and determine a value based on the sensor signal, a communication circuit operatively coupled to the processor and configured to transmit the value based on the sensor signal, a battery, and a supercapacitor electrically coupled to the battery, wherein the battery and the supercapacitor are configured to deliver power to the processor or the communication circuit, the supercapacitor reducing a load on the battery to reduce strain on the battery during a high-load period.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

The present embodiments now will be discussed in detail with an emphasis on highlighting the advantageous features. These embodiments are for illustrative purposes only and are not to scale, instead emphasizing the principles of the disclosure. These drawings include the following figures, in which like numerals may indicate like parts:

FIG. 19A is a perspective top view of an example sensor base, according to some embodiments;

FIG. 19B is a perspective bottom view of the base shown in FIG. 19A and an example sensor electronics module configured to mechanically and electrically couple with the base shown in FIGS. 19A and 19B;

FIG. 20A is a perspective top view of an example sensor base, according to some embodiments;

FIG. 20B is a perspective bottom view of the base shown in FIG. 20A and an example sensor electronics module configured to mechanically and electrically couple with the base shown in FIGS. 20A and 20B;

FIG. 21A is a perspective top view of an example sensor base, according to some embodiments;

FIG. 21B is a perspective bottom view of the base shown in FIG. 21A and an example sensor electronics module configured to mechanically and electrically couple with the base shown in FIGS. 21A and 21B;

FIG. 22A is a perspective top view of an example sensor base, according to some embodiments;

FIG. 22B is a perspective bottom view of the base shown in FIG. 22A;

FIG. 29A is an exploded perspective view of an example base and a sensor electronics module configured to be secured within the base, according to some embodiments;

FIG. 29B is a perspective view of portions of the base of FIG. 29A;

FIG. 29C is a perspective view of a bottom of the base of FIG. 29A;

FIG. 33A is an exploded perspective view of an example base and a sensor electronics module configured to be secured over or on the base, according to some embodiments;

FIG. 33B is a perspective view of a battery disposed on a cover of the base of FIG. 33A;

FIG. 33C is an exploded perspective bottom view of the cover and the base of FIG. 33B;

FIG. 33D is a perspective bottom view of the cover secured to the base of FIG. 33B;

FIG. 35A is an exploded perspective view of an example base and a sensor electronics module configured to be secured over or on the base, according to some embodiments;

FIG. 35B is an exploded perspective bottom view of the base and the sensor electronics module of FIG. 35A;

FIG. 35C is a plan view of a bottom of the base of FIG. 35A;

FIG. 35D is a perspective cutaway view of the sensor electronics module secured to the base of FIG. 35A;

FIG. 39A is a perspective view of an example base and a sensor electronics module configured to be slid over and secured to the base, according to some embodiments;

FIG. 39B is another perspective view of the base of FIG. 39A;

FIG. 39C is an exploded perspective bottom view of the base and the sensor electronics module of FIG. 39A.

DETAILED DESCRIPTION

Figure 1:
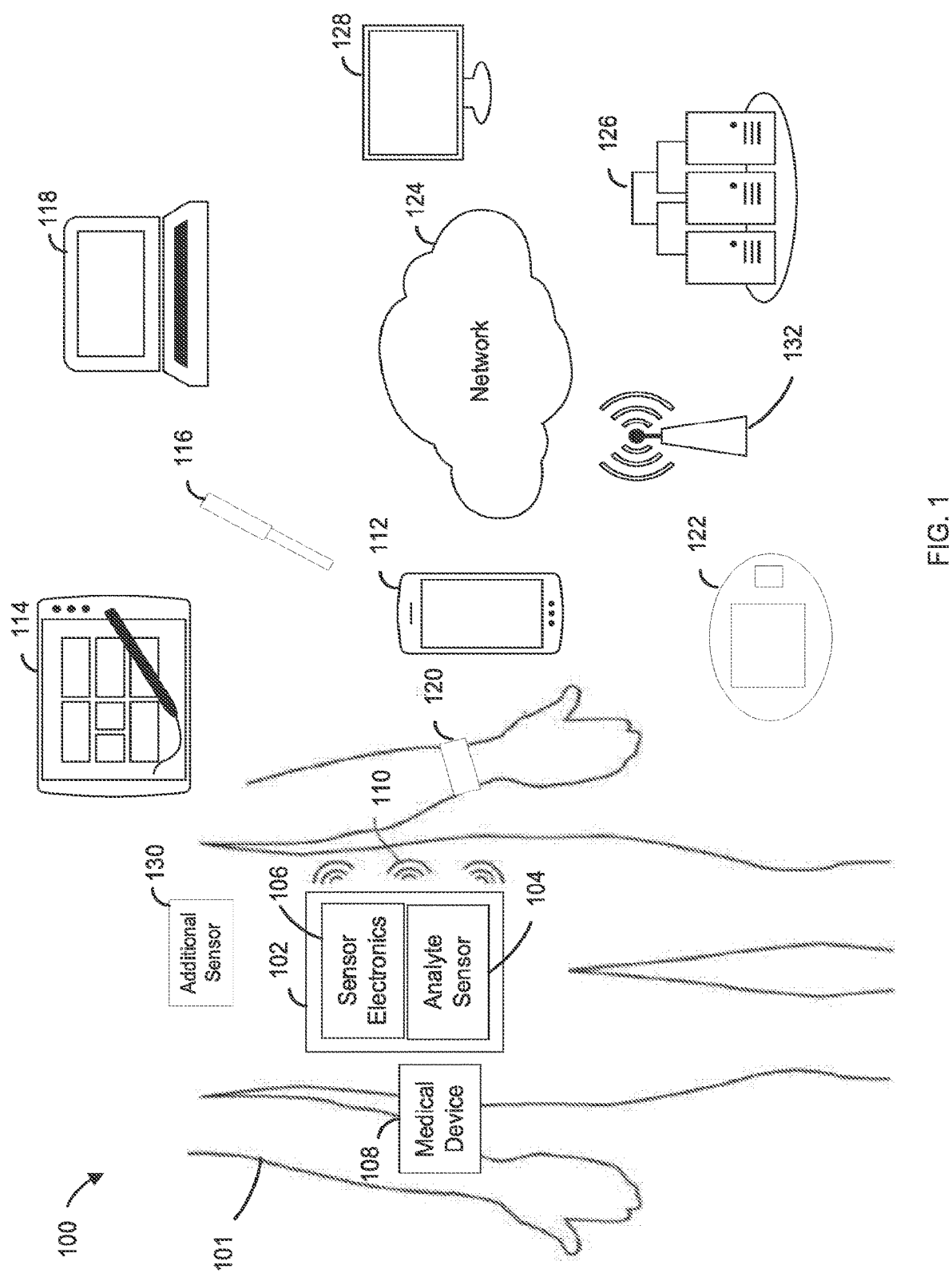
FIG. 1 is an illustration of an example medical device system, according to some embodiments.

The following description and examples illustrate some exemplary implementations, embodiments, and arrangements in detail. Those of skill in the art will recognize that there are numerous variations and modifications of this disclosure that are encompassed by its scope. Accordingly, the description of a certain example embodiment should not be deemed to limit the scope of the present disclosure.

Definitions

In order to facilitate an understanding of the various embodiments described herein, a number of terms are defined below.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; D-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The terms "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The term "calibration" as used herein is a broad term and is to be given its ordinary and customary meaning to a person of ordinary skill in the art (and is not to be limited to a special or customized meaning), and furthermore refers without limitation to the process of determining the relationship between the sensor data and the corresponding reference data, which can be used to convert sensor data into meaningful values substantially equivalent to the reference data, with or without utilizing reference data in real time. In some embodiments, namely, in analyte sensors, calibration can be updated or recalibrated (at the factory, in real time and/or retrospectively) over time as changes in the relationship between the sensor data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, including by use of a sensitivity, to provide a meaningful value to a user.

The term "algorithm" as used herein is a broad term and is to be given its ordinary and customary meaning to a person of ordinary skill in the art (and is not to be limited to a special or customized meaning), and furthermore refers without limitation to a computational process (for example, programs) involved in transforming information from one state to another, for example, by using computer processing.

The term "sensor" as used herein is a broad term and is to be given its ordinary and customary meaning to a person of ordinary skill in the art (and is not to be limited to a special or customized meaning), and furthermore refers without limitation to the component or region of a device by which an analyte can be quantified. A "lot" of sensors generally refers to a group of sensors that are manufactured on or around the same day and using the same processes and tools/materials. Additionally, sensors that measure temperature, pressure etc. may be referred to as a "sensor".

The terms "glucose sensor" and "member for determining the amount of glucose in a biological sample" as used herein are broad terms and are to be given their ordinary and customary meaning to a person of ordinary skill in the art (and are not to be limited to a special or customized meaning), and furthermore refer without limitation to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, calculating, deriving, establishing and/or the like. Determining may also include ascertaining that a parameter matches a predetermined criterion, including that a threshold has been met, passed, exceeded, and so on.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammals, particularly humans.

The term "continuous analyte (or glucose) sensor" as used herein is a broad term and is to be given its ordinary and customary meaning to a person of ordinary skill in the art (and is not to be limited to a special or customized meaning), and furthermore refers without limitation to a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "sensing membrane" as used herein is a broad term and is to be given its ordinary and customary meaning to a person of ordinary skill in the art (and is not to be limited to a special or customized meaning), and furthermore refers without limitation to a permeable or semi-permeable membrane that can be comprised of two or more domains and is typically constructed of materials of a few microns thickness or more, which are permeable to oxygen and may or may not be permeable to glucose. In one example, the sensing membrane comprises an immobilized glucose oxidase enzyme, which enables an electrochemical reaction to occur to measure a concentration of glucose.

The term "sensor data," as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signals directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The terms broadly encompass a plurality of time spaced data points from a sensor, such as from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "sensor electronics," as used herein, is a broad term, and is to be given its ordinary and customary meaning to a person of ordinary skill in the art (and is not to be limited to a special or customized meaning) and refers without limitation to the components (for example, hardware and/or software) of a device configured to process data. As described in further detail hereinafter (see, e.g., FIG. 2) "sensor electronics" may be arranged and configured to measure, convert, store, transmit, communicate, and/or retrieve sensor data associated with an analyte sensor.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (e.g., $H_2O_2$) associated with the measured analyte (e.g., glucose). For example, in one embodiment, a sensor has a sensitivity from about 1 to about 300 picoamps of current for every 1 mg/dL of glucose analyte.

The term "sample," as used herein, is a broad term, and is to be given its ordinary and customary meaning to a person of ordinary skill in the art (and it is not to be limited to a special or customized meaning), and refers without limitation to a sample of a host body, for example, body fluids, including, blood, serum, plasma, interstitial fluid, cerebral spinal fluid, lymph fluid, ocular fluid, saliva, oral fluid, urine, excretions, or exudates.

The term "distal to," as used herein, is a broad term, and is to be given its ordinary and customary meaning to a person of ordinary skill in the art (and is not to be limited to a special or customized meaning) and refers without limitation to the spatial relationship between various elements in comparison to a particular point of reference. In general, the term indicates an element is located relatively far from the reference point than another element.

The term "proximal to," as used herein, is a broad term, and is to be given its ordinary and customary meaning to a person of ordinary skill in the art (and is not to be limited to a special or customized meaning) and refers without limitation to the spatial relationship between various elements in comparison to a particular point of reference. In general, the term indicates an element is located relatively near to the reference point than another element.

The terms "electrical connection" and "electrical contact," as used herein, are broad terms, and are to be given their ordinary and customary meaning to a person of ordinary skill in the art (and are not to be limited to a special or customized meaning), and refer without limitation to any connection between two electrical conductors known to those in the art. In one embodiment, electrodes are in electrical connection with (e.g., electrically connected to) the electronic circuitry of a device. In another embodiment, two materials, such as but not limited to two metals, can be in electrical contact with each other, such that an electrical current can pass from one of the two materials to the other material and/or an electrical potential can be applied.

The term "elongated conductive body," as used herein, is a broad term, and is to be given its ordinary and customary meaning to a person of ordinary skill in the art (and is not to be limited to a special or customized meaning), and refers without limitation to an elongated body formed at least in part of a conductive material and includes any number of coatings that may be formed thereon. By way of example, an "elongated conductive body" may mean a bare elongated conductive core (e.g., a metal wire), an elongated conductive core coated with one, two, three, four, five, or more layers of material, each of which may or may not be conductive, or an elongated non-conductive core with conductive coatings, traces, and/or electrodes thereon and coated with one, two, three, four, five, or more layers of material, each of which may or may not be conductive.

The term "ex vivo portion," as used herein, is a broad term, and is to be given its ordinary and customary meaning to a person of ordinary skill in the art (and is not to be limited to a special or customized meaning), and refers without limitation to a portion of a device (for example, a sensor) adapted to remain and/or exist outside of a living body of a host.

The term "in vivo portion," as used herein, is a broad term, and is to be given its ordinary and customary meaning to a person of ordinary skill in the art (and is not to be limited to a special or customized meaning), and refers without limitation to a portion of a device (for example, a sensor) adapted for insertion into and/or existence within a living body of a host.

The term "potentiostat," as used herein, is a broad term, and is to be given its ordinary and customary meaning to a person of ordinary skill in the art (and is not to be limited to a special or customized meaning) and refers without limitation to an electronic instrument that controls the electrical potential between the working and reference electrodes at one or more preset values.

The term "processor module," as used herein, is a broad term, and is to be given its ordinary and customary meaning to a person of ordinary skill in the art (and are not to be limited to a special or customized meaning), and refers without limitation to a computer system, state machine, processor, components thereof, and the like designed to perform arithmetic or logic operations using logic circuitry that responds to and processes the basic instructions that drive a computer.

The term "sensor session," as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of (e.g., disconnection from) system electronics).

The terms "substantial" and "substantially," as used herein, are broad terms, and are to be given their ordinary and customary meaning to a person of ordinary skill in the art (and are not to be limited to a special or customized meaning) and refer without limitation to a sufficient amount that provides a desired function.

"Coaxial two conductor wire-based sensor": A round wire sensor consisting of a conductive center core, an insulating middle layer and a conductive outer layer with the conductive layers exposed at one end for electrical contact.

"Pre-connected sensor": A sensor that has a "sensor interconnect/interposer/sensor carrier" attached to it. Therefore this "Pre-connected sensor" comprises two parts that are joined: the sensor itself, and the interconnect/interposer/sensor carrier. The term "pre-connected sensor" unit refers to the unit that is formed by the permanent union of these two distinct parts.

Other definitions will be provided within the description below, and in some cases from the context of the term's usage.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade) ° F. (degrees Fahrenheit), Pa (Pascals), kPa (kiloPascals), MPa (megaPascals), GPa (gigaPascals), Psi (pounds per square inch), kPsi (kilopounds per square inch).

Overview

Energy in an analyte sensor system may be managed by controlling energy output, such as the consumption of energy by communication circuits or other circuits, and by controlling energy inputs, such as replacing or recharging batteries. Wearable analyte sensor systems may include a battery, capacitor, or other power storage component, that powers a sensor, processor, communication circuit, or other electrical components. Management of energy consumption (e.g. power management, i.e. management of energy expended per unit of time) can be important to extend the life of sensor components (e.g., a battery) and to assure that the analyte sensor continues to perform its intended function(s). For example, where a component (e.g., a sensor electronics module, which may include relatively costly wireless sensor electronics package components) has a battery that is not rechargeable or replaceable, the life of the component may be extended by managing the use of energy stored in the battery.

Sensor systems may apply algorithms that take into account one or more of a variety of real-time, systemic, trend, model, or other factors such as wireless performance, analyte management (e.g., glucose management), battery state, power management trends or characteristic, patient or environmental risk factors, risk tolerance, location, or a combination thereof. For example, a system may take an action responsive to a condition. A system response may include changing system behavior to decrease power consumption or increase power consumption based on the determined condition. For example, an analyte management condition (e.g., estimated glucose level in range or below or above a specified value or exhibiting a specified trend) may be used as an input to determine system behavior and energy consumption. In various examples, a condition may be predetermined and programmed or hard-wired into a device, or specified by a user, or determined by a processor (e.g., based upon information learned from data.)

In some examples, a sensor system may receive an operational parameter that relates to a peripheral device, which may be a therapy device such as an insulin pump or pen. The sensor system may receive the operational parameter from the peripheral device, or from a remote resource based on an identification of the peripheral device (e.g., pump model number or serial number), or from a memory (e.g., retrieved from a lookup table.) The sensor system may manage its operations based at least in part on the operational parameter. For example, based on the operational parameter, a system may communicate according to a schedule, or with a specified device or group of devices, or manage power consumption to extend a battery.

System hardware may be configured to enable replacement of batteries, and system components (e.g., sensor base and sensor electronics) may be configured to provide a water-tight seal after replacement of batteries. Battery-supporting technologies such as supercapacitors may also be used to facilitate energy management.

Example System

FIG. 1 is an illustration of an example system 100. The system 100 may include an analyte sensor system 102 that may be coupled to a host 101. The host 101 may be a human patient. The patient may, for example, be subject to a temporary or permanent diabetes condition or other health condition for which analyte monitoring may be useful.

The analyte sensor system 102 may include an analyte sensor 104, which may for example be a glucose sensor. The glucose sensor may be any device capable of measuring the concentration of glucose. For example, the analyte sensor 104 may be fully implantable, or the analyte sensor may be wearable on the body (e.g., on the body but not under the skin), or the analyte sensor may be a transcutaneous device (e.g., with a sensor residing under or in the skin of a host). It should be understood that the devices and methods described herein can be applied to any device capable of detecting a concentration of glucose and providing an output signal that represents the concentration of glucose (e.g., as a form of analyte data).

The analyte sensor system 102 may also include sensor electronics 106. In some examples, the analyte sensor 104 and sensor electronics 106 may be provided as an integrated package. In other examples, the analyte sensor 104 and sensor electronics 106 may be provided as separate components or modules. For example, the analyte sensor system 102 may include a disposable (e.g., single-use) base that may include the analyte sensor 104, a component for attaching the sensor to a host (e.g., an adhesive pad), or a mounting structure configured to receive another component. The system may also include a sensor electronics package, which may include some or all of the sensor electronics 106 shown in FIG. 2. The sensor electronics package may be reusable.

An analyte sensor may use any known method, including invasive, minimally-invasive, or non-invasive sensing techniques (e.g., optically excited fluorescence, microneedle, transdermal monitoring of glucose), to provide a data stream indicative of the concentration of the analyte in a host. The data stream may be a raw data signal, which may be converted into a calibrated and/or filtered data stream that is used to provide a useful value of the analyte (e.g., estimated blood glucose concentration level) to a user, such as a patient or a caretaker (e.g., a parent, a relative, a guardian, a teacher, a doctor, a nurse, or any other individual that has an interest in the wellbeing of the host).

Analyte sensor 104 may, for example, be a continuous glucose sensor, which may, for example, include a subcutaneous, transdermal (e.g., transcutaneous), or intravascular device. In some embodiments, such a sensor or device may recurrently (e.g., periodically or intermittently) analyze sensor data. The glucose sensor may use any method of glucose-measurement, including enzymatic, chemical, physical, electrochemical, spectrophotometric, polarimetric, calorimetric, iontophoretic, radiometric, immunochemical, and the like. In various examples, the analyte sensor system 102 may be or include a continuous glucose monitor sensor available from DexCom™ (e.g., the DexCom G5™ sensor or Dexcom G6™ sensor or any variation thereof.)

In some examples, analyte sensor 104 may be an implantable glucose sensor, such as described with reference to U.S. Pat. No. 6,001,067 and U.S. Patent Publication No. US-2005-0027463-A1. In some examples, analyte sensor 104 may be a transcutaneous glucose sensor, such as described with reference to U.S. Patent Publication No. US-2006-0020187-A1. In some examples, analyte sensor 104 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In some examples, the continuous glucose sensor may include a transcutaneous sensor such as described in U.S. Pat. No. 6,565,509 to Say et al., for example. In some examples, analyte sensor 104 may be a continuous glucose sensor that includes a subcutaneous sensor such as described with reference to U.S. Pat. No. 6,579,690 to Bonnecaze et al. or U.S. Pat. No. 6,484,046 to Say et al., for example. In some examples, the continuous glucose sensor may include a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

The system 100 may also include a second medical device 108, which may, for example, be a drug delivery device (e.g., insulin pump or insulin pen). In some examples, the medical device 108 may be or include a sensor, such as another analyte sensor, a heart rate sensor, a respiration sensor, a motion sensor (e.g. accelerometer), posture sensor (e.g. 3-axis accelerometer), acoustic sensor (e.g. to capture ambient sound or sounds inside the body). In some examples, medical device 108 may be wearable, e.g. on a watch, glasses, contact lens, patch, wristband, ankle band, or other wearable item, or may be incorporated into a handheld device (e.g., a smartphone). In some examples, the medical device 108 may include a multi-sensor patch that may, for example, detect one or more of an analyte level (e.g. glucose, lactate, insulin or other substance), heart rate, respiration (e.g., using impedance), activity (e.g. using an accelerometer), posture (e.g. using an accelerometer), galvanic skin response, tissue fluid levels (e.g. using impedance or pressure).

The analyte sensor system 102 may communicate with the second medical device 108 via a wired connection, or via a wireless communication signal 110. For example, the analyte sensor system may be configured to communicate using via radio frequency (e.g. Bluetooth, Medical Implant Communication System (MICS), WiFi, NFC, RFID, Zigbee, Z-Wave or other communication protocols), optically (e.g. infrared), sonically (e.g. ultrasonic), or a cellular protocol (e.g., CDMA (Code Division Multiple Access) or GSM (Global System for Mobiles), or wired connection (e.g. serial, parallel, etc.). In some examples, an array or network of sensors may be associated with the patient. For example, the analyte sensor system 102, medical device 108, and an additional sensor 130 may communicate with one another via wired or wireless (e.g., Bluetooth, MICS, or any of the other options discussed above,) communication. The additional sensor 130 may be any of the examples discussed above with respect to medical device 108. The analyte sensor system 102, medical device 108, and additional sensor 130 on the host 101 are provided for the purpose of illustration and discussion and are not necessarily drawn to scale.

The system may also include one or more peripheral devices, such as a hand-held smart device (e.g., smartphone) 112, tablet 114, smart pen 116 (e.g., insulin delivery pen with processing and communication capability), computer 118, watch 120, or peripheral medical device 122, any of which may communicate with the analyte sensor system 102 via a wireless communication signal, and may also communicate over a network 124 with a server system (e.g., remote data center) 126 or with a remote terminal 128 to facilitate communication with a remote user (not shown) such as a technical support staff member or a clinician.

The system 100 may also include a wireless access point (WAP) 132 that may be used to communicatively couple one or more of analyte sensor system 102, network 124, server system 126, medical device 108 or any of the peripheral devices described above. For example, WAP 132 may provide Wi-Fi and/or cellular connectivity within system 100. Other communication protocols (e.g., Near Field Communication (NFC) or Bluetooth) may also be used among devices of the system 100. In some examples, the server system 126 may be used to collect analyte data from analyte sensor system 102 and/or the plurality of other devices, and to perform analytics on collected data, generate or apply universal or individualized models for glucose levels, and communicate such analytics, models, or information based thereon back to one or more of the devices in the system 100.

Figure 2:
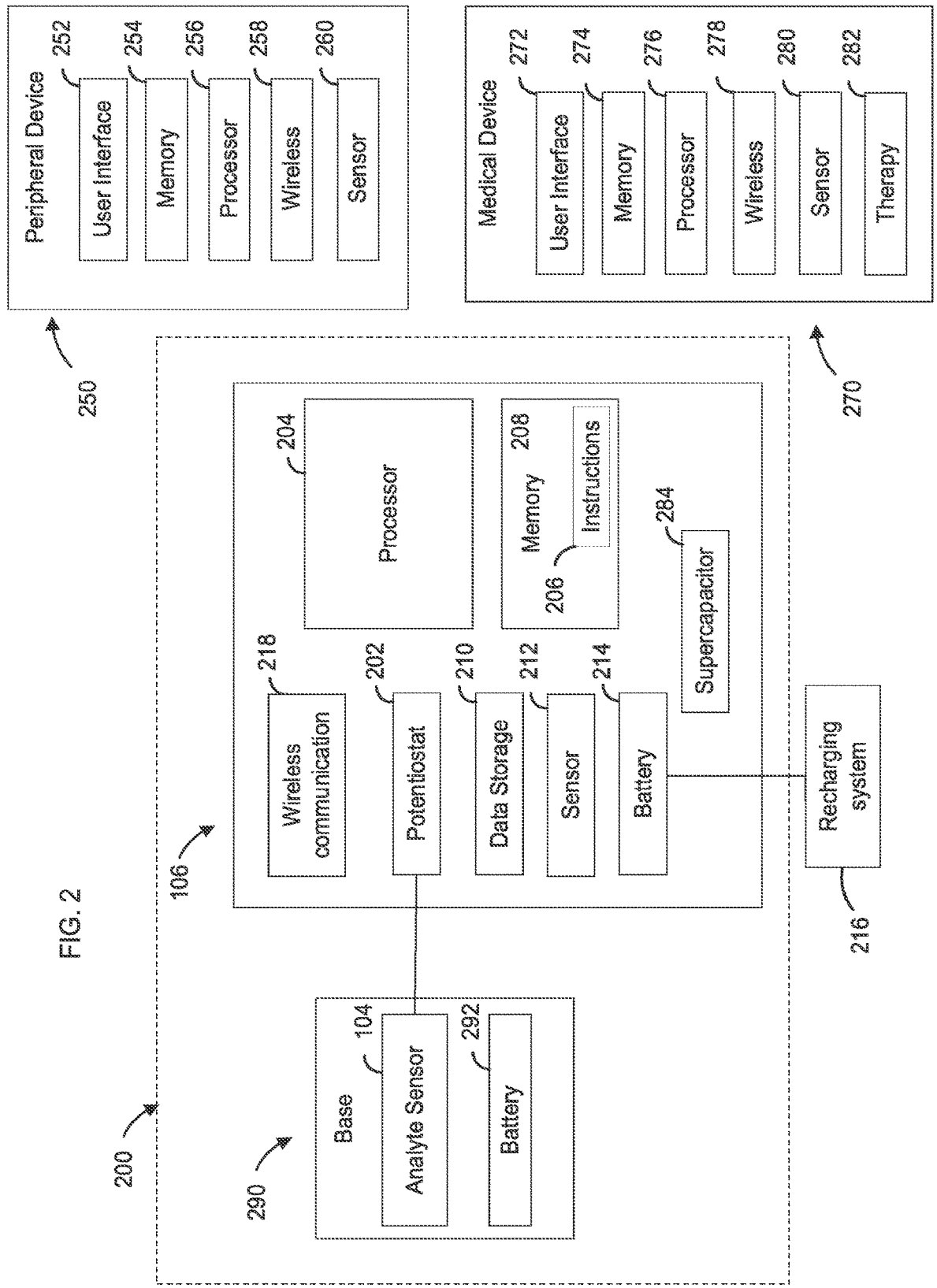
FIG. 2 is a schematic illustration of various example electronic components that may be part of the medical device system shown in FIG. 1, according to some embodiments.

FIG. 2 is a schematic illustration of various example electronic components that may be part of a medical device system 200. In an example, the system may include a sensor electronics 106 and a base 290. While a specific example of division of components between the base and sensor electronics is shown, it is understood that some examples may include additional components in the base 290 or in the sensor electronics 106, and the some of the components (e.g., supercapacitor 284) that are shown in the sensor electronics 106 may be alternative or additionally (e.g., redundantly) provided in the base. In an example, the base 290 may include the analyte sensor 104 and a battery 292. In some examples, the base may be replaceable, and the sensor electronics 106 may include a debouncing circuit (e.g., gate with hysteresis or delay) to avoid, for example, recurrent execution of a power-up or power down process when a battery is repeatedly connected and disconnected or avoid processing of noise signal associated with removal or replacement of a battery.

The sensor electronics 106 may include electronics components that are configured to process sensor information, such as sensor data, and generate transformed sensor data and displayable sensor information. The sensor electronics 106 may, for example, include electronic circuitry associated with measuring, processing, storing, or communicating continuous analyte sensor data, including prospective algorithms associated with processing and calibration of the sensor data. The sensor electronics module 106 may include hardware, firmware, and/or software that enables measurement of levels of the analyte via a glucose sensor. Electronic components may be affixed to a printed circuit board (PCB), or the like, and can take a variety of forms. For example, the electronic components may take the form of an integrated circuit (IC), such as an Application-Specific Integrated Circuit (ASIC), a microcontroller, and/or a processor.

As shown in FIG. 2, the sensor electronics 106 may include a potentiostat 202, which may be coupled to the analyte sensor 104 and configured to recurrently obtain analyte sensor readings using the analyte sensor, for example by continuously or recurrently placing a voltage bias across sensor electrodes and measuring a current flow indicative of analyte concentration. The sensor electronics may also include a processor 204, which may retrieve instructions 206 from memory 208 and execute the instructions to determine control application of bias potentials to the analyte sensor 104 via the potentiostat, interpret signals from the sensor, or compensate for environmental factors. The processor may also save information in data storage memory 210 or retrieve information from data storage memory 210. In various examples, data storage memory 210 may be integrated with memory 208, or may be a separate memory circuit, such as a non-volatile memory circuit (e.g., flash RAM). Examples of systems and methods for processing sensor analyte data are described in more detail herein and in U.S. Pat. Nos. 7,310,544 and 6,931,327.

The sensor electronics 106 may also include a sensor 212, which may be coupled to the processor. The sensor 212 may, for example, be a temperature sensor or an accelerometer. The sensor electronics 106 may also include a power source such as a capacitor or battery 214, which may be integrated into the sensor electronics, or may be removable, or part of a separate electronics package. The battery 214 (or other power storage component, e.g., capacitor) may optionally be rechargeable via a wired or wireless (e.g., inductive or ultrasound) recharging system 216. The recharging system may harvest energy or may receive energy from an external source or on-board source. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component.)

The sensor electronics may also include one or more supercapacitors 284 in the sensor electronics package (as shown), or in the base. For example, the supercapacitor 284 may allow energy to be drawn from the battery in a highly consistent manner to extend a life of the battery. The battery may recharge the supercapacitor after the supercapacitor delivers energy to the communication circuit or to the processor, so that the supercapacitor is prepared for delivery of energy during a subsequent high-load period. In some examples, the supercapacitor may be configured in parallel with the battery. A device may be configured to preferentially draw energy from the supercapacitor, as opposed to the battery. In some examples, a supercapacitor may be configured to receive energy from the rechargeable battery for short-term storage and transfer energy to the rechargeable battery for long-term storage.

The supercapacitor may extend an operational life of the battery by reducing the strain on the battery during the high-load period. In some examples, a supercapacitor removes at least 10% of the strain off the battery during high-load events. In some examples, a supercapacitor removes at least 20% of the strain off the battery during high-load events. In some examples, supercapacitor removes at least 30% of the strain off the battery during high-load events. In some examples, a supercapacitor removes at least 50% of the strain off the battery during high-load events.

The sensor electronics 106 may also include a wireless communication circuit 218, which may for example include a wireless transceiver operatively coupled to an antenna. The wireless communication circuit 218 may be operatively coupled to the processor and may be configured to wirelessly communicate with one or more peripheral devices or other medical devices, such as an insulin pump or smart insulin pen.

Peripheral device 250 may include, a user interface 252, a memory circuit 254, a processor 256, a wireless communication circuit 258, a sensor 260, or any combination thereof. The user interface 252 may, for example, include a touch-screen interface, a microphone (e.g., to receive voice commands), or a speaker, a vibration circuit, or any combination thereof, which may receive information from a user (e.g., glucose values) or deliver information to the user such as glucose values, glucose trends (e.g., an arrow, graph, or chart), or glucose alerts. The processor 256 may be configured to present information to a user, or receive input from a user, via the user interface 252. The processor 256 may also be configured to store and retrieve information, such as communication information (e.g., pairing information or data center access information), user information, sensor data or trends, or other information in the memory circuit 254. The wireless circuit communication circuit 258 may include a transceiver and antenna configured communicate via a wireless protocol, such as Bluetooth, MICS, or any of the other options discussed above. The sensor 260 may, for example, include an accelerometer, a temperature sensor, a location sensor, biometric sensor, or blood glucose sensor, blood pressure sensor, heart rate sensor, respiration sensor, or other physiologic sensor. The peripheral device 250 may, for example, be devices such as a hand-held smart device (e.g., smartphone or other device such as a proprietary handheld device available from Dexcom) 112, tablet 114, smart pen 116, watch 120 or other wearable device, or computer 118 shown in FIG. 1.

The peripheral device 250 may be configured to receive and display sensor information that may be transmitted by sensor electronics module 106 (e.g., in a customized data package that is transmitted to the display devices based on their respective preferences). Sensor information (e.g., blood glucose concentration level) or an alert or notification (e.g., "high glucose level", "low glucose level" or "fall rate alert" may be communicated via the user interface 252 (e.g., via visual display, sound, or vibration). In some examples, the peripheral device 250 may be configured to display or otherwise communicate the sensor information as it is communicated from the sensor electronics module (e.g., in a data package that is transmitted to respective display devices). For example, the peripheral device 250 may transmit data that has been processed (e.g., an estimated analyte concentration level that may be determined by processing raw sensor data), so that a device that receives the data may not be required to further process the data to determine usable information (such as the estimated analyte concentration level.) In other examples, the peripheral device 250 may process or interpret the received information (e.g., to declare an alert based on glucose values or a glucose trend. In various examples, the peripheral device 250 may receive information directly from sensor electronics 106, or over a network (e.g., via a cellular or Wi-Fi network that receives information from the sensor electronics or from a device that is communicatively coupled to the sensor electronics 106.)

Referring again to FIG. 2, the medical device 270 may include a user interface 272, a memory circuit 274, a processor 276, a wireless communication circuit 278, a sensor 280, a therapy circuit 282, or any combination thereof. The user interface 272 may, for example, include a touch-screen interface, a microphone, or a speaker, a vibration circuit, or any combination thereof, which may receive information from a user (e.g., glucose values, alert preferences, calibration coding) or deliver information to the user, such as e.g., glucose values, glucose trends (e.g., an arrow, graph, or chart), or glucose alerts. The processor 276 may be configured to present information to a user, or receive input from a user, via the user interface 272. The processor 276 may also be configured to store and retrieve information, such as communication information (e.g., pairing information or data center access information), user information, sensor data or trends, or other information in the memory circuit 274. The wireless circuit communication circuit 278 may include a transceiver and antenna configured communicate via a wireless protocol, such as Bluetooth, Medical Implant Communication System (MICS), Wi-Fi, Zigbee, or a cellular protocol (e.g., CDMA (Code Division Multiple Access) or GSM (Global System for Mobiles). The sensor 280 may, for example, include an accelerometer, a temperature sensor, a location sensor, biometric sensor, or blood glucose sensor, blood pressure sensor, heart rate sensor, respiration sensor, or other physiologic sensor. The medical device 270 may include two or more sensors (or memories or other components), even though only one is shown in the example in FIG. 2. In various examples, the medical device 270 may be a smart handheld glucose sensor (e.g., blood glucose meter), drug pump (e.g., insulin pump), or other physiologic sensor device, therapy device, or combination thereof. The medical device 270 may be the device 122 shown in FIG. 1.

In examples where the medical device 122 or medical device 270 is an insulin pump, the pump and analyte sensor system may be in two-way communication (e.g., so the pump can request a change to an analyte transmission protocol, e.g., request a data point or request data on a more frequency schedule, and the analyte sensor system provides the requested data accordingly), or the pump and analyte sensor system may communicate using one-way communication (e.g., the pump may receive analyte concentration level information from the analyte sensor system, for example, not in response to a request. In one-way communication, a glucose value may be incorporated in an advertisement message, which may be encrypted with a previously-shared key. In a two-way communication, a pump may request a value, which the analyte system may share, or obtain and share, in response to the request from the pump, and any or all of these communications may be encrypted using one or more previously-shared keys. An insulin pump to may receive and track analyte (e.g., glucose) values transmitted from analyte sensor system 102 using one-way communication to the pump for one or more of a variety of reasons. For example, an insulin pump may suspend or activate insulin administration based on a glucose value being below or above a threshold value.

In some examples, the system 100 shown in FIG. 1 may include two or more peripheral devices that each receive information directly or indirectly from the analyte sensor system 102. Because different display devices provide may different user interfaces, the content of the data packages (e.g., amount, format, and/or type of data to be displayed, alarms, and the like) may be customized (e.g., programmed differently by the manufacture and/or by an end user) for each particular device. For example, in the embodiment of FIG. 1, a plurality of different peripheral devices may be in direct wireless communication with a sensor electronics module (e.g., such as an on-skin sensor electronics module 106 that is physically connected to the continuous analyte sensor 104) during a sensor session to enable a plurality of different types and/or levels of display and/or functionality associated with the displayable sensor information, or, to save battery power in the sensor system 102, one or more specified devices may communicate with the analyte sensor system and relay (i.e., share) information to other devices directly or through a server system (e.g., network-connected data center) 126.

Example Methods

Figure 3:
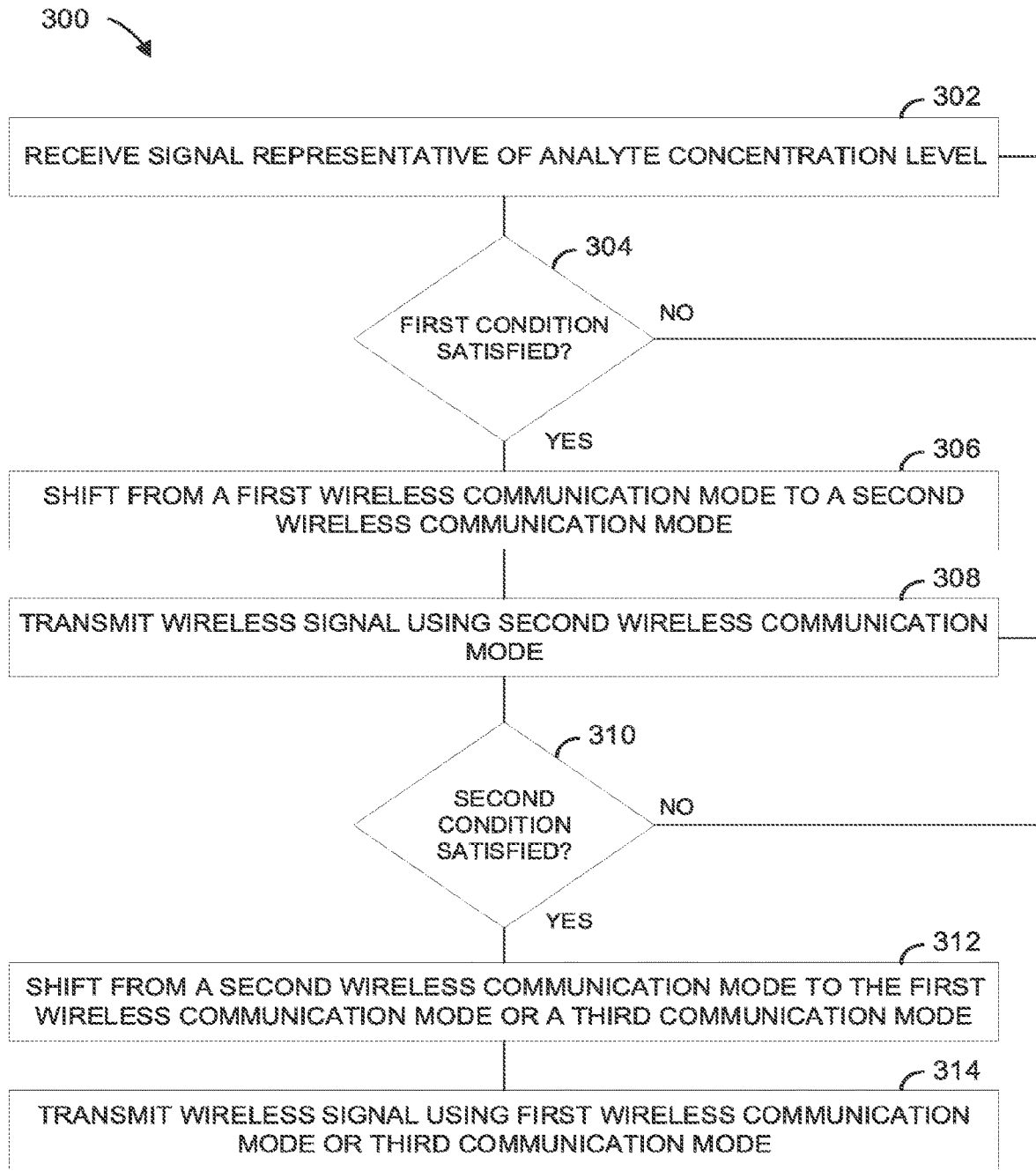
FIG. 3 is a flowchart illustration of an example method of managing power consumption in an analyte monitoring system, according to some embodiments.

FIG. 3 is a flowchart illustration of an example method 300 of managing power consumption in an analyte monitoring system. The method may, for example, include modulating power output from a first communication circuit to increase range or bandwidth by increasing power output and to conserve energy by decreasing power output from the first communication circuit. The method may, for example, be implemented in a system as shown in FIG. 1 or a device as shown in FIG. 2. The method may be repeated continuously or recurrently (e.g. periodically) or responsive to one or more events to manage power on an ongoing basis.

At 302, a signal representative of an analyte (e.g., glucose) concentration level may be received. The signal may be received, for example, from an analyte sensor, which may, for example, be a portion of a continuous glucose monitoring system as described above.

At 304, a determination is made as to whether a first condition is satisfied. In some examples, a processor operatively coupled to an analyte sensor (e.g., CGM processor) may determine whether the first condition is satisfied. In some examples, a processor in a peripheral device (e.g., smart phone or other display device) may determine whether the first condition is satisfied. Responsive to the condition not being satisfied, the method may return to step 302 and continue to receive analyte concentration levels.

In some examples, the first condition may be a connectivity condition, and step 304 may include determining whether the connectivity condition has been satisfied. The connectivity condition may, for example, include the existence of a connection (e.g. Bluetooth connection), a reliability of a connection (e.g., based upon the occurrence of successful connection attempts, or based on connection failures), or a quality of the connection based on one or more signal strength measurement parameters (e.g., a received signal strength indicator (RSSI.)) Determining whether the first condition is satisfied may include applying a connectivity parameter to a model. The model may include a plurality of communication states. The communication states may, for example, be based upon reliability of communication, elapsed time with consecutive successful communication sessions, elapsed time since an unsuccessful attempt (or series of attempts) to establish communication, or other measures of communication effectiveness or reliability.

The first condition may additionally or alternatively include an analyte management condition, such as a range (e.g., a glucose value range) or a trend (e.g. one or more analyte (glucose) levels being above or below a specified value or within a specified range, or a rate of change of analyte concentration levels being above or below a rate-of-change threshold.) In various examples, determining whether the first condition is satisfied may include analyzing the analyte signal, or an analyte parameter based on the analyte signal, to determine whether the analyte management condition is satisfied.

In some examples, determining whether a first condition is satisfied may, for example, include applying an analyte parameter to a model (e.g., a state model). In some examples, the condition may correspond to recognition of a state of disease management that is clinically relevant to the user of a peripheral device. A condition may, for example, be based upon by an analyte level (e.g. low estimated glucose level or high estimated glucose level), a trend (e.g., analyte concentration level rate of change or a predictive data), a deviation from a trend (e.g., reversal of a trend), or a probability of a clinically relevant condition occurring in the future (e.g., urgent low glucose soon).

In some examples, a condition may correspond to or be based upon one or more requirements of a peripheral device, such as an insulin pump. For example, a connectivity state may go from a low power usage model to a high-power usage model based upon a basal or bolus insulin deliver conditions (e.g., a high-power usage model or more reliable or frequency communication may be used when insulin is being delivered to avoid loss of a connection.)

In some examples, a state model may include a plurality of analyte concentration level states. An analyte concentration level state may be defined or determined by an analyte concentration range or trend (e.g., glucose below target range, glucose in target range, or glucose above target range.)

In some examples, a state model may additionally or alternatively include a plurality of communication states (e.g., low power state, high power state or high-reliability state, partnered state to coordinate with a peripheral device such as a pump, battery life extension state to assure that predicted battery life meets a battery life criterion.)

Responsive to the condition being satisfied, the method 300 may include, at 306, shifting from a first wireless communication mode to a second wireless communication mode responsive to satisfaction of a condition. In some examples, shifting from the first wireless communication mode to the second wireless communication mode includes reducing power output from a communication circuit to save energy. In some examples, the first wireless communication mode may consume more power than the second wireless communication mode. This shift to the second wireless communication mode may allow an analyte monitoring system to save power when the first condition is satisfied by shifting to the second wireless communication mode. In some examples, a system may balance need for communication and power consumption. For example, satisfaction of the first condition may be associated with a less urgent need for communication (e.g., a determination that analyte concentration levels and/or trends are in a "managed" range or state), in which case less frequent (e.g. on 15-minute intervals instead of 5-minute intervals), less power-demanding (e.g. lower transmit power or lower power protocol), or less automatic or on-demand communication (e.g. NFC instead of Bluetooth) communication may be acceptable. In some examples, a processor may monitor power consumption continuously or recurrently intermittently or may increase or decrease power consumption responsive to a protocol or satisfaction of a condition.

In some examples, the second wireless communication mode uses less power than the first wireless communication mode. In some examples, the first wireless communication mode may be a continuous connection mode as defined by a connection protocol (e.g., Bluetooth) and the second wireless communication mode may be a periodic connection mode. The periodic connection mode may require fewer wireless transmissions required to maintain an active state (e.g. based on a minimum connection interval) than the continuous connection mode. In some examples, the first wireless communication mode may be a two-way communication mode and the second wireless communication mode may be a one-way communication mode that includes data transmission from the first communication circuit. For example, the one-way communication mode may be a broadcast mode (e.g., in a Bluetooth protocol.) The one-way communication protocol may require less time actively transmitting and receiving, and therefore uses less power.

In some examples, the first wireless communication mode has a longer range than the second wireless communication mode. For example, the first communication mode may include a medium to long range wireless communication method or technology (e.g. Bluetooth or MICS communication), and the second communication mode may use a short-range wireless method or technology (e.g. NFC or inductive communication). Bluetooth tends to have a relatively long range (e.g., up to 100 m). MICS also tends to have a relatively long range (e.g., up to about 6 m), but the MICS range is usually shorter than Bluetooth. NFC and other inductive communication techniques tend to have a relatively short range (e.g., 4 cm up to about 30 cm), but require less power, no power, and in some examples can harvest power.

In some examples, an authentication process may be performed in the first communication mode (e.g., in a two-way communication scheme to allow for exchange of keys), and the system may shift to the second communication mode after authentication. In some examples, the system may transmit encrypted broadcast data via the second wireless communication mode. The encrypted broadcast data may, for example, include analyte concentration level information, trend information, or state information. In some examples, the encrypted broadcast data may be used to determine whether to shift from the second wireless communication mode to the first wireless communication mode (e.g., to determine whether the second condition is satisfied.) In some examples, the encrypted broadcast data may include an indication to shift back from the second wireless communication mode to the first wireless communication mode. For example, an analyte system processor (e.g., CGM processor) may apply an algorithm to determine whether to shift back to the first mode (e.g., back to two-way communication), and the peripheral device may transmit a bit flag in the broadcast packet. In some examples, a peripheral device (e.g., smart phone or other handheld display device) may apply an algorithm to determine whether to shift from the first mode to the second mode (e.g., to save power.)

After shifting to the second wireless communication mode, the method may include at 308 transmitting using the second wireless communication mode for a period of time, or until the satisfaction of a second condition (e.g., as determined at step 310.)

At 310, the method may include determining whether a second condition is satisfied. The second condition may be a different condition or may be an inverse of the first condition (e.g., an analyte level or trend moving out of range or otherwise satisfying or failing to satisfy a glucose management condition, or failure to satisfy a communication condition.) When the second condition is not satisfied, the method may return to transmitting the wireless signal using the second (e.g., low-power) wireless communication mode at 308.

Responsive to the second condition being satisfied, the method may include ceasing to use the second wireless communication mode. For example, when the second condition is satisfied, the method may include, at 312, shifting from a second wireless communication mode to the first wireless communication mode. In some examples, the method 300 may include shifting from the second communication mode back to the first communication mode includes increasing power output to increase communication range or bandwidth, and, at 314, communicating using the first wireless communication mode. Alternatively, the method may at 310 include shifting to a third wireless communication mode (e.g., to an intermediate power-consuming mode (e.g., intermittent two-way communication), or to a high-priority communication mode (e.g., continuous connection) that may consume more power than the first mode) and communicating using the third wireless communication mode at 314.

In some examples, the method 300 may include shifting from a one-way communication mode (e.g., broadcast) to a two-way communication mode when a sensor calibration is needed or to acknowledge that an alert or alarm has been received.

Figure 4:
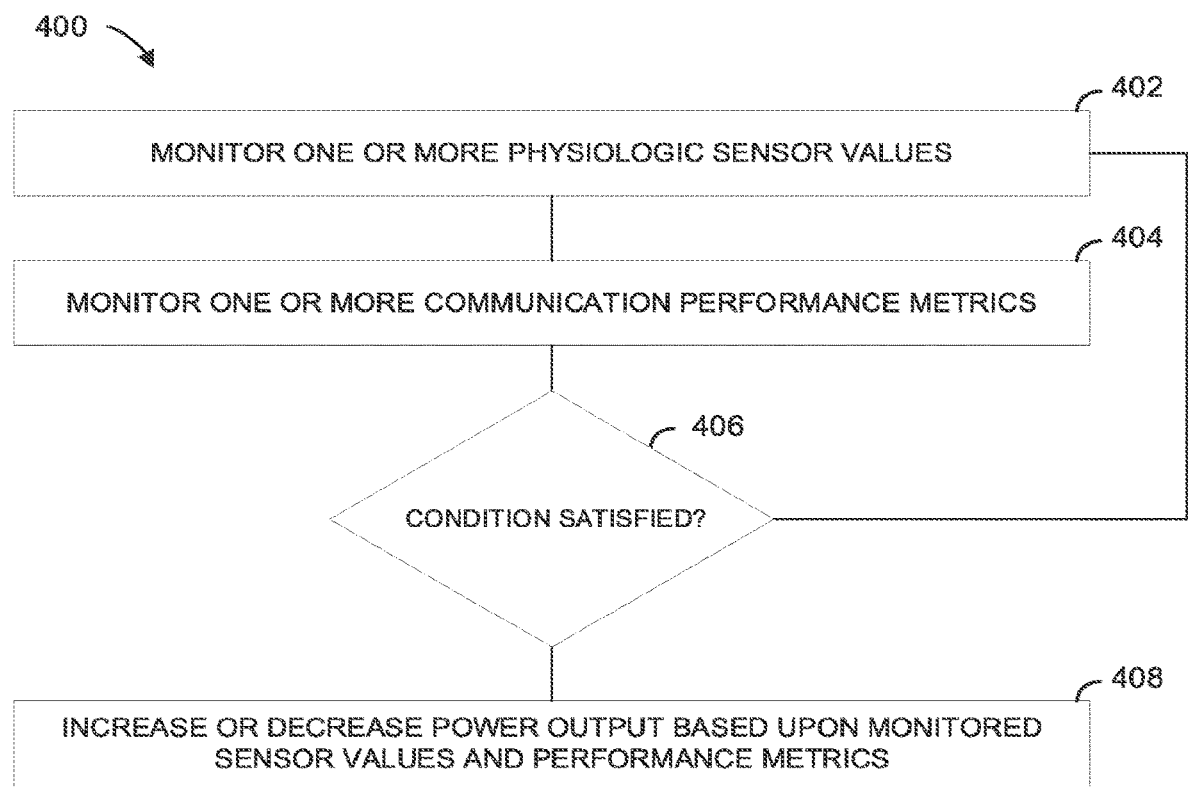
FIG. 4 is a flowchart illustration of an example method of managing power output based upon monitored sensor values or performance metrics, according to some embodiments.

FIG. 4 is a flowchart illustration of an example method 400 of managing power output based upon monitored sensor values or performance metrics. The method may be implemented, for example, in a system as shown in FIG. 1 or a device as shown in FIG. 2.

The method 400 may include, at 402, monitoring one or more physiologic sensor values (e.g., analyte concentration level, temperature, activity level, heart rate.). The physiologic sensor values may, for example, be received from a wearable sensor device that includes an analyte sensor (e.g., analyte sensor) and a communication circuit. The wearable sensor device may, for example, includes an analyte monitor, and the one or more physiologic sensor values include an estimated analyte concentration level.

The method may also include, at 404, monitoring one or more communication performance metrics pertaining to communication to or from the wearable sensor device. The communication performance metrics may, for example, include packet capture rates or received signal strength indicator values.

The method may further include, at 406, determining whether a condition is satisfied. The determination may, for example, be based at least in part upon the monitored physiologic sensor values (e.g., satisfaction of an analyte management condition) or the communication performance metrics (e.g., satisfaction of a communication reliability condition), or both or a combination thereof. For example, the method may include determining whether an analyte management condition is satisfied based at least in part on the estimated analyte concentration level. The analyte risk management condition may, for example, include a range, a trend, a projected analyte level, or other analyte management information. As described in detail above, the condition may correspond to recognition of a state of disease management that is clinically relevant to a user of a peripheral device The method may additionally or alternatively include determining whether a communication reliability condition is satisfied based at least in part on the communication performance metrics, and responsive to determining that the communication reliability condition is satisfied, conserving power by shifting to a more energy efficient communication scheme, or maintaining a current communication scheme (e.g., refraining from increasing power output). The communication reliability condition may, for example, be based on signal strength or packet rate falling below a threshold, or a combination thereof.

In some examples, the system may maintain the status quo (e.g., make no change) when a condition is satisfied. In some examples, a condition may be a negative condition, e.g., a negative condition may be satisfied when some combination of requirements is not met.

Responsive to the satisfaction of a condition, the method may further include, at 408, increasing or decreasing power output of the communication circuit. In some examples, the method may include shifting to a lower-power protocol. For example, the method may include shifting from a long-range communication protocol to a short-range communication protocol (e.g., MICS or Bluetooth to NFC), or from a continuously connected mode to a recurrently (e.g., periodically) connected mode, or from a two-way communication protocol to a one-way communication mode (e.g., broadcast mode.) In some examples, the method may include changing one or more communication parameters (e.g., shifting the communication mode). In some examples, the method may include periodically communicating the estimated analyte concentration level to another device and increasing or decreasing power output may include decreasing a frequency of communication of the estimated analyte concentration level.

In some example, increasing or decreasing power output may include shifting a frequency, shifting a mode, shifting a power level, or shifting a time period between communications, to increase communication range or reliability, or to conserve energy. For example, a system may shift between communicating one or more of once a minute, once every five minutes, once every ten minutes, or once every 30 minutes.

In some examples, increasing or decreasing power output may include restricting communication to a specified peripheral device of a plurality of available peripheral devices (e.g., increasing power to a pump but not to a smart watch). In some examples, the method may further include determining a specified peripheral device based on a schedule, a priority scheme, or a location. In some examples, the method may further include determining a battery status, wherein a communication scheme is modified based at least in part on the monitored physiologic sensor values, the communication performance metrics, and the battery status.

Figure 5:
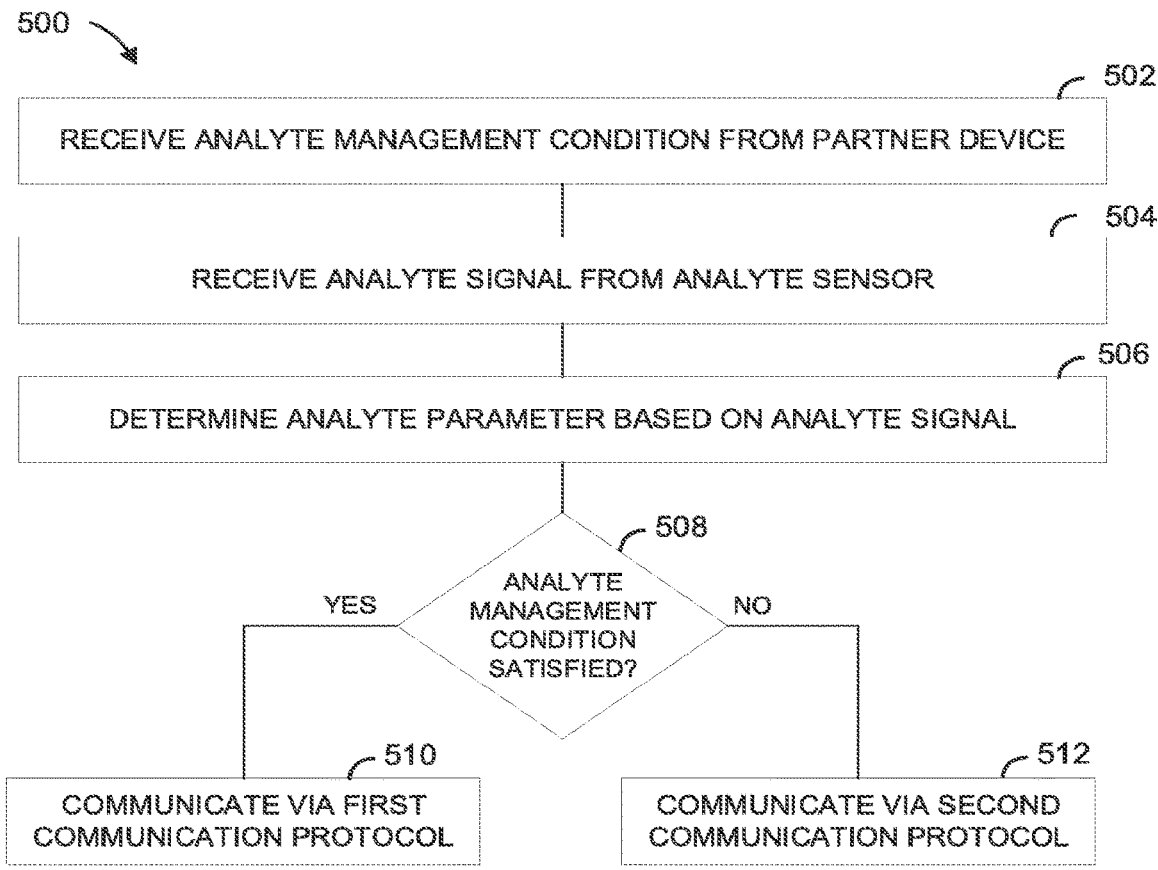
FIG. 5 is a flowchart illustration of an example method of selecting a communication protocol based upon satisfaction of an analyte management condition, according to some embodiments.

FIG. 5 is a flowchart illustration of an example method 500 of selecting a communication protocol based upon satisfaction of an analyte management condition. The method 500 may, for example, be applied to an analyte monitoring system including a communication circuit and an analyte sensor configured to generate a signal representative of an analyte concentration level, a processor configured to control operation of the system, and a battery configured to power the system. The method may be implemented, for example, in a system as shown in FIG. 1 or a device as shown in FIG. 2.

The method may include, at 502, receiving an analyte management condition from a partner device, such as an insulin pump or an insulin pen. The analyte management condition may include, for example, a range of analyte concentration levels (e.g., glucose concentration levels), a rate or change, or other parameter based on one or more analyte concentration levels. In various examples, the analyte management condition may be determined by the partner device or may be input by a user of the partner device.

At 504, the method 500 may further include receiving, e.g., from an analyte sensor, an analyte signal representative of an analyte concentration level (e.g., glucose concentration level.) The method 500 may also include, at 506, determining an analyte parameter based at least in part upon the analyte signal. For example, an estimated analyte concentration level (e.g., estimated glucose concentration level) may be determined. The method 500 may further include, at 508, determining a whether the analyte management condition is satisfied. The determination may be based at least in part on the analyte parameter. For example, the method may include determining whether an estimated analyte concentration level falls below a threshold, or exceeds a threshold, or a rate of change exceeds a rate of change threshold, or a predicted analyte concentration level meets a condition (e.g., above or below a threshold.) In some examples, determining whether the analyte management condition is satisfied may include applying the analyte parameter to a model (e.g., state model). The model may be predefined or may be learned from data, and may reside in the system (e.g., in the sensor electronics) or locally (e.g., on a smart device on or near the patient (host), or may reside on a remote system (e.g., on a networked resource.) One or more parameters (e.g., an analyte parameter) may be applied to the model (e.g., provided as input) and a state may be determined by applying the one or more parameters to the model. The state may, for example, relate to the host, such as a glucose state (e.g., in range, out of range, or trend) or may relate to communications (e.g., reliable or unreliable), or a combination thereof.

The method 500 may further include determining a communication protocol for communicating with the partner device based at least in part on whether the analyte management condition is satisfied. For example, the method may include, at 510 communicating via a first communication mode (e.g., power level, frequency, protocol) when the condition is satisfied, and, at 512, communicating via second communication mode when the condition is not satisfied. In an example, when an estimated analyte level (e.g., estimated glucose level) falls within a safe zone (e.g., 80 to 140 mg/DL), which may be specified by a partner device (e.g., insulin pump) or based upon a requirement or characteristic of the partner device, an analyte monitor (e.g., CGM) may communicate (e.g., advertise in a Bluetooth protocol) less frequently (e.g., every 15 or 30 minutes instead of continuously or every 1 or 5 minutes) to conserve power, or may shift to a one-way communication scheme, or may otherwise control operation of the system conserve power as described herein.

Figure 6:
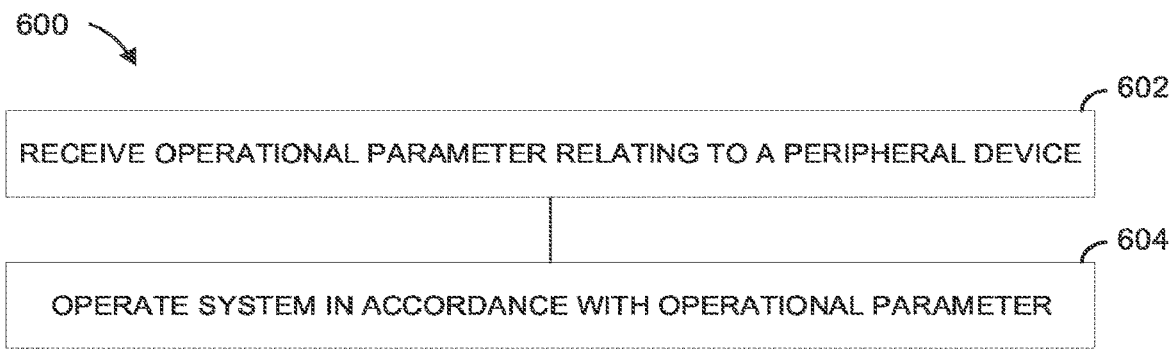
FIG. 6 is a flowchart illustration of an example method of managing power using an operational parameter received from a peripheral device, according to some embodiments.

FIG. 6 is a flowchart illustration of an example method 600 of managing power using an operational parameter received from a peripheral device. The method 600 may be implemented in an analyte monitoring system (e.g., CGM) including a communication circuit, an analyte sensor configured to generate a signal representative of an analyte concentration level, a processor configured to control operation of the system, and a battery configured to power the system. The method may, for example, be implemented in a system as shown in FIG. 1 or a device as shown in FIG. 2.

The method 600 may include, at 602, receiving via the communication circuit an operational parameter relating to a peripheral device. The peripheral device may, for example, include a drug pump, a smart pen, a handheld device (e.g., smart phone) or another type of display device that is configured to communicate with the analyte monitoring system. The operational parameter may be received from the peripheral device, or the operational parameter may be received from a remote resource (e.g., a server) or local device (e.g., smartphone app). In some examples, the operational parameter may be retrieved from a memory circuit based upon an identity or characteristic of the peripheral device (e.g., retrieved from a lookup table.) In an example, a system may communicate with a peripheral device and receive (or exchange) device identification information, and the system may then provide the device identification information (e.g., via a device such as a smart phone) and receive the operational parameter, which may be received from or determined by a remote resource (e.g., network server) or by a smart device.

In various examples, the operational parameter may, for example, include a battery management parameter, a calibration schedule parameter, a sensor accuracy parameter, or contextual information. In some examples, the operational parameter may include contextual information from the peripheral device (e.g., information about an interaction of the peripheral device with another device or a network environment.) For example, the operational parameter may include information about a connection state of the peripheral device (e.g., a network or remote server ("cloud") connection, RSSI, or a missed communication). In some examples, the operational parameter may include a status of the peripheral device, such as a battery level, an activity level (e.g., determined using an accelerometer on the peripheral device), location (e.g., GPS or based on network connection status or strength), display status (e.g., on or off), alert state (e.g., alert active or not active), alert acknowledged (e.g., input received from user to acknowledge receipt of alert), use mode (e.g., open loop or closed loop), or status of a pending event or action (e.g., waiting for an action or event.)

The method may further include, at 604, operating a system (e.g., analyte monitoring system such as a CGM) based at least in part upon the operational parameter. In various examples, a determination may be made based on the operational parameter, the system may be operated based at least in part on the determination. For example, the system may determine whether the operational parameter is within acceptable bounds. In some examples, the system may, for example, determine whether an analyte concentration is a defined analyte concentration range or satisfies a trend criterion, such as an average rate of change being below a threshold value.

In some examples, the operational parameter may include an operational requirement of the peripheral device. The method 600 may include controlling operation of the system to satisfy the operational requirement.

In an example, the operational requirement may include a sensor accuracy requirement and the system may be controlled to satisfy the sensor accuracy requirement (e.g., calibrate or replace a sensor that does not satisfy the sensor accuracy requirement). In an example, the operational requirement may include a calibration schedule, and the system may be operated to satisfy the calibration schedule (e.g., a system may prompt a user for calibrations to satisfy the schedule received from a partner device).

In an example, the operational requirement may include a battery life requirement, and the system may be operated to satisfy the battery life requirement (e.g., the system may suggest replacement of a battery, or a transceiver or other component that contains a battery, to assure that the battery life requirement is satisfied.) In some examples, the operational parameter may include a specified period of time (e.g., a pump session time), and operation of a system (e.g., continuous analyte sensor) may be controlled to manage energy consumption from the battery (e.g., analyte sensor battery) so that energy stored in the battery is not depleted before the specified period of time expires, e.g., the processor may control operation of the communication circuit in a manner calculated to assure that energy stored in the battery is not depleted before the specified period of time expires. For example, the processor may modify a communication scheme to conserve battery energy during the specified period of time. For example, the processor may shift to a communication mode that consumes less energy (e.g., shift from MICS or Bluetooth to NFC, shift from an always connected mode to a recurrent (e.g., periodic) communication mode, or shift from a two-way communication mode to a one-way (e.g., broadcast) communication mode.

In some examples, a system (e.g., analyte monitoring system) may be configured to communicate with a second device (e.g., in addition to a peripheral device such as a pump or smart pen), and the method may include restricting communication by the communication circuit so that the system communicates only with the peripheral device during the specified period of time. For example, the system may receive a whitelist (e.g., from the peripheral device or from a smart device or network resource) that the system may use during the specified period of time. In another example, the system (e.g., analyte monitoring system) may receive an operational parameter that indicates that the system may only communicate with the peripheral device during a specified period of time (e.g., the parameter may prescribe a communication schedule to reduce a need to broadcast). In another example, the system (e.g., analyte monitoring system) may receive an operational parameter that indicates that the system may communicate only with the peripheral device (e.g., with no other devices) during a specified period of time (e.g., to assure that a communication to a pump is successful). In another example, the system may receive an operational parameter to blacklist a communication device, such as a device that was previously connected with the system (e.g., a previous pump that was replaced may be blacklisted.)

In some examples, the operational parameter may include a specified number of additional peripheral devices, and the method may include communicating only with the peripheral device and the specified number of additional devices, wherein excessive consumption of energy stored in the battery is avoided by limiting the number of devices with which the analyte monitoring system communicates.

In some examples, the operational parameter may include an identification of one or more additional peripheral devices, and the method may include communicating only with the identified one or more additional devices, wherein excessive consumption of energy stored in the battery is avoided by limiting the number of devices with which the analyte monitoring system communicates. For example, an analyte monitoring system may communicate with a default or user-specified primary device. In some examples, the identification may specify a specific device, e.g., using a device ID. In some examples, the identification may specify a type of device (e.g. a watch). Types of peripheral devices may include, for example, a handheld device (e.g., smartphone), a watch, a tablet, a pen, a pump, or a desktop computer.

In some examples, a system (e.g., analyte monitoring system) may receive information about connections between peripheral devices. For example, an analyte system may receive information that a smart phone is in communication with a watch. Responsive to receiving information that a first peripheral device is in communication with a second peripheral device, the system may restrict communication to a specified device or group of devices (e.g., an analyte monitoring system may communicate with a smart phone, or smartphone and pump) and rely on the specified device to communicate with a third device (e.g., the smartphone may pass information to a smartwatch to reduce battery consumption by an analyte sensor system.)

In some examples, an operational parameter may be a schedule for providing information such as an analyte level or trend (or both), and a system may communicate according to the schedule. For example, an analyte signal representative of an analyte concentration level may be received from an analyte sensor, processed to determine an estimated analyte concentration level, and transmitted via a wireless signal (e.g., using a communication circuit) according to a schedule specified by the operational parameter.

In some examples, a system (e.g., analyte monitoring system) may receive an identification (e.g., list) of one or more authorized peripheral devices. The system may accept operational parameters or communication requests from one or more peripheral devices based upon the identification of authorized devices.

Figure 7A:
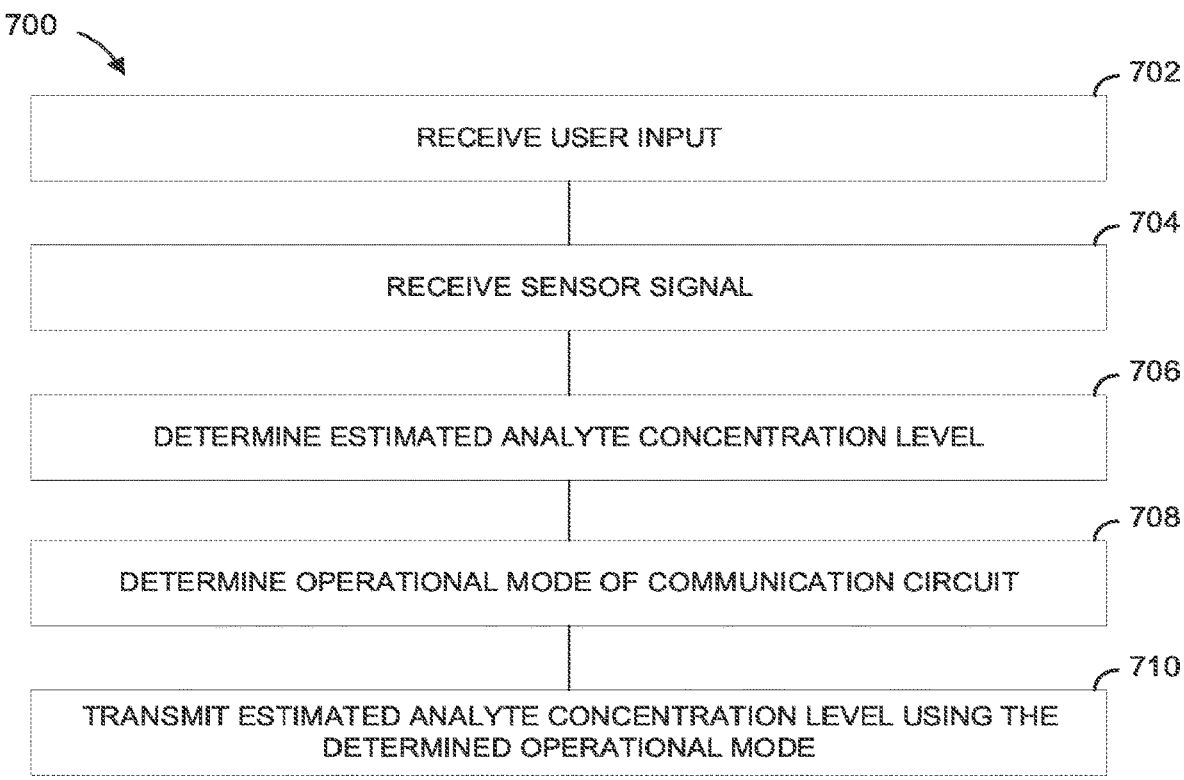
FIG. 7A is a flowchart illustration of an example method of managing power based upon user input, according to some embodiments.

FIG. 7A is a flowchart illustration of an example method 700 of managing power based upon user input. In some examples, the method 800 may be implemented in a system that may include an analyte sensor configured to generation a signal indicative of an analyte concentration level in a host, a processor configured to determine an estimated analyte concentration level based on the signal, a communication circuit configured to transmit the estimated analyte concentration level or information based on the estimated analyte concentration level via a transmitted communication signal, and to receive user input via a detected communication signal. The system may be configured to control a mode of communication for the communication circuit based at least in part on the user input. The system may, for example, be the system 200 shown in FIG. 2.

At 702, user input is received. The user input may be received directly, e.g., via a user interface (e.g., a graphical user interface GUI) or may be received from another device (e.g., a smart phone or other smart device) that may receive the user input via a user interface. In one example, the user interface may include menus and buttons (e.g., providing various options as described below), and the user may provide inputs via selecting the options from the menu and pressing the buttons. In some examples, the user input may be received over a network. For example, a host (e.g., child) to which an analyte sensor (e.g., glucose sensor) is attached may be in a first location, and the user (e.g., a caregiver) may provide the user input at a second location (e.g., via a smart phone) and the input may be relayed over a network (e.g., cellular network or the internet) to a smart device that is near the host.

The user input may, for example, include a request to initiate an energy-saving mode. The user input may also relate to energy management, e.g., the user input may include a request to align an estimated battery life with a parameter of a partner device (e.g., a pump session.) In some examples, the user input may include a specified condition. In some examples, responsive to satisfaction of the specified condition, the system may communicate less frequently or take other steps to consume less energy. In other examples, the system may enter a low-power consumption mode, and over-ride the low-power consumption mode responsive to satisfaction of the specified condition (e.g., estimated glucose level moving out of a safe range, or initiation of delivery of basal or bolus insulin by a pump.)

At 704, a sensor signal may be received from an analyte sensor. The sensor signal may, for example, be indicative of an analyte concentration level in a host (e.g., indicative of a glucose concentration.) The sensor signal may be received, for example, by a processor 204 as shown in FIG. 2 from an analyte sensor 104.

At 706, an estimated analyte concentration level (e.g., estimated glucose concentration level) is determined based on the sensor signal.

At 708, an operational mode of the communication circuit may be determined based at least in part on the user input. The determined operational mode may, for example, be an energy-saving mode, in which power consumption by the communication circuit or by the system may be reduced. The system may invoke any of the methods described herein to conserve or manage energy expenditure (e.g., the system may communicate less frequently than in a normal mode of operation or limit the number of devices with which the system communicates or communicate using a low-power technique (e.g., NFC) for non-critical communications or for all communications or for all communications.)

At 710, the estimated analyte concentration level, or information based on the estimated analyte concentration level, may be transmitted via the communication circuit using the determined operational mode. Transmitting using the energy-saving mode include, for example, transmitting information less often than in a normal operating mode, or transmitting using a less power-intensive mode of communication (e.g., NFC as opposed to Bluetooth), or communicating with fewer devices (e.g., communicating with a pump but not a watch), or communication via a peripheral device (e.g., communicating with a watch through a smartphone.

In some examples, a communication circuit may be controlled based at least in part on the analyte concentration level.

In some examples, a system (e.g., CGM system) may determine whether a condition is satisfied based at least in part on the analyte concentration level and control operation of the communication circuit to decreasing power consumption by the communication circuit based upon the determination of whether the condition is satisfied. For example, the condition may include range of analyte concentration levels, and determining whether the condition is satisfied may include determining whether the determined analyte concentration level falls within the range of analyte concentration levels. In an example, when an analyte concentration level is well controlled (e.g., estimated glucose level between 80 and 150 mg/dL and steady (e.g., no rapid rate of change)), a system may communicate less frequently that when an analyte concentration level is not well controlled (e.g., estimated glucose level beyond a specified threshold, e.g., below 70 mg/DL or over 150 mg/dL or 200 mg/DL or 250 mg/DL, or rising or falling quickly or a combination thereof.)

In some examples, the condition may include a trend condition, and determining whether the condition is satisfied may include determining whether the trend condition is satisfied using a plurality of analyte concentration levels. For example, a trend condition may include an analyte concentration level rate of change being below a specified threshold (e.g., estimated glucose rate of change not more than 2 mg/dL/minute or not more than 3 mg/dL/minute). The trend condition may also include an analyte concentration level (e.g., estimated glucose concentration level rate of change not more than 2 mg/dL per minute when the estimated glucose concentration level is less than 120 mg/dL.

In some examples, transmitting using the determined operational mode may include decreasing power consumption by refraining from automatic transmission of analyte concentration information, or transmitting analyte concentration information less often. In some examples, transmitting using the determined operational mode may include transmitting only in response to a request (e.g., shift to a "pull" mode instead of "push" mode), or transmitting less often unless a request is received (e.g., a request from a partner device or a user.)

In some examples, a determined operational mode may be overridden to communicate responsive to an analyte concentration level falling below a threshold or outside a range.

In some examples, the user input may include a specification of a condition, and the operation of the communication circuit may be modified responsive to satisfaction of the condition. The condition may, for example, includes a range of analyte concentration levels or an analyte trend condition, or any other condition discussed herein.

In some examples, a patient state may be determined based upon one or more analyte concentration levels, and operation of the communication circuit may be modified to reduce power consumption responsive to the patient state satisfying a safety condition. For example, a patient state may be determined by applying one or more analyte concentration levels to a model, such as a state model that may include one or more states determined by the model responsive to analyte concentrations level(s), and optionally also determined by contextual factors or information about the device (e.g., battery level) or an information about partner device (e.g., a pump.)

In some examples, the user input may include a request to operate the system in a manner to assure that an estimated battery life matches or exceeds an operation parameter relating to a partner device. For example, the operational parameter may be a period of time (e.g., a pump session time), and the system may operate the in a manner to extend the life of a battery in the system so that the battery does not expire (e.g., be depleted to a charge level that is insufficient to perform a function) before the period of time expires.)

In some examples, the system may monitor for an alert condition based at least in part upon the estimated analyte concentration level and the system may override the energy savings mode to communicate an alert.

In some examples, a determined operational mode of communication may include a hibernation mode (e.g., low-power consumption mode). In the hibernation mode, a system may stop communication, or may communicate only very infrequently, or may only list but not transmit, or transmit very unfrequently, or one or more non-communication operations (e.g., sensing) may be suspended, or any combination thereof. In some examples, a system may enter a hibernation mode responsive to a user input that includes a request to stop a sensor session, or responsive to a request to start a sensor session (e.g., because after starting a session a sensor may not be used during a warm-up period in which the host/sensor adapts to the insertion of a sensor into the host). In some examples, the system may shift out of the hibernation mode after a specified period of time (e.g., after expiration of a warm-up period.)

Figure 7B:
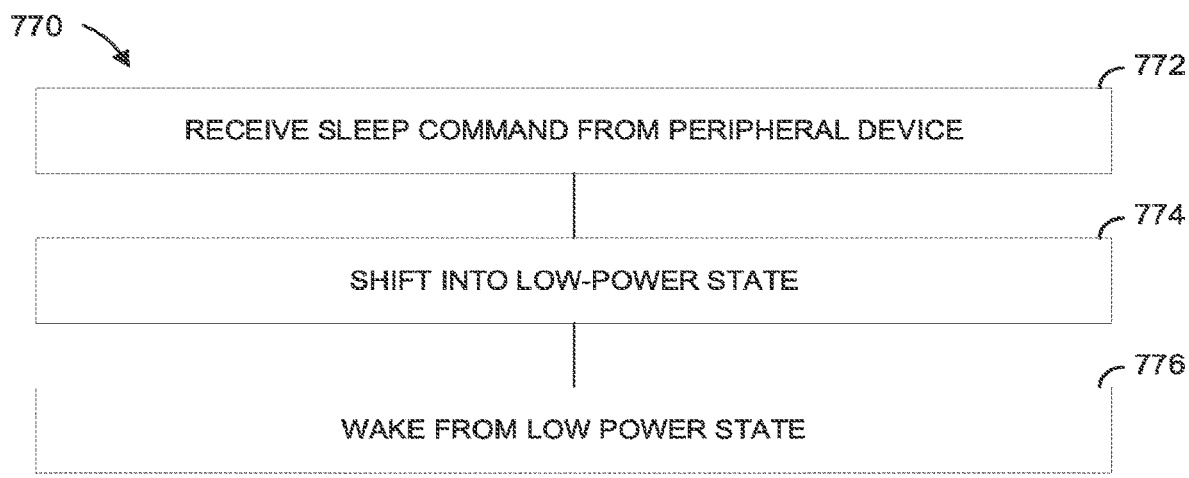
FIG. 7B is a flowchart illustration of an example method of managing power based upon a sleep command, according to some embodiments.

FIG. 7B is a flowchart illustration of an example method 700 of managing power based upon a sleep command (e.g., an instruction to enter a hibernation mode or other low-power consumption state.) The method may be applied, for example, to an analyte monitoring system including a communication circuit and an analyte sensor configured to generate a signal representative of an analyte concentration level, a processor configured to control operation of the system, and a battery configured to power the system. The method may be implemented, for example, in a system as shown in FIG. 1 or a device as shown in FIG. 2.

The method 770 may include, at 772, receiving via the communication circuit a sleep command from a peripheral device. It may be desirable, for example, to cause an analyte monitoring system to sleep during a warm up period (e.g., after application of a sensor to a host, a warm-up period may be required before sensor readings begin.) The method 770 may include, at 774, shifting the system into a low-power state responsive to receipt of the sleep command. In some examples, the system may stop communicating in a sleep state. For example, a communication circuits may stop sending and receiving completely for a period of time, or the communication circuit may enter a listening-only mode, which may optionally involve a lower-power listening mode than normal operation (e.g., longer duty cycles or wake up and listen on a schedule.) In some examples, other portions of a system may also stop consuming energy or enter a low-power mode. For example, analyte sensor may stop applying a sensing voltage to an electrode or a processor may stop collecting or processing data. In another example, when the system is in the low power mode, the analyte sensor may still continue to apply voltage for analyte measurement purposes, however, the transmission/communication circuit may remain in the sleep or low power mode. Yet, in another example, when sensor electronics are removed from a host (e.g., when a transmitter is disconnected from a sensor), the sensor electronics may stop processing or communicating (e.g., because the sensor electronics are not receiving sensor data anyway.)

The method may include, at 776, waking the system from the low power state. In some examples, the system may include a clock that triggers a wake-up event when a period of time (e.g., warm-up period) expires, e.g., using a timer or at a specified time. In some examples, the method may include waking the analyte monitoring system in response to a wake-up command, e.g., in response to a command from a peripheral device such as a pump or a smart device (e.g., smart phone or proprietary hand-held device)

Figure 8:
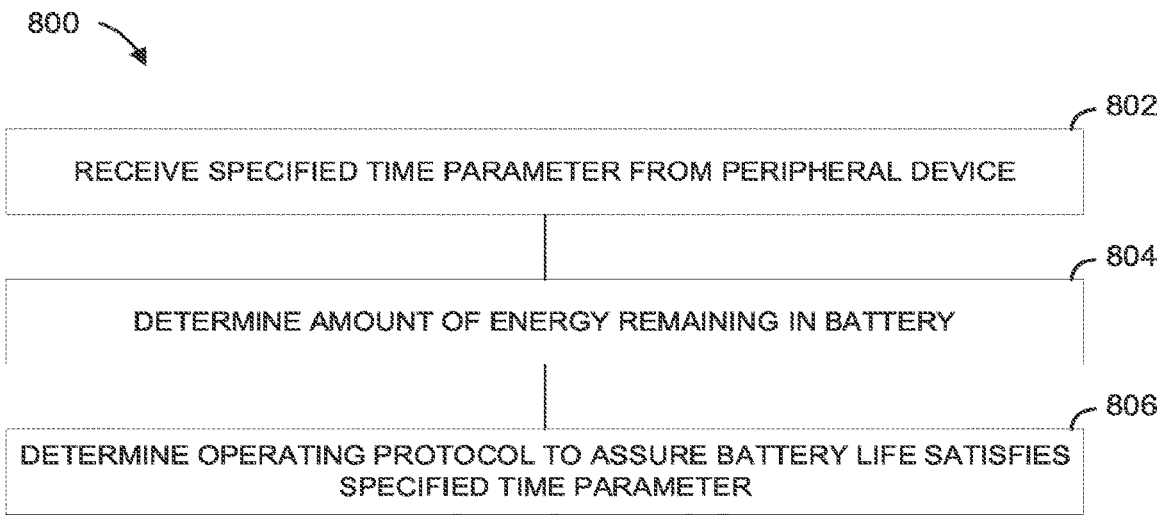
FIG. 8 is a flowchart illustration of an example method of determining an operating protocol to assure battery life satisfies a specified time parameter, according to some embodiments.

FIG. 8 is a flowchart illustration of an example method 800 of determining an operating protocol to assure battery life satisfies a specified time parameter. The method may be applied, for example, to an analyte monitoring system that includes a communication circuit and an analyte sensor configured to generate a signal representative of an analyte concentration level, a processor configured to control operation of the system, and a battery configured to power the system. The method may be implemented, for example, in a system as shown in FIG. 1 or a device as shown in FIG. 2.

The method 800 may include, at 802, receiving a specified time parameter from a peripheral device. The specified time parameter may, for example, be a specified time, such as a specific date (e.g., date, week, or month), or an amount of time, such as a number of days, weeks, or months. The method 800 may further include, at 804 determining an amount of energy remaining in a battery, e.g. based upon a voltage measurement, a current measurement, a coulomb counter, or any combination thereof. The method 800 may further include, at 806, determining a system operating protocol calculated to assure that projected energy consumption by providing an estimated battery life that satisfies the specified time parameter. For example, a projected energy consumption rate may be determined based on one or more communication parameters (e.g., strength of transmissions, how often the system communicates, or how many devices with which the system will communicate), one or more data processing parameters (e.g., how much data processing will occur, and how often it will occur), one or more sensing parameters (e.g., how often a sensor reading will be obtained), or any combination thereof. In an example, the lifetime or expiration of an analyte sensor system (e.g., CGM) may be aligned with or extended to exceed the lifetime or expiration of a pump, e.g., a CGM may be operated to assure that the battery life of the CGM outlast the battery life of the pump or changing of a pump insertion site. In some examples, the system may assure that enough battery remains at the end of the session to perform one or more end-of-session tasks, such as transferring data to an external device such as a smartphone. In some examples, a notification may be delivered to a user to change or check an analyte sensor system battery to coordinate battery replacement with pump replacement or insertion site change.

Figure 9:
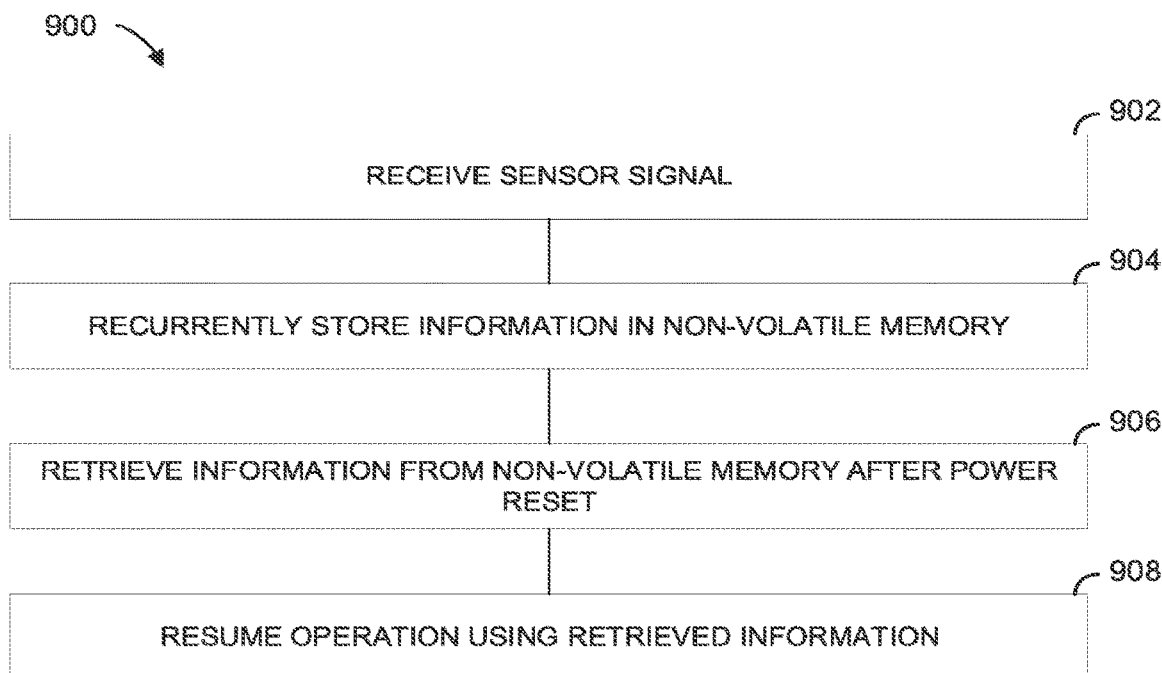
FIG. 9 is a flowchart illustration of an example method of using information from a non-volatile memory after a power reset, according to some embodiments.

FIG. 9 is a flowchart illustration of an example method 900 of using information from a non-volatile memory after a power reset. The method may be implemented, for example, in a system as shown in FIG. 1 or a device as shown in FIG. 2.

The method 900 may include, at 902, receiving a sensor signal representative of an analyte concentration level from a wearable analyte monitor. The method 900 may further include, at 904, recurrently storing information in a non-volatile memory in preparation for an unplanned power reset, such as when a removeable battery is removed from a device. The stored information may include, for example, an estimated analyte concentration level determined from the sensor signal, and an associated time stamp. In some examples, the method 900 may also include storing time data, session data, pairing information, reset counts, or battery effects of resets in the nonvolatile memory. A reset count and effect of resets may be accounted for in an estimation of battery life remaining.

In some examples, periodically storing information may include storing critical information. Critical information may be used to reestablish a session after a power reset and continue the session according to operating parameters that were in use prior to the power reset. For example, a mode (e.g., communication mode, operating mode of a device, or mode of interaction with a peripheral device such as a pump) or status (e.g., analyte trend or patient status) may be resumed after a power reset.

The method 900 may further include, at 906, retrieving the stored information from the nonvolatile memory after a power reset. In some examples, the method may further include initiating a power-up mode after a power reset and using the stored information to assess device status or an analyte status in the power-up mode. In some examples, a debouncing circuit (e.g., gate with hysteresis) may be used to avoid recurrent execution of a power-up or power down process when a battery is repeatedly connected and disconnected or avoid processing of noise signal associated with removal or replacement of a battery. In some examples, a system may execute instructions to remove noise associated with removal or insertion of a battery. For example, a system or device may detect connection or disconnection of a battery, and the system may delay a power up or power-down process or delay processing of a signal for a specified period of time after a connection or disconnection from the battery is detected. In some examples, a system or device may delay a power-down process for a specified period of time after a connection to a battery is detected, which may allow the system or device to avoid successive execution of power-up and power-down processes when a battery is connected and disconnected multiple times in a short time window.

The method may further include, at 908, resuming operating using the retrieved information. In some examples, the method may further include determining an operating mode based at least in part on the stored information. In some examples, the determined operating mode may include one or more of a power consumption mode or a communication mode. For example, the system may determine using stored information whether to operate in a low power operating mode, normal operating mode (e.g., default), or high-power operating mode (e.g., high frequency communication or high power to assure range or high probably of communication success, which may be useful for example when the patient is in an unmanaged condition, e.g., in or trending toward a high glucose state or low glucose state.)

In some examples, a low-power mode may be initiated based on a battery condition (e.g., based on current, voltage, or remaining energy) or the amount of battery life remaining (e.g., time until expiration or estimated time until satisfaction of an end-of-life condition). In various examples, the low-power mode may conserve power by communicating less often, or shifting to from a first communication mode or protocol to a second mode or protocol that uses less power (e.g., shift from Bluetooth to NFC), or communicating with fewer devices, or relying on a peripheral device to communicate with another device (e.g., engaging a smartphone to communicate to a watch, pump, or smart pen), or performing a non-communication operation (e.g., sensing) less often, or offloading processing to a peripheral device (e.g., rely on a smartphone for complex processing). In some example, the determination of whether to operate in the low-power mode after a power reset may be based upon battery power after reset (e.g., to detect whether a battery with sufficient power (e.g., new battery) has been inserted, or whether a low-power battery (e.g., the same battery as was removed, or another low-power battery) has been inserted. In some example, a power level assessment (e.g., decision whether to operate in a low-power mode) may be triggered after a power reset based upon information stored before the reset (e.g., based on one or more of the mode of operation before reset, or an analyte management condition (e.g., glucose level or trend), or communication condition (e.g., reliable or not) or communication mode (e.g. 2-way or 1-way.))

In some examples, the method may include determining an analyte trend a based at least in part on an estimated analyte concentration level retrieved from the nonvolatile memory.

In some examples, the method may include periodically saving first information on a first schedule and periodically saving additional information on a second schedule, the first information being saved more frequently than the additional information. For example, information that is critical for resuming a session after a power reset may be saved more frequently than other types of information.

Example Battery and Device Structures

Figure 10A:
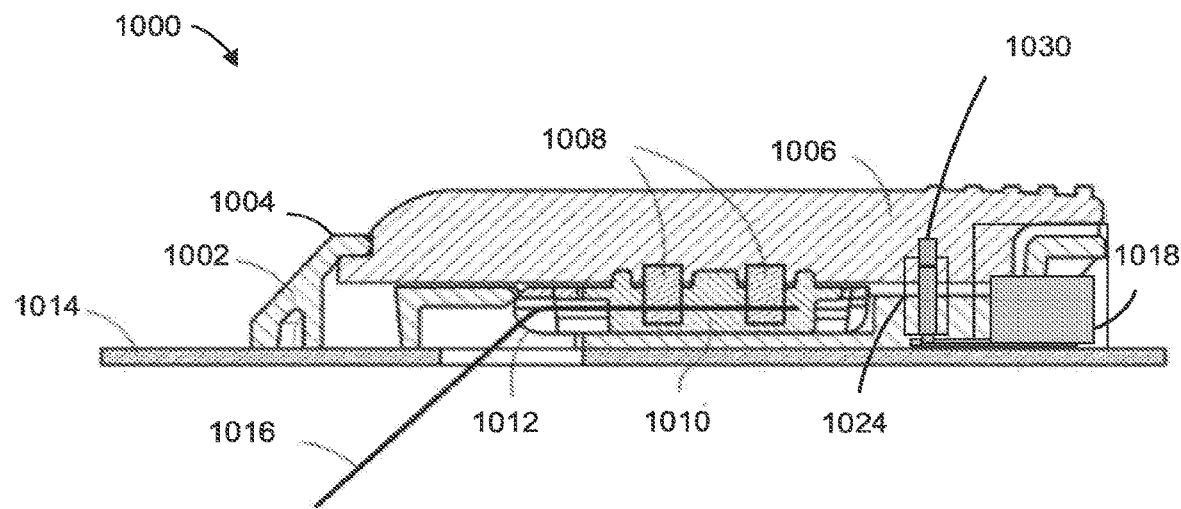
FIG. 10A is a cross sectional view of an example sensor assembly, according to some embodiments.

FIG. 10A is a cross sectional view of an example sensor assembly 1000. The sensor assembly 1000 may include a base 1002 that may include a mounting unit 1004 that is configured to couple with a sensor electronics module 1006, which may be or include the sensor electronics module 106 of FIGS. 1 and 2. The sensor assembly 1000 may also include one or more batteries 1018, which may be removable or replaceable. Battery 1018 may be electrically coupled to an electrical contact 1028, which may be sized and shaped to electrically couple with an electrical contact 1030 on the sensor electronics module 1006, as further explained below.

The base 1002 may include contacts 1008, which may be part of a contact subassembly 1010. The contacts 1008 may be configured to electrically and mechanically contact respective contacts (not shown) on the sensor electronics module, e.g., to enable signal transfer or power transfer. The contact subassembly 1010 may include a hinge 1012 that is configured to allow the contact subassembly 1010 to pivot between a first position (for insertion) and a second position (for use) relative to the mounting unit 1004. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some examples, the contacts 1008 may be formed from a conductive elastomeric material, such as a carbon filled elastomer, in electrical connection with the sensor 1016.

In some examples, the mounting unit 1004 may be provided with an adhesive pad 1014, disposed on the mounting unit's back surface. The adhesive pad may include a releasable backing layer. The mounting unit 1004 may be adhered to the skin of a host by pressing the base 1002 of the mounting unit and the adhesive pad 1014 onto the skin. Appropriate adhesive pads can be chosen and designed to stretch, elongate, conform to, and/or aerate the region (e.g., host's skin). Various configurations and arrangements can provide water resistant, waterproof, and/or hermetically sealed properties associated with the mounting unit/sensor electronics module embodiments described herein. Any of the examples discussed herein may be sealed to avoid, for example, exposure to water or excessive exposure to moisture.

Figure 10B:
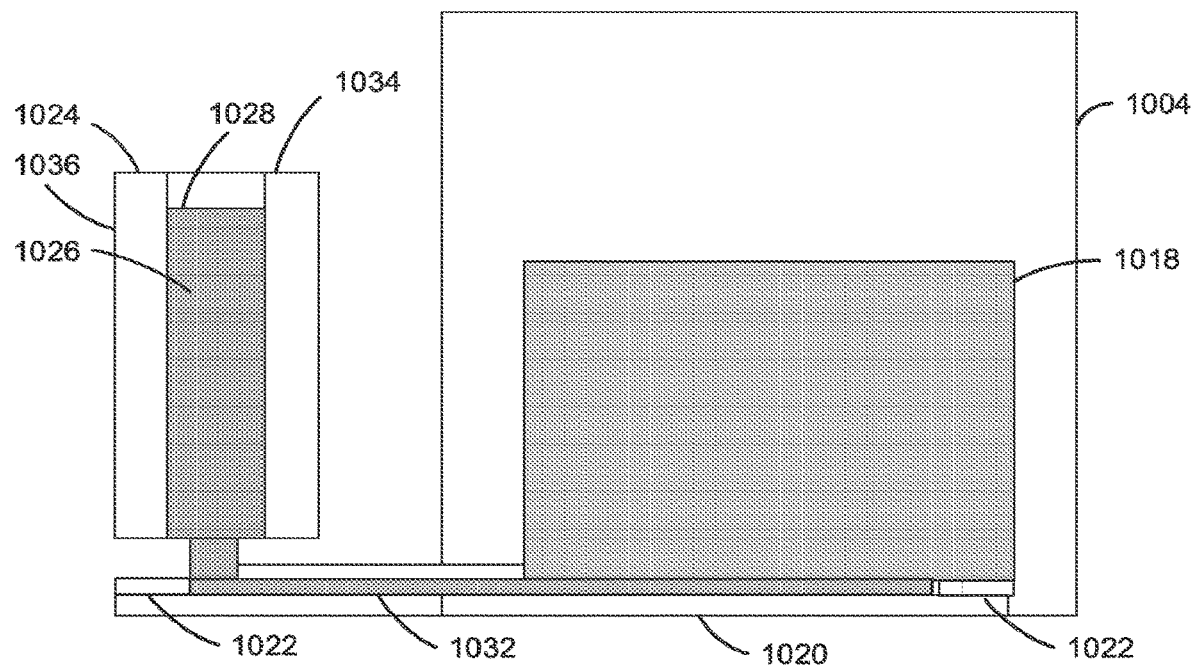
FIG. 10B is an enlarged portion of the sensor assembly of FIG. 10A.

FIG. 10B is an enlarged view of a portion of the sensor assembly of FIG. 10A. The base 1002 may be configured to receive one or more batteries 1018, which may for example be coin cell batteries (e.g. silver oxide, lithium, alkaline, zinc air, etc.). A sealed region 1020 may extend over the batteries to isolate and secure the batteries 1018 in the base 1002. In various embodiments, the sealed region may be coupled to the base using mechanical connections (e.g. snap fit), adhesives, welded joints, or any combination thereof.

The base 1002 may include one or more protrusions 1024 (e.g., seal member or seal feature) that extend upward to the sensor electronics module 1006. Electrical connector 1026 may extend through the protrusion 1024 and electrically connect via electrical contact 1028 with a second electrical contact 1030 on the sensor electronics module 1006. In some examples, an end surface 1034 of the protrusion 1024 (e.g., sealing member) may seal against an opposing surface on the sensor electronics module to form a seal (e.g., face seal.) In some examples, an outer side surface 1036 of the protrusion 1024 may seal against a corresponding surface (e.g., an inner surface on a cavity on sensor electronics module 1006) to form a radial seal (e.g., an O-ring or lip seal against the sensor electronical module.)

In the example shown in FIGS. 10A and 10B, the protrusion 1024 and electrical connector 1026 are laterally offset from the one or more batteries (i.e., to the right of the battery in FIG. 10B), in which case the electrical connector 1026 may be electrically coupled with the battery via electrical connector 1032. In some alternative examples, such as the embodiment shown in FIG. 13A, the protrusions may extend upward from batteries, as shown, for example, in FIG. 11A.

The protrusions 1024 may form a seal with the sensor electronics module 1006 when the sensor electronics module is assembled with the base 1002. For example, the protrusions may form a radial seal or face seal with the sensor electronics module 1006. The protrusions may be overmolded to a base or over or around the electrical contact 1028. Alternatively, a seal component may be coupled to the protrusion (e.g., the protrusion itself may be integral with the base and a seal component may be overmolded to the base or otherwise coupled to or placed around the protrusion.) The protrusions or seal may be formed of a material to form a water-tight seal, such as an elastomeric or conformable material (e.g., Silicone, TPE, Polypropylene, etc.)).

Each of the example bases shown in FIGS. 10A through 39C may include one or more electrical contacts 1028, 1029 that may be configured to deliver battery power to a sensor electronics module (e.g., sensor electronics module 106 or sensor electronics module 1006, not shown in FIGS. 11A-39C). While some of the examples are shown with two batteries, other examples may include a single battery, or more than two batteries (e.g., three, four, or more batteries.) In various examples, the batteries may all be the same, or the batteries may be sized differently, or may have difference electrical or electrochemical properties to provide desired performance characteristics (e.g., current capacity or battery life.) In examples with two or more batteries, the batteries may be arranged in series or parallel, but preferably in series, so that one contact 1028 is positive and the other contact 1029 is negative (or vice-versa) to thereby form a closed circuit when coupled with the sensor electronics module. The base may also include electrical contacts 1008, 1010, which may be configured to interface with the sensor electronics module to operatively couple one or more sensor system components (e.g., potentiostat 202 shown in FIG. 2) to supply power to generate a sensor signal (e.g., to apply a bias to via sensor 1016 to generate a signal indicative of an analyte concentration level). In some examples, a cover, film, flex circuit substrate, potting material (e.g., epoxy), or other component may be provided and configured to extend over the batteries and seal with the base. A sealed interface may be created using one or more of a sealing member (e.g. O-ring or elastomer), ultrasonic welding, laser, radiofrequency (RF), or heat welding. A sensor electronics sealing member may also be provided between the sensor electronics module 1006 and the base. In any of the examples shown in FIGS. 10A-39C, the batteries may be coupled to a sensor electronics package via conductive elastomeric contacts (e.g., pucks), springs, tabs, posts, pogo pins, flat conductive pads or traces, or any other suitable conductive materials and/or structures, which may in various configurations be affixed to the base, or to a sensor electronics module. Any of the structural elements shown in FIGS. 10A-39C may be combined with an example shown in another of the FIGS. 10A-39C, and many of the examples may have similar or identical components, as shown in the drawings.

A battery seal may be provided between the sensor electronics module and the batteries or battery contacts, for example to avoid contact between the batteries and the outside environment (e.g., water during swimming or bathing), which may corrode, deplete, or damage the batteries or electronic components. The battery seal may, for example, be a face seal, radial seal (e.g., O-ring), or an irregular seal. The seal may, for example, include an overmolded component such as an overmolded gasket, an overmolded elastomeric feature that may be coupled to or assembled with the base or sensor electronics module, or other overmolded or assembled seal components or features. The seal or seals may create one continuous seal around the perimeter of both batteries (e.g., see FIGS. 12A and 15A, 16A, 18A, and 19A), or may create a seal around each battery individually (e.g., see FIGS. 11A, 13A, 14A, and 23A-39C). In various configurations, the batteries 1018 may be assembled into the base through the bottom of the base (e.g., see FIGS. 11A and 11B, 13A-16B, 20A-25B, 28A-34 and 38A-39C), or through the top of the base (e.g., see FIGS. 12A-12B, 17A-19B, 26A-37B and 35A-37D).

Any of the examples shown in FIGS. 11A through 39C may be coupled to an adhesive component such as adhesive pad 1014 shown in FIGS. 10A, 23A-23C, 28A-28C, 30A-30B, 32, 34, 36 and/or 38A-38B, or alternatively or additionally may include adhesive on the bottom surface 1052 of the base, to couple the base to a host.

Figures 11A, 11B:
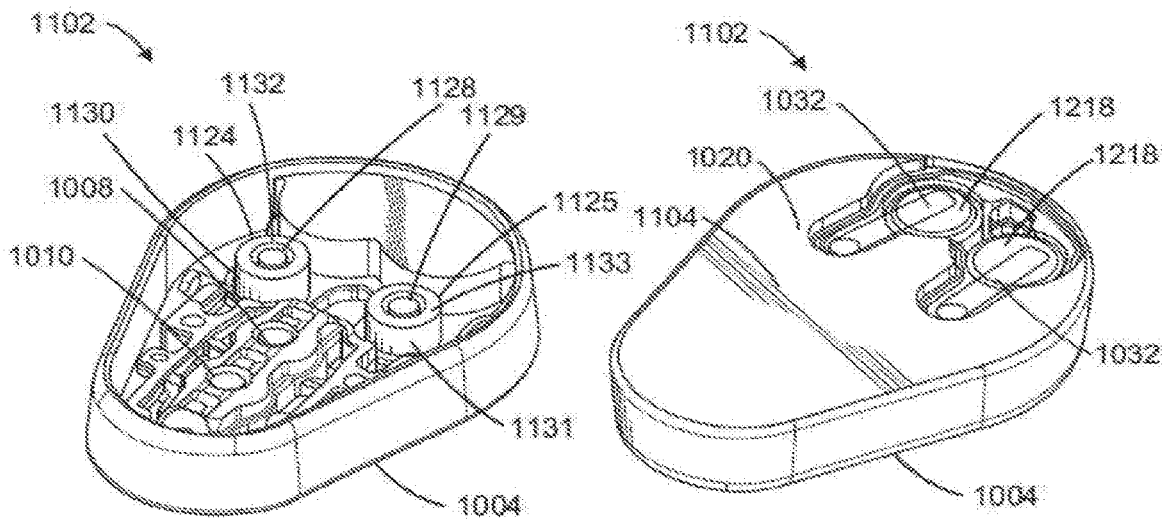
FIG. 11A is a perspective top view of an example sensor base, according to some embodiments.
FIG. 11B is a perspective bottom view of the base shown in FIG. 11A.

FIG. 11A is a perspective top view of an example sensor base 1102 that has two protruding seal members 1124, 1125, which may be offset from batteries 1018. FIG. 11A shows electrical contacts 1128, 1129 as conductive elastomeric puck style contacts that may press against corresponding contacts (not shown) on the sensor electronics modules when the sensor electronics module is assembled with the base 1102. Battery power may be supplied to the sensor electronics module via electrical contacts 1128, 1129. The seal members 1124, 1125 may be configured to seal against a sensor electronics module (not shown) so that electrical contacts 1128, 1129 may be sealed from exposure to potential environmental elements, such as water. The seal members 1124, 1125, may, for example be overmolded elastomeric seal (e.g., overmolded onto the base.) The seal members 1124 may form a face seal when pressed against sensor electronics module. In an example, the outer side surfaces 1130, 1131 of the sensor electronics module may seal against one or more inner surfaces of corresponding cavities in the sensor electronics module. Alternatively, or additionally, end surfaces 1132, 1133 may form a seal against opposing surfaces on the sensor electronics module.

FIG. 11B is a perspective bottom view of the base 1102. The batteries 1018 may be sealed in the base. In some examples, the analyte sensor 1016 (not shown in FIG. 11B) may be delivered through the bottom surface 1104 of the base 1102 and into a host, e.g., through a hole (not shown in FIG. 11B) in the sealed region 1020 (e.g., cover.) The analyte sensor 2016 may, for example, be delivered via a mechanical or electrical delivery system (e.g., applicator, not shown), which may, for example, be configured to insert a needle/sensor assembly into a host and withdraw the needle to leave the sensor in the host for sensing an analyte (e.g., glucose) concentration. Example sensor delivery systems are shown and described in U.S. Pat. No. 7,949,381, U.S. patent application Ser. No. 15/387,088 (published as US20170188910A1), and U.S. patent application Ser. No. 15/298,721 (published as US20170112534A1) which are incorporated by reference. Any of the examples shown in FIGS. 11A-39C may be similarly configured to receive a sensor 1016 and sensor delivery system.

The base 1102 and the bases shown in FIGS. 12A-39C may include a mounting unit 1004, electrical contacts 1008, 1010, and a sealed region 1020, as described in reference to at least FIGS. 10A and 10B.

Figures 12A, 12B:
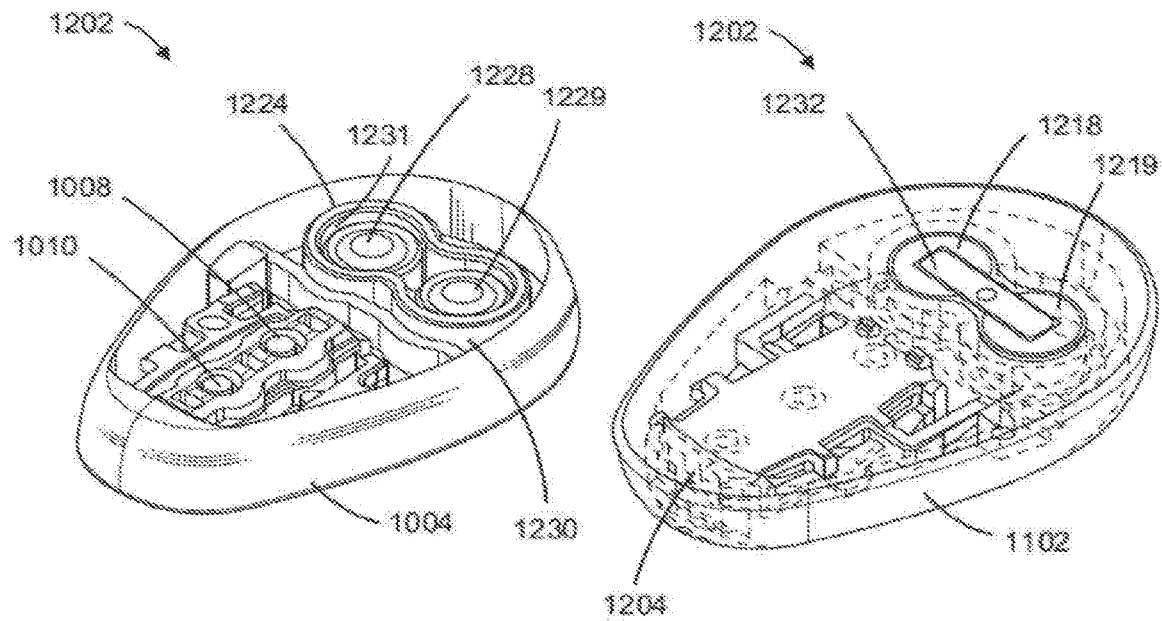
FIG. 12A is a perspective top view of an example sensor base, according to some embodiments.
FIG. 12B is a perspective bottom view of the base shown in FIG. 12A.

FIGS. 12A and 12B illustrate an example base 1202 in which batteries may be loaded from a top side as opposed to a bottom side as shown in FIG. 11B. A seal member 1224 may extend around both batteries 1218, 1219 and optionally also around battery contacts 1228, 1229. Battery contacts 1228, 1229 may be separate parts, or may be a portion of a battery. The seal member 1224 may be overmolded to the base or assembled with the base and placed around battery contacts 1228, 1229, or around the battery contacts 1228, 1229 and the batteries 1018. An outer surface 1230 of the seal member 1224 may be configured to seal against an opposing internal surface (e.g., inner surface of a cavity) on the sensor electronics module (e.g., sealed against inner surface 1952 on sensor electronics module 1904 in FIG. 19B). Additionally, or alternatively, an inner surface 1231 of the seal member 1224 may be configured to seal against an opposing surface on the sensor electronics module. As shown in FIG. 12B, the batteries 1218, 1219 may be electrically coupled via connector 1232. A sensor (e.g., sensor 104 or sensor 1016) may be delivered via a passageway in the base such as the hole 1240 shown in FIG. 12B.

Figures 13A, 13B:
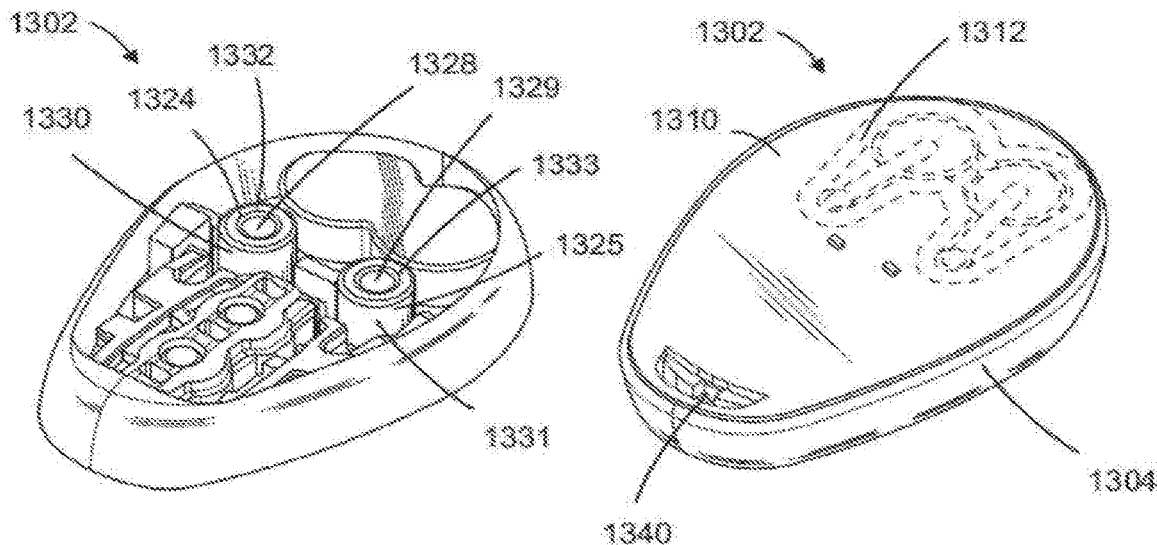
FIG. 13A is a perspective top view of an example sensor base, according to some embodiments.
FIG. 13B is a perspective bottom view of the base shown in FIG. 13A.

FIGS. 13A and 13B illustrate an example base 1302 that includes seal members 1324, 1325 having side surface 1330, 1331 that may form a face seal with corresponding surfaces on the sensor electronics module (e.g. seal against inner surfaces of a cavity on sensor electronics module) to seal battery electrical contacts 1328 1329 against exposure to water or moisture. Additionally. or alternatively, the end surfaces 1332, 1333 may form a seal against the sensor electronics module.

FIG. 13B shows a film 1310 (or alternatively flex circuit substrate) that may be laser or heat bonded (e.g., glued or welded) to the mounting unit 1304 to seal the batteries in the mounting unit 1304. For example, a sealed path 1312 may be laser bonded or heat bonded around the batteries to create an isolated region around the batteries. A sensor (e.g., sensor 104 or sensor 1016) may be delivered via a passageway in the base such as the hole 1340 shown in FIG. 13B.

Figures 14A, 14B:
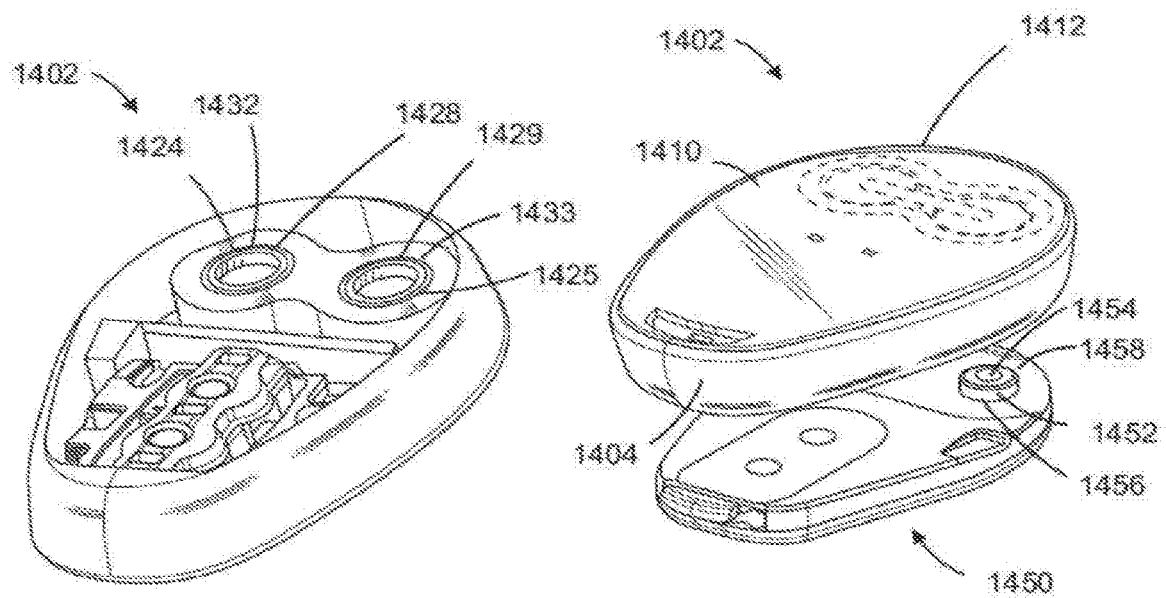
FIG. 14A is a perspective top view of an example sensor base, according to some embodiments.
FIG. 14B is a perspective bottom view of the base shown in FIG. 14A and an example sensor electronics module configured to mechanically and electrically couple with the base shown in FIGS. 14A and 14B.

FIGS. 14A and 14B illustrate an example base 1402 and sensor electronics module 1450. The sensor electronics module may include one or more protrusions 1452 (e.g., second protrusion is behind base and thus not shown) that include one or more electrical contacts 1454 that is configured to electrically couple with electrical contacts 1428, 1429 on the base 1402. Protrusion 1452 may be configured to fit into corresponding recesses 1434, 1435 in seal members 1424, 1425 so that one or more outer surfaces 1456 on the protrusion form a radial seal with seal members.

The seal members 1424, 1425 may also optionally have end surfaces 1432, 1433 that may be sized and shaped to form seal against an opposing surface 1458 on the sensor electronics module to further seal battery electrical contacts 1428 1429 against exposure to water or moisture.

FIG. 14B shows a film 1410 (or alternatively flex circuit substrate) that may be laser or heat bonded to the mounting unit 1404 to seal the batteries in the mounting unit 1404. For example, a sealed weld path 1412 may be laser bonded or heat bonded around the batteries to create an isolated region around the batteries.

Figure 15A:
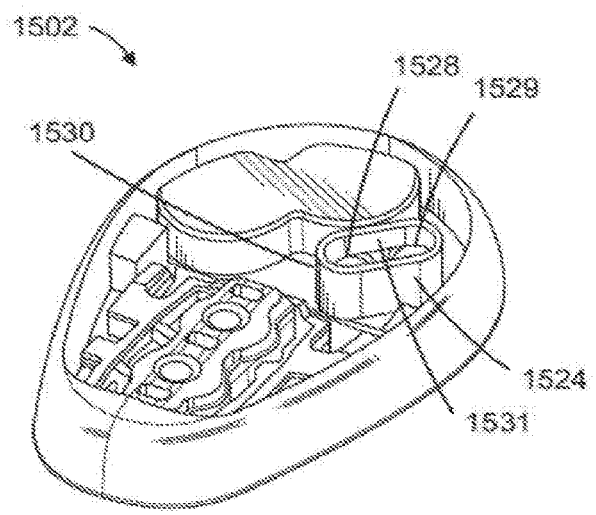
FIG. 15A is a perspective top view of an example sensor base, according to some embodiments.
Figure 15B:
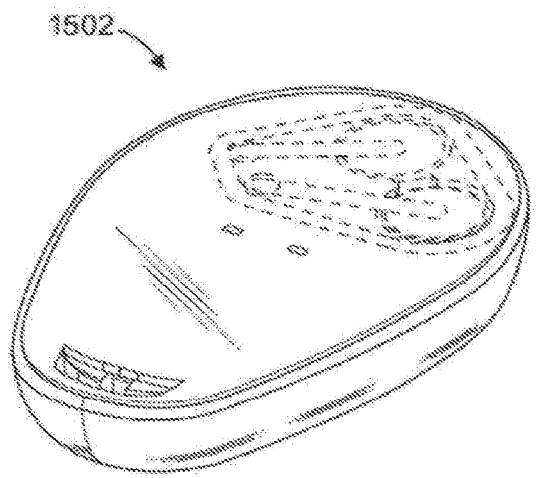
FIG. 15B is a perspective bottom view of the base shown in FIG. 15A.

FIGS. 15A and 15B illustrate an example base 1502 having a seal member 1524 that may extend around one or more battery contacts 1528, 1529. An outer surface 1530, inner surface 1531, or both, may be configured to seal against corresponding opposing surfaces on a sensor electronics module (not shown in FIG. 15A, 15B) to form a seal around both battery contacts. The seal member 1524 may, for example, be an overmolded elastomeric gasket.

Figure 16A:
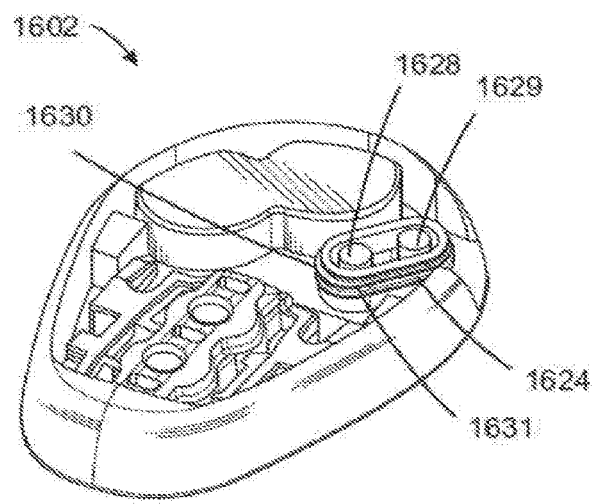
FIG. 16A is a perspective top view of an example sensor base, according to some embodiments.
Figure 16B:
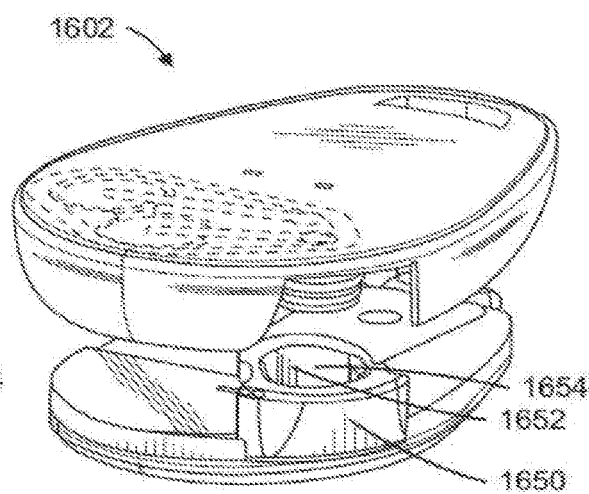
FIG. 16B is a perspective bottom view of the base shown in FIG. 16A and an example sensor electronics module configured to mechanically and electrically couple with the base shown in FIGS. 16A and 16B.

FIGS. 16A and 16B illustrate an example base 1602 having a seal member 1624 that may extend around one or more battery contacts 1628, 1629. An outer surface 1630 of the seal member may include one or more ribs 1631 that may form a radial seal (e.g., similar to an O-ring) with an inner surface 1652 of a cavity 1654 formed by the sensor electronics module 1650. The seal member 1624 may, for example, be a molded elastomeric seal placed over the battery contacts 1628, 1629. In another example, the seal member 1624 may be overmolded onto the base.

Figure 17A:
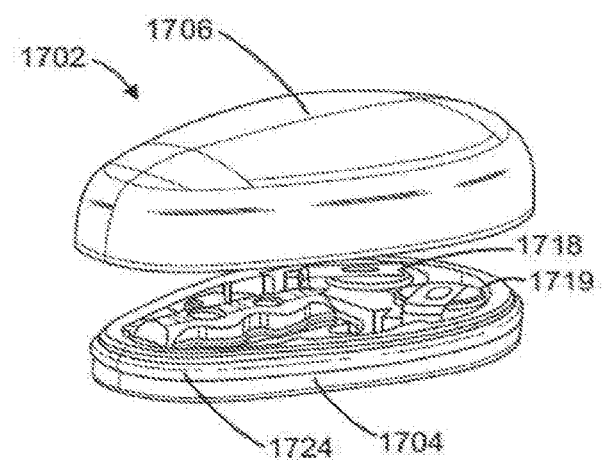
FIG. 17A is an exploded (disassembled) perspective top view of an example sensor base and example sensor electronics module, according to some embodiments.
Figure 17B:
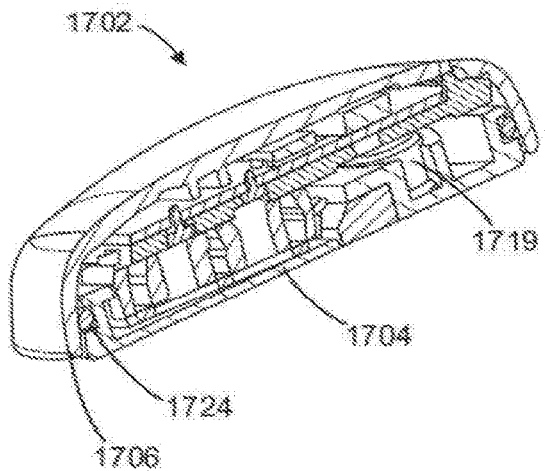
FIG. 17B is a perspective view of the base shown in FIG. 17A assembled with the sensor electronics module.

FIGS. 17A and 17B illustrate an example base 1702 that includes a radial seal (e.g., O-ring seal) that extends around a bottom component 1704 of the base. The radial seal 1724 and a top component 1706 (which may be a portion of a sensor electronics module) may be configured to form a fluid-tight seal to avoid exposure to water or moisture.

Figure 18A:
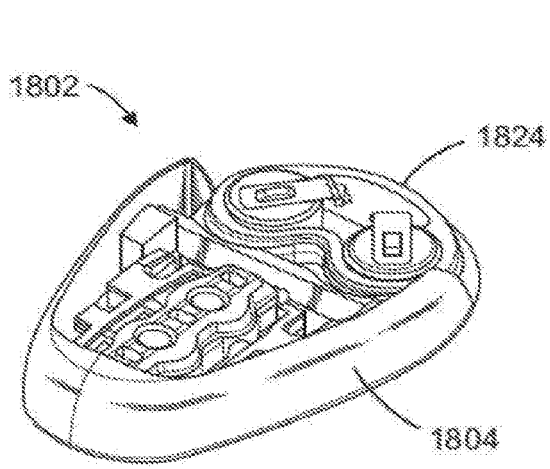
FIG. 18A is a perspective top view of an example sensor base, according to some embodiments.
Figure 18B:
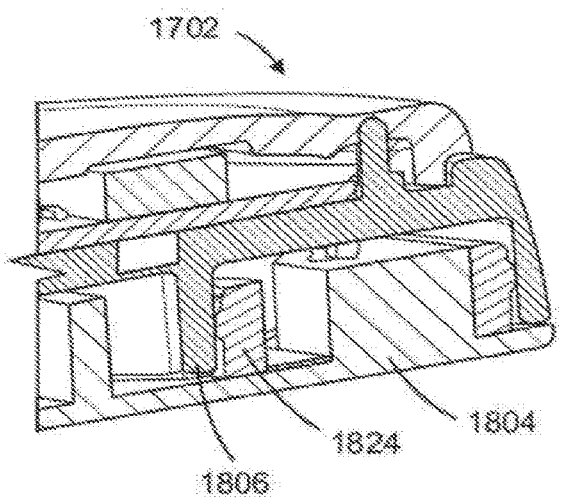
FIG. 18B is an enlarged perspective view of the base shown in FIG. 17A assembled with an example sensor electronics module.

FIGS. 18A and 18B illustrate an example base 1802 that includes a radial seal that extends around a bottom component 1804 of the base. The radial seal 1824 and a portion 1806 of a sensor electronics module may be configured to form a fluid-tight seal to avoid exposure to water or moisture. The radial seal 1824 may, for example, be or include an overmolded elastomeric feature (e.g., overmolded onto the base so that it extends around inserted batteries or battery contacts).

FIGS. 19A and 19B illustrate an example base 1902 that includes a seal member 1924 that extends around both batteries 1918, 1919. The seal member 1924 may be overmolded to the base, and sized and shaped to extend around batteries 1918, 1919 (or around the battery contacts (not shown) and the batteries). An outer surface 1930 of the seal member 1924 may include a ring feature 1931 that may be configured to seal against an opposing internal surface 1954 in a cavity on sensor electronics module 1950.

FIGS. 20A and 20B illustrate another example base 2002 that includes a single seal member 2024 that may include a cavity 2126 that may be configured to receive a protrusion 2052 extending from a bottom side 2054 of a sensor electronics module 2050. The seal member 2024 may be configured to seal against an outer surface 2058 of a protrusion. In some examples, the seal member 2024 may form a face seal with the protrusion 2052, or may form a radial seal (e.g., via an internal rib (not shown) in the cavity 2026 on the seal member). The protrusion 2052 may include one or more electrical contacts 2056 (e.g., a second contact, not shown, may be on the other side of the protrusion to complete a circuit, see, e.g., FIG. 21B.) The electrical contacts 2056 may electrically couple with corresponding contacts (not shown) on an inside surface of the seal member 2024 (e.g., on the walls inside the cavity 2026 on the seal member 2024 that receives the protrusion.)

FIGS. 21A and 21B illustrate another example base 2102 that includes a single seal member 2124 that may include a cavity 2126 that may be configured to receive a protrusion 2152 extending from a bottom side 2154 of a sensor electronics module 2150. The seal member 2124 may be configured to seal against an outer surface 2158 of a protrusion. In various examples, the seal member 2124 may form a face seal with the protrusion 2152, or may form a radial seal (e.g., via an internal rib (not shown) in the cavity 2126 on the seal member). The protrusion 2152 may include one or more electrical contacts 2156, 2160. The electrical contacts 2156, 2160 may electrically couple with corresponding contacts (not shown) on an inside surface of the seal member 2124 (e.g., on the walls inside the cavity 2126 on the seal member 2124 that receives the protrusion.)

FIGS. 22A and 22B illustrate another example base 2202 that is similar to the example 1102 shown in FIG. 11A, but in which seal members 2224, 2225 are situated in a front portion 2204 of the base 2202.

Toe-In Embodiments

Several embodiments utilizing a protrusion or "toe" on a sensor electronics module to secure the sensor electronics module to a base are described in connection with FIGS. 23A-29C below.

While not shown in FIGS. 23A-29C, bases 2302-2902 can comprise an analyte sensor (e.g., analyte sensor 104 of FIG. 1, analyte sensor 212 of FIG. 2, analyte sensor 1016 of FIG. 10A) configured to generate a sensor signal indicative of an analyte (e.g., glucose) concentration of a host, while sensor electronics modules 2350-2950 can include sensor electronics (e.g., sensor electronics 106 of FIGS. 1 and/or 2) as described herein and may include at least a wireless transceiver configured to transmit a wireless signal based at least in part on the sensor signal generated by the analyte sensor.

In some embodiments, an analyte sensor base assembly may include base 2302-2902 configured to attach to a skin of a host and one or more of the analyte sensor as described above and configured to generate a sensor signal indicative of an analyte concentration level of the host, at least one battery at least as will be described below, at least one sensor contact 2308-2908 and/or 2310-2910, at least one battery contact 2328-2938 and/or 2329-2929, a sealing member 2324-2924 configured to provide a seal around at least the at least one battery contact 2328-2938 and/or 2329-2929, and/or any other features associated with and/or configured to couple with base 2302-2902 at least as described below.

Figure 23A:
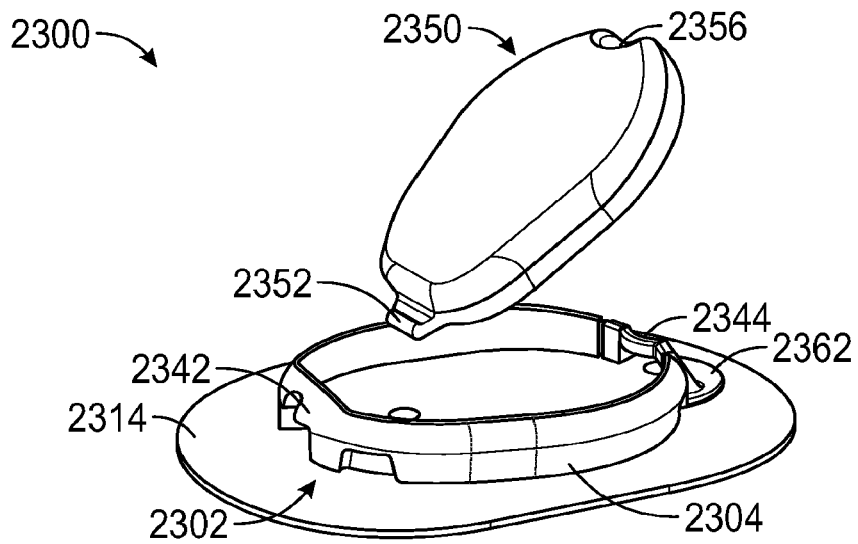
FIG. 23A is a perspective view of an example base and a sensor electronics module configured to be secured within the base, according to some embodiments.
Figure 23B:
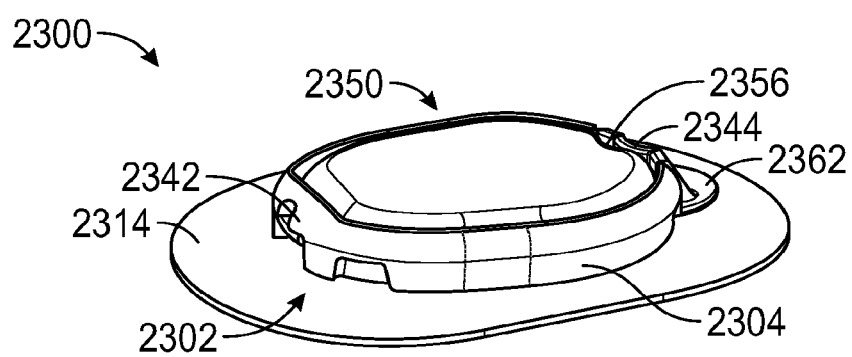
FIG. 23B is a perspective view of the sensor electronics module secured to the base of FIG. 23A.
Figure 23C:
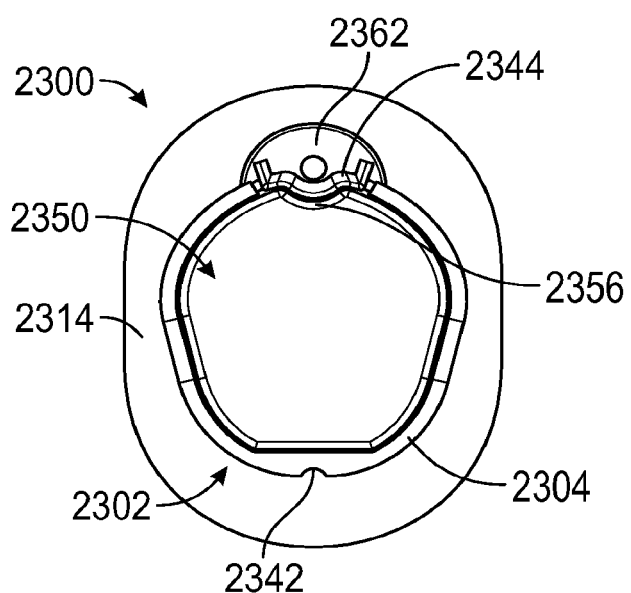
FIG. 23C is a plan view of the sensor electronics module secured to the base of FIG. 23A.

FIG. 23A is a perspective view of an example base 2302 and a sensor electronics module 2350 configured to be secured to base 2302, according to some embodiments. FIG. 23B is a perspective view of sensor electronics module 2350 secured to base 2350 of FIG. 23A. FIG. 23C is a plan view of sensor electronics module 2350 secured to base 2302 of FIG. 23A. Discussion follows with respect to FIGS. 23A-23C.

As shown in the figures, analyte sensor system 2300 comprises base 2302 and sensor electronics module 2350. Base 2302 can be configured to attach to the skin of the host, for example, utilizing an adhesive pad 2314, which can be disposed on a back surface of base 2302. In some embodiments, adhesive pad 2314 can include a releasable backing layer. Base 2302 can be adhered to the skin of the host by pressing base 2302 and adhesive pad 2314 onto the skin. Appropriate adhesive pads can be chosen and designed to stretch, elongate, conform to, and/or aerate the host's skin. Various configurations and arrangements can provide water resistant, waterproof, and/or hermetically sealed properties associated with the base/sensor electronics module embodiments described herein.

In some embodiments, base 2302 can be configured to physically and/or mechanically couple with sensor electronics module 2350 utilizing one or more retaining features. For example, base 2302 can have a raised perimeter 2304 configured to at least partially surround sensor electronics module 2350 as sensor electronics module 2350 is physically and/or mechanically coupled to base 2302, thereby guiding sensor electronics module 2350 into position during such physical and/or mechanical coupling.

To accomplish, affect and/or support such physical and/or mechanical coupling, base 2302 can further include a first retaining member 2342 and a second retaining member 2344, while sensor electronics module 2350 can further include a securement feature 2352 configured to mate with first retaining member 2342 and a retention feature 2356 configured to mate with second retaining member 2344.

First retaining member 2342 of base 2302 can comprise a recess, a ledge, a hook, a slit, or any other type of suitable retaining member. First retaining member 2342 can be disposed, for example, at a first end of base 2302. Second retaining member 2344 of base 2302 can comprise a snap, a hook, a button or any other suitable retaining member. Second retaining member 2344 can be disposed, for example, at a second end of base 2302 opposite the first end.

Securement feature 2352 of sensor electronics module 2350 can comprise a protrusion, a toe or any other type of suitable retention feature configured to mate with and be substantially immobilized by first retaining member 2342 of base 2302. Retention feature 2356 of sensor electronics module 2350 can comprise a recess, a ledge, a hook, a slit, or any other type of suitable retention feature configured to mate with, snap into and/or otherwise be substantially immobilized by second retaining member 2344 of base 2302.

For example, to secure sensor electronics module 2350 to base 2302, securement feature 2352 of sensor electronics module 2350 can be inserted into first retaining member 2342 of base 2302 such that sensor electronics module 2350 is disposed at an elevated angle with respect to base 2302, as shown in FIG. 23A. Sensor electronics module 2350 can then be pivoted toward base 2302, substantially about mated first retaining member 2342 and first retention feature 2352, until retention feature 2356 and second retaining member 2344 mate with one another (e.g., snap together into a retaining orientation), thereby securing sensor electronics module 2350 to base 2302, as shown in FIGS. 23B-23C.

In some embodiments, second retaining member 2344 is an integral part of base 2302 and is not configured to be separable from base 2302. In such embodiments, second retaining member 2344 can be configured to release retention feature 2356 by, for example, applying enough force to second retaining member 2344 to sufficiently deflect and thereby decouple it from second retention feature 2356. However, in other embodiments, similar to that described in more detail below in connection with at least FIGS. 24A-24D, second retaining member 2344 can be disposed on a frangible tab 2362 of base 2302 that is configured to separate from base 2302, thereby decoupling second retaining member 2344 from retention feature 2356 and decoupling sensor electronics module 2350 from base 2302.

While not shown in FIGS. 23A-23C, base 2302 can comprise at least a battery (e.g., battery 292 of FIG. 2) configured to power the analyte sensor and/or sensor electronics module 2350, a first sensor contact (e.g., similar to contact 2408 of FIG. 24A) and a second sensor contact (e.g., similar to contact 2410 of FIG. 24A), each electrically coupled to a respective terminal of the analyte sensor, and a first battery contact (e.g., similar to contact 2428 of FIG. 24A) and a second battery contact (e.g., similar to contact 2429 of FIG. 24A), each electrically coupled to a respective terminal of the battery.

While not shown in FIGS. 23A-23C, sensor electronics module 2350 can comprise a plurality of contacts (e.g., similar to contacts 2554 of FIG. 25A), which can include a first signal contact configured to make electrical contact with the first sensor contact, a second signal contact configured to make electrical contact with the second sensor contact, a first power contact configured to make electrical contact with the first battery contact, a second power contact configured to make electrical contact with the second battery contact (e.g., see FIGS. 24A-29C). Such first and second power contacts can be configured to receive power from the battery, while such first and second signal contacts can be configured to receive the sensor signal from the analyte sensor.

While not shown in FIGS. 23A-23C, analyte sensor assembly 2300 can further include a first sealing member (e.g., see FIGS. 24A-29C) configured to surround and seal each of the first and second sensor contacts, the first and second battery contacts, the first and second signal contacts and the first and second power contacts within a first cavity.

FIGS. 24A-27B illustrate several variations and/or embodiments of analyte sensor systems similar to that of FIGS. 23A-23C and are described in more detail below. Where appropriate, sensor electronics module 2350 and base 2302 of FIGS. 23A-23C can be considered to include some or all of the features as described in connection with any of at least FIGS. 24A-27B.

Figure 24B:
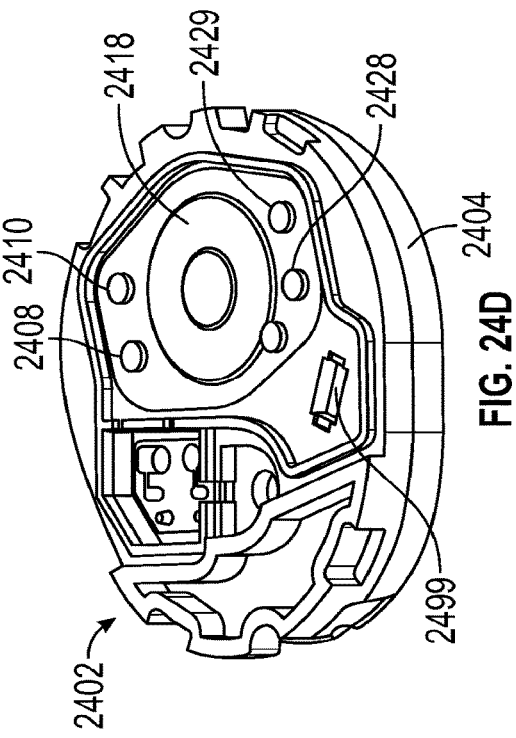
FIG. 24B is a perspective magnified view of a portion of the frangible retaining member of FIG. 24A retaining a sensor electronics module to the base, according to some embodiments.
Figure 24D:
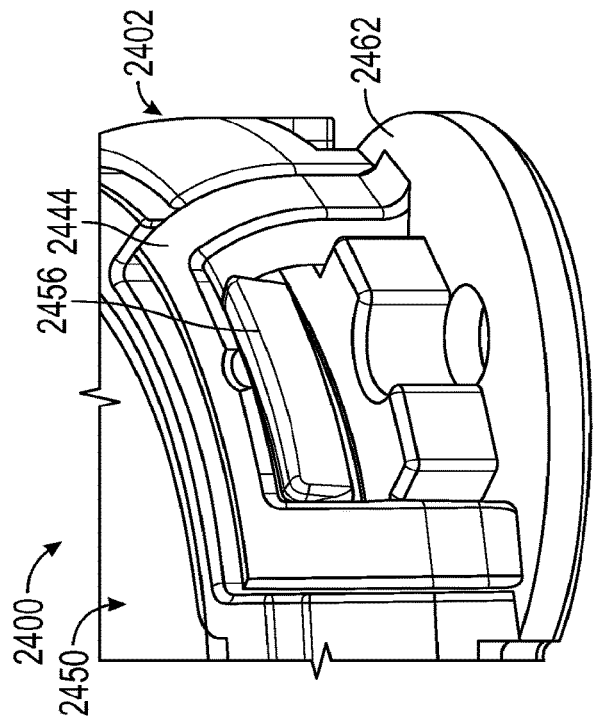
FIG. 24D is a perspective bottom view of the base of FIG. 24A.
Figure 24A:
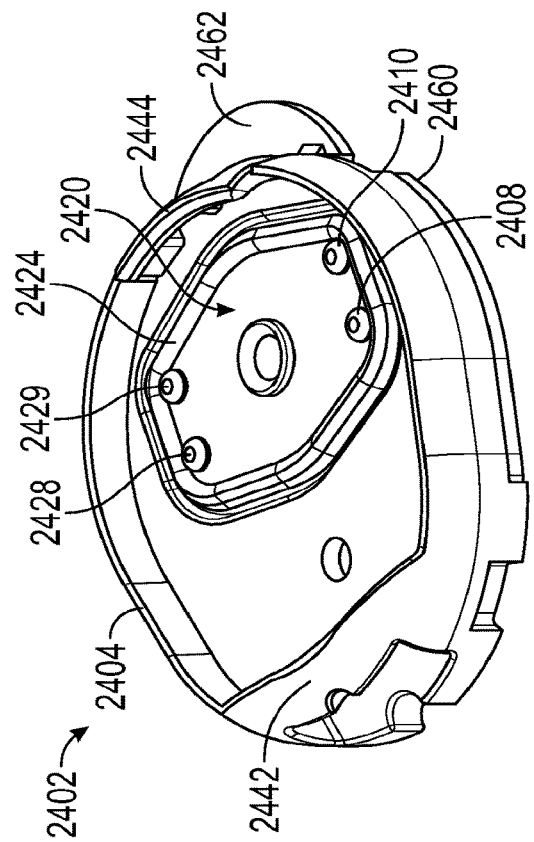
FIG. 24A is a perspective view of a base including a cover having a frangible retaining member, according to some embodiments.
Figure 24C:
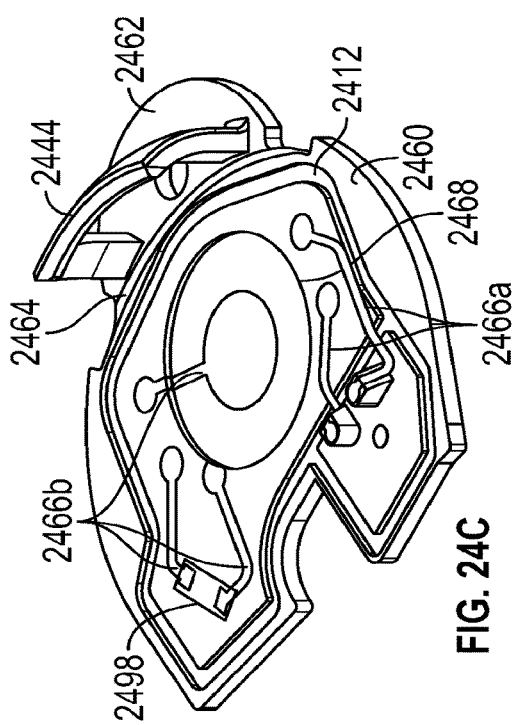
FIG. 24C is a perspective view of the cover of FIG. 24A.

FIG. 24A is a perspective view of a base 2402 including a cover 2460 having a frangible tab 2462, on which a retaining member 2444 is disposed, according to some embodiments. FIG. 24B is a perspective magnified view of frangible tab 2462 and retaining member 2444 of FIG. 24A shown retaining a sensor electronics module 2450 to base 2402. FIG. 24C is a perspective view of cover 2460 of FIG. 24A. And FIG. 24D is a perspective bottom view of base 2402. Discussion follows with respect to FIGS. 24A-24D.

An analyte sensor system 2400 can comprise base 2402 and sensor electronics module 2450. As illustrated in the figures, base 2402 includes a cover 2460 configured to be attached to and/or disposed on a bottom side of base 2402. Cover 2460 can comprise a plurality of conductive traces 2466, which can be formed utilizing any suitable process, for example, laser direct structuring (LDS) of cover 2460 or overmolding of a conductive elastomer. Conductive traces 2466 may be utilized to ultimately route electrical signals from the analyte sensor to sensor electronics module 2450 and/or power from a battery 2418 to sensor electronics module 2450 and to the analyte sensor. Cover 2460 may further include a recess 2468 configured to receive battery 2418. It is contemplated that fabricating traces 2466 onto cover 2460 instead of onto base 2402 may benefit manufacturability due to the small size of base 2402 and the manufacturing process of LDS traces.

Cover 2460 is further illustrated as having a frangible tab 2462 coupled to a main body of cover 2460 by a break line 2464. Frangible tab 2462 is configured to separate from cover 2460 along break line 2464 when frangible tab 2462 is sufficiently bent, flexed or otherwise deflected from its resting position shown in FIG. 24C. Cover 2460 can be secured to the bottom surface of base 2402 utilizing any suitable method, for example, snaps, adhesive, friction fittings, heat-staking, and/or laser, heat or ultra-sonic welding along weld line 2412. As shown in FIG. 24D, once secured to base 2402, cover 2460 may secure battery 2418 within a cavity in the bottom surface of base 2402.

As shown in FIG. 24A, base 2402 includes a sealing member 2424. A first sensor contact 2408 and a second sensor contact 2410 are disposed in sealing member 2424 and each is electrically coupled to a respective terminal of the analyte sensor (not shown in FIGS. 24A-24D) in base 2402 via at least some of conductive traces 2466*a* on cover 2460, as shown in FIG. 24C. For example, when cover 2460 is properly secured to a bottom side of base 2402, a first portion of conductive traces 2466a can be configured to contact first and second sensor contacts 2408, 2410, and a second portion of conductive traces 2466a (e.g., at the portions comprising raised post-like features illustrated in FIG. 24C) can be further configured to contact respective terminals or electrodes of the analyte sensor.

A first battery contact 2428 and a second battery contact 2429 are also disposed in sealing member 2424 and each is electrically coupled to a respective terminal of battery 2418 via at least some of conductive traces 2466b on cover 2460, also as shown in FIG. 24C. For example, when cover 2460 is properly secured to base 2402, a first portion of conductive traces 2466b can be configured to contact first and second battery contacts 2428, 2429, and a second portion of conductive traces 2466b (e.g., at the portions abutting and/or contacting cavity 2468 for receiving battery 2418 as illustrated in FIG. 24C) can be further configured to contact respective terminals or electrodes of battery 2418. In some embodiments, when cover 2460 is properly secured to base 2402, a current-limiting diode 2498 (see FIG. 24C) can be disposed in series between and electrically connecting at least two portions of conductive traces 2466b and can be configured to limit an amount of current that can be drawn from battery 2418, thereby increasing a useful life of battery 2418. Such a current-limiting diode 2498 can be disposed within a pocket 2499 in base 2402 (see FIG. 24D).

In some embodiments, as shown in at least FIG. 24A, first and second sensor contacts 2408, 2410 can be disposed a predetermined distance from first and second battery contacts 2428, 2429, which can substantially reduce signal interference compared to embodiments (see, e.g., FIGS. 25A-25B) where first and second sensor contacts 2508, 2510 and first and second battery contacts 2528, 2529 are disposed immediately adjacent to one another. The predetermined distance may be a distance sufficient to substantially reduce signal interference (e.g. leakage current, ionic contamination) from the sensor contacts and/or battery contacts. The predetermined distance may be determined by the resistance of the PCB board material and/or the solder mask over the contacts. In some embodiments, the predetermined distance is at least 1 millimeter. In some embodiments, the predetermined distance is at least 2 millimeters. In some embodiments, the predetermined distance is at least 3 millimeters. In some embodiments, the predetermined distance is at least 4 millimeters. In some embodiments, the predetermined distance is at least 5 millimeters. In some embodiments, the predetermined distance is at least 10 millimeters. In some embodiments, the predetermined distance is at least 15 millimeters. Contacts 2408, 2410, 2428, 2429 can comprise conductive elastomeric contacts (e.g. pucks), springs, tabs, posts, pogo pins, flat conductive pads or traces, or any other suitable conductive materials and/or structures.

While not shown in FIGS. 24A-24D, a facing (e.g., bottom) surface of sensor electronics module 2450 further comprises a plurality of contacts, which can include a first signal contact configured to make electrical contact with first sensor contact 2408, a second signal contact configured to make electrical contact with second sensor contact 2410, a first power contact configured to make electrical-contact with first battery contact 2428, and a second power contact configured to make electrical contact with second battery contact 2429. Accordingly, the first and second signal contacts on the bottom surface of sensor electronics module 2450 are configured to receive the sensor signal from the analyte sensor, while the first and second power contacts are configured to receive power from battery 2418 when sensor electronics module 2450 is properly secured to base 2402. Such contacts on sensor electronics module 2450 can comprise conductive elastomeric contacts (e.g. pucks), springs, tabs, posts, pogo pins, flat conductive pads or traces, or any other suitable conductive materials and/or structures.

When sensor electronics module 2450 is secured to base 2402, sealing member 2424 is configured to press against the facing surface of sensor electronics module 2450, thereby forming a first cavity 2420 between base 2402 and sensor electronics module 2450. Accordingly, single sealing member 2424 is configured to surround and create one continuous seal around each of first and second sensor contacts 2408, 2410, first and second battery contacts 2428, 2429, the first and second signal contacts and the first and second power contacts of sensor electronics module 2450 within first cavity 2420. Sealing member 2424 can, for example, be comprised of or include an overmolded component such as an overmolded gasket, an overmolded elastomeric feature, and/or an ultra-violet curable silicone that may be coupled to or assembled with base 2402.

In some embodiments, base 2402 can be configured to physically and/or mechanically couple with sensor electronics module 2450 utilizing one or more retaining features. For example, base 2402 can have a raised perimeter 2404 configured to at least partially surround sensor electronics module 2450 as sensor electronics module 2450 is physically and/or mechanically coupled to base 2402, thereby guiding sensor electronics module 2450 into position during such physical and/or mechanical coupling.

To accomplish, affect and/or support such physical and/or mechanical coupling, base 2402 can further include a first retaining member 2442 and a second retaining member 2444, while sensor electronics module 2450 can further include a first retention feature (not shown in FIGS. 24A-24D but having similar structure, function and location as securement feature 2352 of FIGS. 23A-23C) configured to mate with first retaining member 2442 and a retention feature 2456 configured to mate with second retaining member 2444. First and second retaining members 2442, 2444, the securement feature and retention feature 2456 can have similar or the same structure, function and locations as first and second retaining members 2342, 2344, securement feature 2352 and retention feature 2356 of FIGS. 23A-23C, respectively.

To secure sensor electronics module 2450 to base 2402, the first retention feature (not shown in FIGS. 24A-24D) of sensor electronics module 2450 can be inserted into first retaining member 2442 of base 2402 such that sensor electronics module 2450 is disposed at an elevated angle with respect to base 2402, similar to that shown in FIG. 23A. Sensor electronics module 2450 can then be pivoted toward base 2402, substantially about mated first retaining member 2442 and the first retention feature, until retention feature 2456 and second retaining member 2444 mate with one another, thereby securing sensor electronics module 2450 to base 2402 in an orientation as shown in FIGS. 23B-23C and 24B.

As illustrated in FIGS. 24A-24C, second retaining member 2444 of base 2402 can be disposed on frangible tab 2462 of cover 2460. Frangible tab 2462 is configured to separate from base 2402 along break line 2464. Accordingly, reusable sensor electronics module 2450 can be decoupled from disposable base 2402 by sufficiently bending, flexing or otherwise deflecting frangible tab 2462 from its resting position to decouple second retaining member 2444 from second retention feature 2456. Reusable sensor electronics module 2450, comprising relatively more expensive components than disposable base 2302, can then be secured and/or installed into a new disposable base 2402 having a fresh analyte sensor and charged battery 2418 in preparation for a subsequent sensor session for the host. Such an arrangement, wherein sensor electronics (e.g., including a wireless transceiver) are disposed in a mechanically separable enclosure or module from the analyte sensor and/or battery, can advantageously allow for replacement of inexpensive components of analyte sensor system 2400 (e.g., base 2402) and reuse of relatively more expensive components of analyte sensor system 2400 (e.g., sensor electronics module 2450).

Figure 25A:
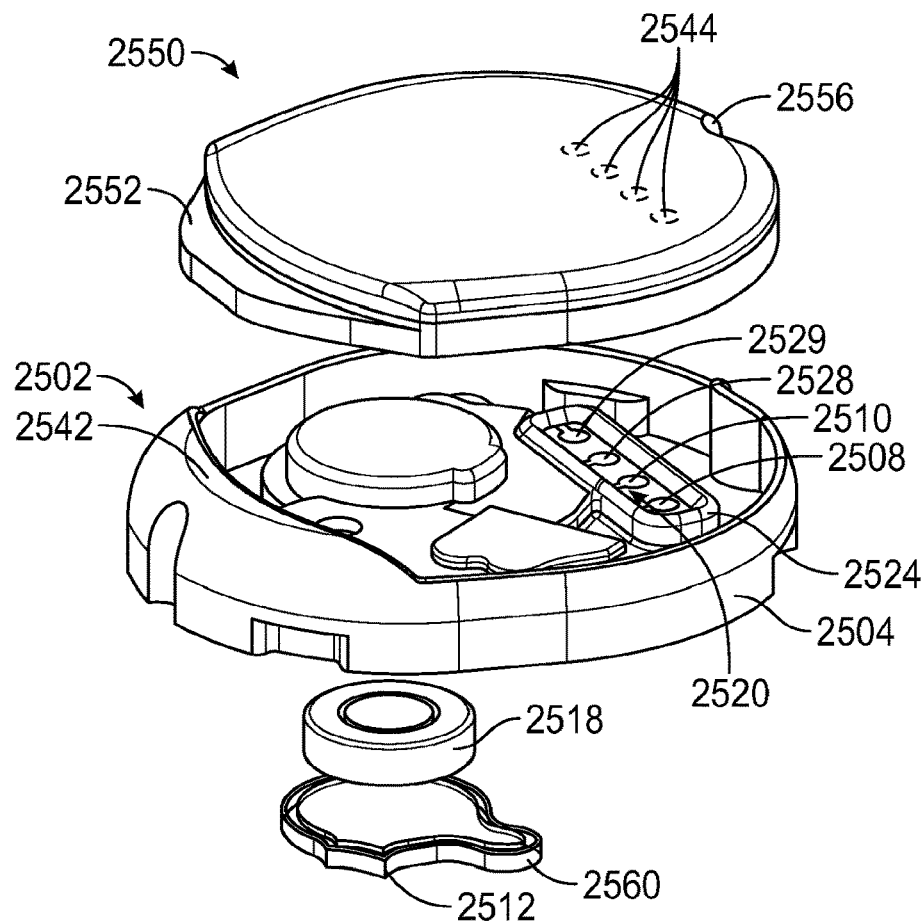
FIG. 25A is an exploded perspective view of an example base and a sensor electronics module configured to be secured within the base, according to some embodiments.
Figure 25B:
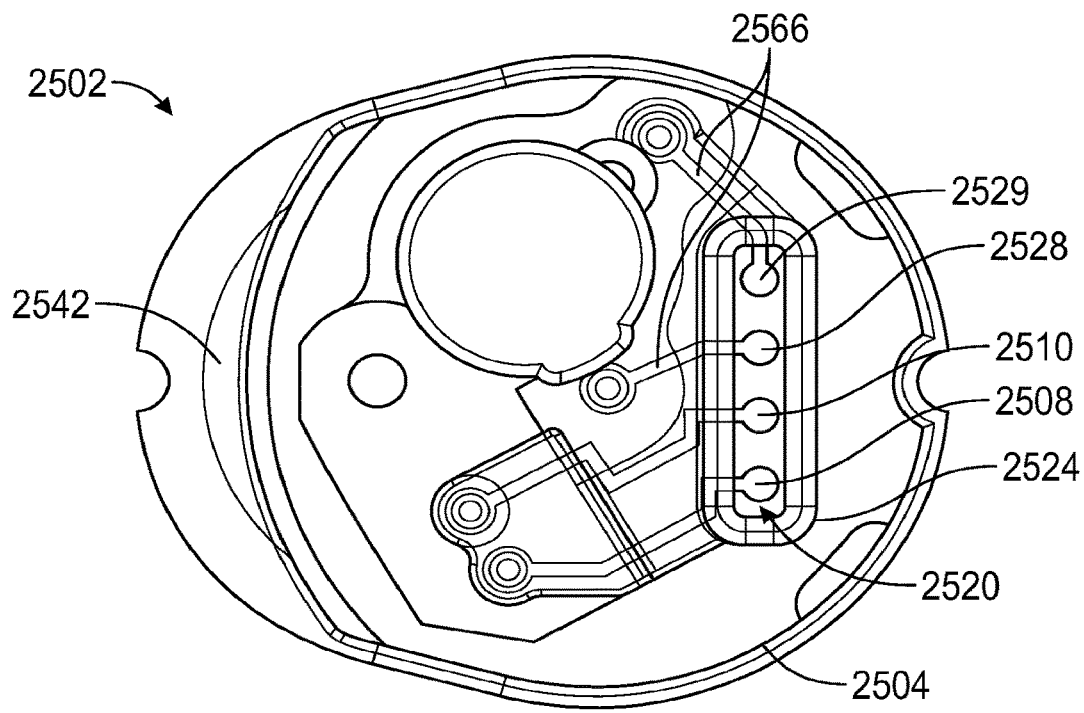
FIG. 25B is a plan view of the base of FIG. 25A.

FIG. 25A is an exploded perspective view of an example base 2502 and a sensor electronics module 2550 configured to be secured within base 2502, according to some embodiments. FIG. 25B is a plan view of base 2502 of FIG. 25A. Discussion follows with respect to FIGS. 25A-25B.

An analyte sensor system 2500 can comprise base 2502 and sensor electronics module 2550. As with base 2402 of FIGS. 24A-24D, base 2502 is configured to receive a battery 2518 within a cavity in a bottom surface of base 2502. Base 2502 can also include a cover 2560 configured to be attached to and/or disposed on a bottom side of base 2502. However, unlike cover 2460 of FIGS. 24A-24D, cover 2560 may not cover a substantial portion of the bottom surface of base 2502 but may instead be shaped and sized to secure battery 2518 within base 2502. Cover 2560 can be secured to the bottom surface of base 2502 utilizing any suitable method, for example, snaps, adhesive, friction fittings, heat-staking, and/or laser, heat or ultra-sonic welding along weld line 2512.

As shown in FIG. 25B, base 2502 can comprise a plurality of conductive traces 2566, which can be formed utilizing any suitable process, for example, laser direct structuring (LDS) of base 2502 or overmolding of a conductive elastomer. Conductive traces 2566 may be utilized to ultimately route electrical signals from the analyte sensor to sensor electronics module 2550 and/or power from battery 2518 to sensor electronics module 2550 and to the analyte sensor. It is contemplated that fabricating traces 2566 directly onto base 2502 may reduce part count and overall sensor electronics module size and/or volume.

Base 2502 further includes a first sensor contact 2508 and a second sensor contact 2510, each electrically coupled to a respective terminal of the analyte sensor in base 2502 via at least some of conductive traces 2566. Base 2502 further includes a first battery contact 2528 and a second battery contact 2529, each electrically coupled to a respective terminal of battery 2518 via at least some other of conductive traces 2566. As shown in the figures, contacts 2508, 2510, 2528, 2529 can be disposed immediately adjacent to one another (e.g., disposed along a straight or curvilinear line) and may comprise conductive elastomeric contacts (e.g. pucks), springs, tabs, posts, pogo pins, flat conductive pads or traces, or any other suitable conductive materials and/or structures.

Base 2502 further includes a sealing member 2524, which can extend over, and thereby seal, conductive traces 2566 from moisture ingress and which also surrounds and creates a single continuous seal around contacts 2508, 2510, 2528, 2529 on base 2302. Sealing member 2524 can, for example, include an overmolded component such as an overmolded gasket, an overmolded elastomeric feature, and/or an ultraviolet curable silicone that may be coupled to or assembled with base 2502.

A facing (e.g., bottom) surface of sensor electronics module 2550 further comprises a plurality of contacts 2544, which can include a first signal contact configured to make electrical contact with first sensor contact 2508, a second signal contact configured to make electrical contact with second sensor contact 2510, a first power contact configured to make electrical contact with first battery contact 2528, and a second power contact configured to make electrical contact with second battery contact 2529. Accordingly, the first and second signal contacts on the bottom surface of sensor electronics module 2550 are configured to receive the sensor signal from the analyte sensor, while the first and second power contacts are configured to receive power from battery 2518 when sensor electronics module 2550 is properly secured to base 2502. Such contacts 2554 on sensor electronics module 2550 can comprise conductive elastomeric contacts (e.g. pucks), springs, tabs, posts, pogo pins, flat conductive pads or traces, or any other suitable conductive materials and/or structures.

When sensor electronics module 2550 is secured to base 2502, sealing member 2524 is configured to press against the facing surface of sensor electronics module 2550, thereby forming a first cavity 2520 between base 2502 and sensor electronics module 2550. Accordingly, when sensor electronics module 2550 is secured to base 2502, sealing member 2524 is configured to surround and create a continuous seal around each of first and second sensor contacts 2508, 2510, first and second battery contacts 2528, 2529, the first and second signal contacts and the first and second power contacts of sensor electronics module 2550.

In some embodiments, base 2502 can be configured to physically and/or mechanically couple with sensor electronics module 2550 utilizing one or more retaining features. For example, base 2502 can have a raised perimeter 2504 configured to at least partially surround sensor electronics module 2550 as sensor electronics module 2550 is physically and/or mechanically coupled to base 2502, thereby guiding sensor electronics module 2550 into position during such physical and/or mechanical coupling.

To accomplish, affect and/or support such physical and/or mechanical coupling, base 2502 can further include a first retaining member 2542 and a second retaining member (not shown in FIGS. 25A-25B but having similar structure, function and location as second retaining member 2344, 2444 of FIGS. 23A-24D), while sensor electronics module 2550 can further include a securement feature 2552 configured to mate with first retaining member 2542 and a retention feature 2556 configured to mate with the second retaining member. First and second retaining members 2542, securement feature 2552, and retention feature 2556 can have similar or the same structure, function and locations as first and second retaining members 2342, 2344, securement feature 2352 and retention feature 2356 of FIGS. 23A-23C, respectively, with the exception that securement feature 2552 may be wider than securement feature 2352 of FIGS. 23A-23C.

While not shown in FIGS. 25A-25B, the second retaining member can be disposed on base 2502, for example as described in connection with FIGS. 23A-23C, rather than on a cover, for example as described in connection with FIGS. 24A-24D. In some embodiments, the second retaining member is an integral part of base 2502 and is not configured to be separable from base 2302. In some other embodiments, base 2502 may comprise a frangible tab similar to that previously described in connection with at least FIGS. 24A-24D and the second retaining member can be disposed on the frangible tab. Sensor electronics module 2550 can be secured to and decoupled from base 2502 substantially as previously described in connection with at least FIGS. 23A-24D.

Figure 26A:
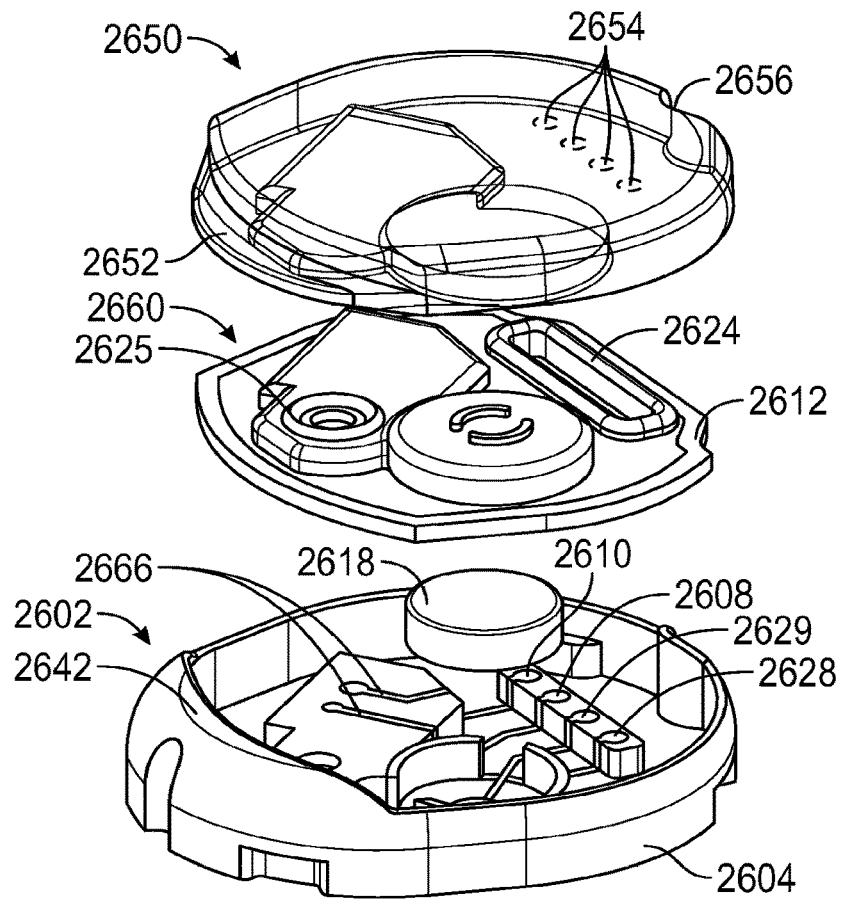
FIG. 26A is an exploded perspective view of an example base and a sensor electronics module configured to be secured within the base, according to some embodiments.
Figure 26B:
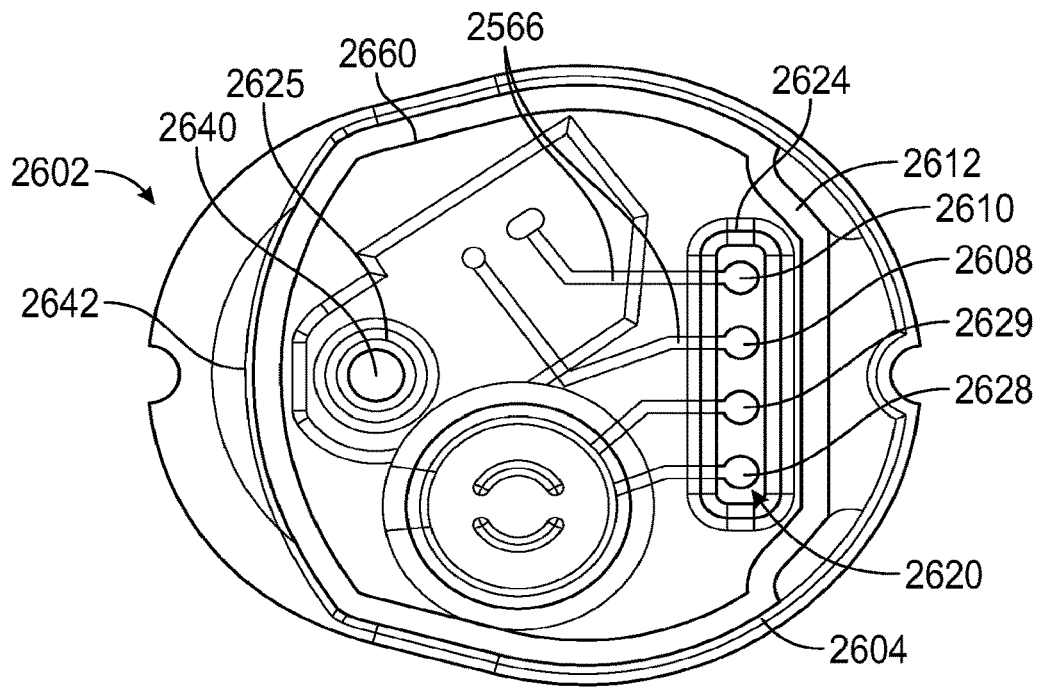
FIG. 26B is a plan view of the base of FIG. 26A.

FIG. 26A is an exploded perspective view of an example base 2602 and a sensor electronics module 2650 configured to be secured within base 2602, according to some embodiments. FIG. 26B is a plan view of base 2602 of FIG. 26A. Discussion follows with respect to FIGS. 26A-26B.

An analyte sensor system 2600 can comprise base 2602 and sensor electronics module 2650. Base 2602 is configured to receive a battery 2618 within a cavity in a top surface of base 2602. As shown in FIG. 26B, base 2602 can comprise a plurality of conductive traces 2666, which can be formed utilizing any suitable process, for example, laser direct structuring (LDS) of base 2602 or overmolding of a conductive elastomer. Conductive traces 2666 may be utilized to ultimately route electrical signals from the analyte sensor to sensor electronics module 2650 and/or power from battery 2618 to sensor electronics module 2650 and/or to the analyte sensor.

Base 2602 further includes a first sensor contact 2608 and a second sensor contact 2610, each electrically coupled to a respective terminal of the analyte sensor in base 2602 via at least some of conductive traces 2666. Base 2602 further includes a first battery contact 2628 and a second battery contact 2629, each electrically coupled to a respective terminal of battery 2618 via at least some other of conductive traces 2666. In some embodiments, at least one terminal of battery 2618 can be a radial conductive connection comprising a conductive material disposed on a sidewall of a portion of base 2602 configured to hold battery 2618. Such a radial conductive terminal can be configured to both physically secure battery 2618 to base 2602 as well as provide electrical connection from one battery terminal to one of battery contacts 2628, 2629.

As shown in the figures and similar to embodiments illustrated by FIGS. 25A-25B, contacts 2608, 2610, 2628, 2629 can be disposed immediately adjacent to one another (e.g., disposed along a straight or curvilinear line) and may comprise conductive elastomeric contacts (e.g. pucks), springs, tabs, posts, pogo pins, flat conductive pads or traces, or any other suitable conductive materials and/or structures.

Base 2602 further includes a cover 2660 comprising a sealing member 2624, which can extend over and thereby seal conductive traces 2666 and battery 2618 and which also surrounds and creates a continuous seal around each of contacts 2608, 2610, 2628, 2629 on base 2302. Cover 2660 and/or sealing member 2624 can, for example, include an overmolded component such as an overmolded gasket, an overmolded elastomeric feature, and/or an ultra-violet curable silicone that may be coupled to a surface of base 2602 utilizing any suitable method, for example adhesive, heat-staking, and/or laser, heat or ultra-sonic welding along weld line 2612. Because cover 2660 can also extend over a through-hole 2640 of base 2602, cover 2660 can also comprise a second seal 2625 surrounding through-hole 2640. Due to cover 2660 extending over substantially all or a significant majority of a top surface of base 2602, cover 2660 may act as an insulating cover for all or at least some of the components of base 2602 disposed thereunder.

A facing (e.g., bottom) surface of sensor electronics module 2650 further comprises a plurality of contacts 2654, which can include a first signal contact configured to make electrical contact with first sensor contact 2608, a second signal contact configured to make electrical contact with second sensor contact 2610, a first power contact configured to make electrical contact with first battery contact 2628, and a second power contact configured to make electrical contact with second battery contact 2629. Accordingly, the first and second signal contacts on the bottom surface of sensor electronics module 2650 are configured to receive the sensor signal from the analyte sensor, while the first and second power contacts are configured to receive power from battery 2618 when sensor electronics module 2650 is properly secured to base 2602. Such contacts on sensor electronics module 2650 can comprise conductive elastomeric contacts (e.g. pucks), springs, tabs, posts, pogo pins, flat conductive pads or traces, or any other suitable conductive materials and/or structures.

When sensor electronics module 2650 is secured to base 2602, portions of sealing member 2624 on cover 2660 and around contacts 2608, 2610, 2628, 2629 are configured to press against the facing surface of sensor electronics module 2650, thereby forming a first cavity 2620 between base 2602 and sensor electronics module 2650. Accordingly, when sensor electronics module 2650 is secured to base 2602, sealing member 2624 is configured to surround and create a continuous seal around first and second sensor contacts 2608, 2610, first and second battery contacts 2628, 2629, and the plurality of contacts 2654 (e.g., the first and second signal contacts and the first and second power contacts) of sensor electronics module 2650.

In some embodiments, base 2602 can be configured to physically and/or mechanically couple with sensor electronics module 2650 utilizing one or more retaining features. For example, base 2602 can have a raised perimeter 2604 configured to at least partially surround sensor electronics module 2650 as sensor electronics module 2650 is physically and/or mechanically coupled to base 2602, thereby guiding sensor electronics module 2650 into position during such physical and/or mechanical coupling.

To accomplish, affect and/or support such physical and/or mechanical coupling, base 2602 can further include a first retaining member 2642 and a second retaining member (not shown in FIGS. 26A-26B but having similar structure, function and location as second retaining member 2344 (FIG. 23A), 2444 (FIG. 24D), while sensor electronics module 2650 can further include a securement feature 2652 configured to mate with first retaining member 2642 and a retention feature 2656 configured to mate with the second retaining member. First and second retaining members 2642, securement feature 2652 and retention feature 2656 can have similar or the same structure, function and locations as first and second retaining members 2342, 2344, securement feature 2352, and retention feature 2356 of FIGS. 23A-23C, respectively, with the exception that securement feature 2652 may be wider than securement feature 2352 of FIGS. 23A-23C, similar to securement feature 2552 of FIGS. 25A-25B, but also having a substantially rounded front edge.

While not shown in FIGS. 26A-26B, the second retaining member can be disposed on base 2602, for example as described in connection with FIGS. 23A-23C and 25A-25B, rather than on a cover, for example as described in connection with FIGS. 24A-24D. In some embodiments, the second retaining member is an integral part of base 2602 and is not configured to be separable from base 2302. In some other embodiments, base 2602 may comprise a frangible tab similar to that previously described in connection with at least FIGS. 24A-24D and the second retaining member can be disposed on the frangible tab. Sensor electronics module 2650 can be secured to and decoupled from base 2602 substantially as previously described in connection with at least FIGS. 23A-24D.

Figure 27A:
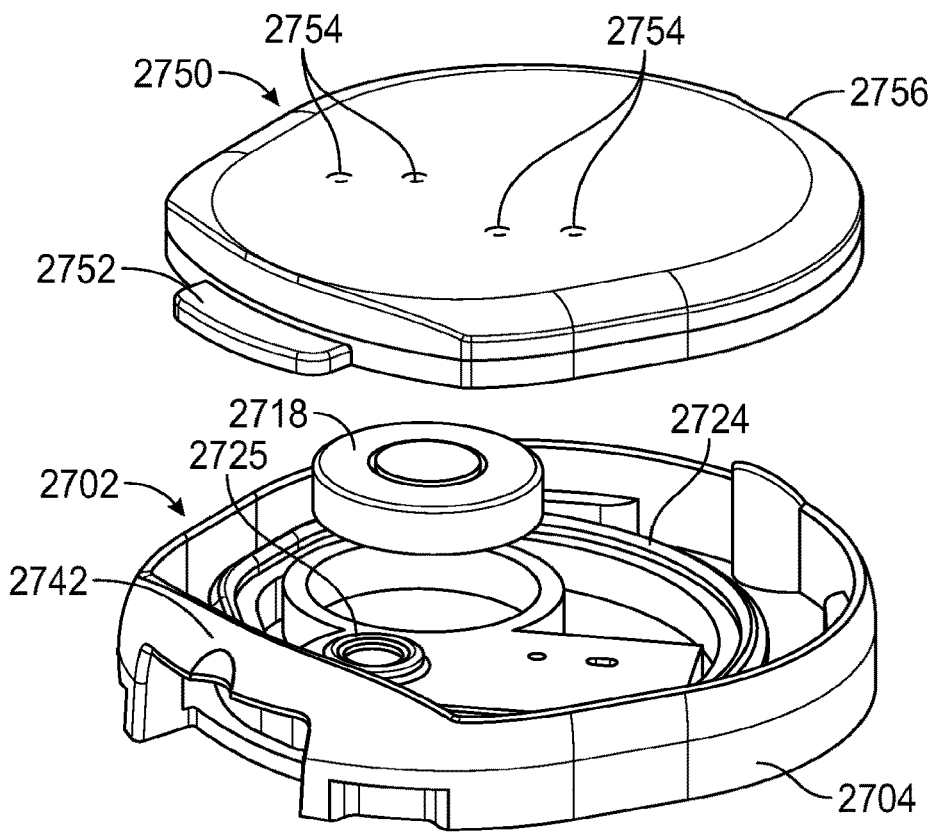
FIG. 27A is an exploded perspective view of an example base and a sensor electronics module configured to be secured within the base, according to some embodiments.
Figure 27B:
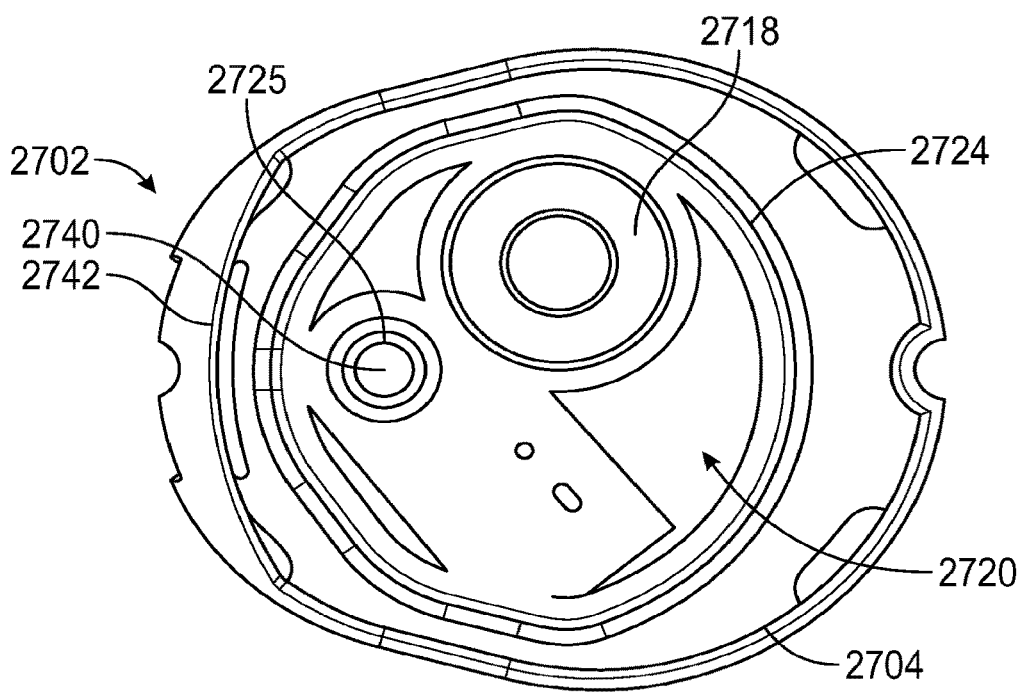
FIG. 27B is a plan view of the base of FIG. 27A.

FIG. 27A is an exploded perspective view of an example base 2702 and a sensor electronics module 2750 configured to be secured within base 2702, according to some embodiments. FIG. 27B is a plan view of base 2702 of FIG. 27A. Discussion follows with respect to FIGS. 27A-27B.

An analyte sensor system 2700 can comprise base 2702 and sensor electronics module 2750. While several features are not shown in FIGS. 27A-27B, base 2702 and sensor electronics module 2750 can comprise substantially the same features as previously described for base 2602 and sensor electronics module 2650 in connection with FIGS. 26A-26B with the following differences.

Securement feature 2752 of sensor electronics module 2750, configured to mate with first retaining member 2742 of base 2702, can comprise a protrusion or "toe" similar to that previously described for first retaining member 2342 of FIGS. 23A-23C. In addition, rather than first sealing member 2724 covering a substantial portion of a top surface of base 2702, first sealing member 2724 may instead form a continuous circumferential seal that extends around a battery 2718, disposed in a cavity in a top surface of base 2702, and each of the contacts on base 2302. A separate, second sealing member 2725 can surround a through-hole 2740 in base 2702. Sealing members 2724, 2725 can, for example, include overmolded components such as overmolded gaskets, overmolded elastomeric features, and/or ultra-violet curable silicone that may be coupled to a surface of base 2702 utilizing any suitable method. In addition, in some embodiments, power and signal contacts 2754 on an underside of sensor electronics module 2750 may directly contact respective terminals on battery 2718 and respective leads of the analyte sensor (not shown in FIGS. 27A-27B), rather than being connected via a plurality of conductive traces at locations removed from such terminals and leads.

FIGS. 28A-29C illustrate several variations and/or embodiments of analyte sensor systems similar to that of at least FIGS. 23A-27B, however, providing electrical contacts on a first retention feature of a sensor electronics module, and are described in more detail below.

Figure 28A:
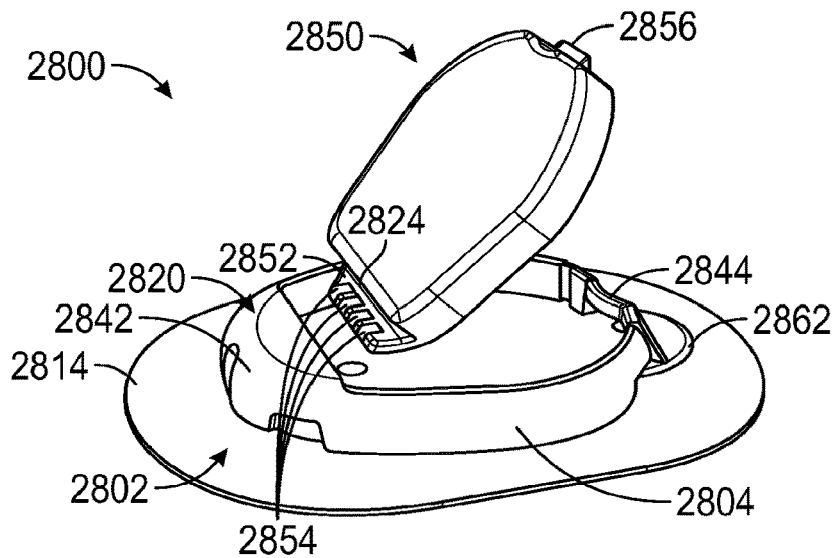
FIG. 28A is a perspective view of an example base and a sensor electronics module configured to be secured within the base, according to some embodiments.
Figure 28B:
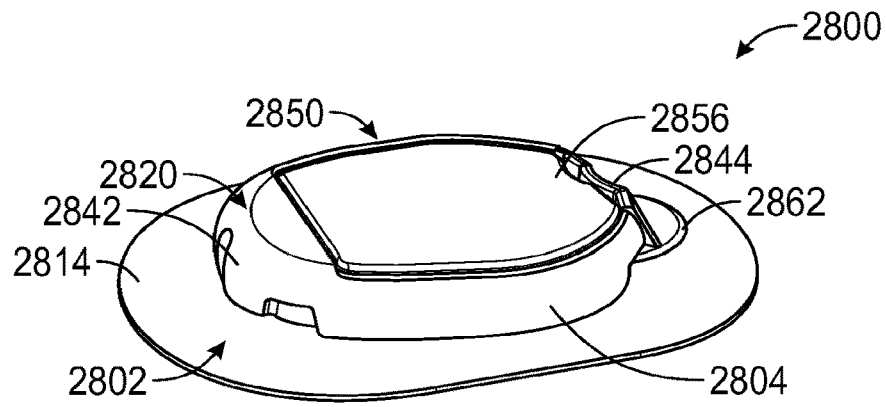
FIG. 28B is a perspective view of the sensor electronics module secured to the base of FIG. 28A.
Figure 28C:
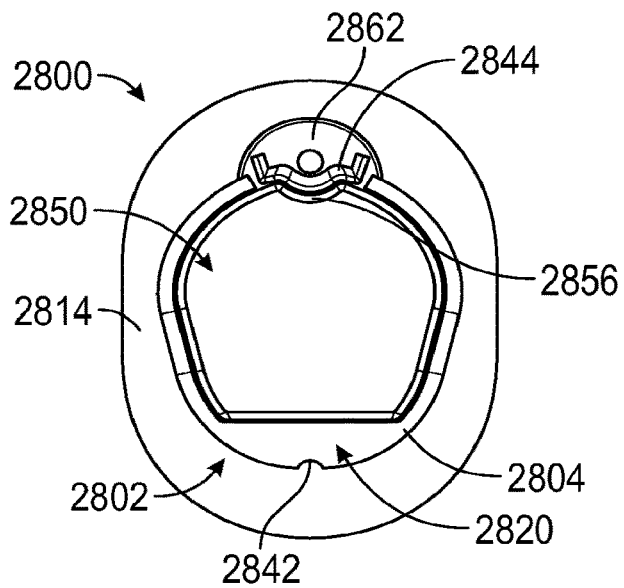
FIG. 28C is a plan view of the sensor electronics module secured to the base of FIG. 28A.

FIG. 28A is a perspective view of an example base 2802 and a sensor electronics module 2850 configured to be secured within base 2802, according to some embodiments. FIG. 28B is a perspective view of sensor electronics module 2850 secured to base 2802 of FIG. 28A. FIG. 28C is a plan view of sensor electronics module 2850 secured to base 2802 of FIG. 28A.

As shown in the figures, analyte sensor system 2800 comprises base 2802 and sensor electronics module 2850. Base 2802 can be configured to attach to the skin of the host, for example, utilizing an adhesive pad 2814, which can be disposed on a back surface of base 2802. Adhesive pad 2814 can have substantially similar features and function as previously described for adhesive pad 2314 of FIGS. 23A-23C.

Base 2802 can be configured to physically and/or mechanically couple with sensor electronics module 2850 utilizing one or more retaining features. For example, base 2802 can have a raised perimeter 2804 configured to at least partially surround sensor electronics module 2850 as sensor electronics module 2850 is physically and/or mechanically coupled to base 2802, thereby guiding sensor electronics module 2850 into position during such physical and/or mechanical coupling.

To accomplish, affect and/or support such physical and/or mechanical coupling, base 2802 can further include a first retaining member 2842 and a second retaining member 2844, while sensor electronics module 2850 can further include a securement feature 2852 configured to mate with first retaining member 2842 and a retention feature 2856 configured to mate with second retaining member 2844.

First retaining member 2842 of base 2802 can comprise a cap or hood and can be disposed, for example, at a first end of base 2802. Second retaining member 2844 of base 2802 can comprise a snap, a hook, a button or any other suitable retaining member. Second retaining member 2844 can be disposed, for example, at a second end of base 2802 opposite the first end.

Securement feature 2852 of sensor electronics module 2850 can comprise a protrusion, a toe or any other type of suitable retention feature configured to mate with and be substantially immobilized by first retaining member 2842 of base 2802. Retention feature 2856 of sensor electronics module 2850 can comprise a recess, a ledge, a hook, a slit, or any other type of suitable retention feature configured to mate with, snap into and/or otherwise be substantially immobilized by second retaining member 2844 of base 2802.

Sensor electronics module 2850 can comprise a plurality of contacts 2854, which can include first and second signal contacts and first and second power contacts, each disposed on first retention feature 2852. Such first and second power contacts can be configured to receive power from a battery (not shown in FIGS. 28A-28B) disposed within base 2802, while such first and second signal contacts can be configured to receive the sensor signal from the analyte sensor. Accordingly, securement feature 2852 is configured to secure sensor electronics module 2850 to base 2802 and also provide electrical connections therebetween, utilizing the same structure for both, disparate functions.

Sensor electronics module 2850 can further include a first sealing member 2824 configured to surround and seal each of the first and second sensor contacts and the first and second battery contacts within a first cavity 2820 located within the cap or hood formed by first retaining member 2842 of base 2802. For example, first sealing member 2824 can be a radial or slot seal disposed around a circumference of securement feature 2852 and configured to press against an inner surface of the cap or hood formed by first retaining member 2842 and/or of base 2802 when sensor electronics module 2850 is properly secured to base 2802.

While not shown in FIGS. 28A-28C, base 2802 further comprises a plurality of electrical contacts (e.g., see contacts 2908, 2910, 2928, 2929 of FIGS. 29A-29C) disposed within the cap or hood formed by first retaining member 2842 of base 2802, for example including first and second sensor contacts, each electrically coupled to a respective terminal of the analyte sensor, and first and second battery contacts, each electrically coupled to a respective terminal of the battery (e.g., see battery 2918 of FIGS. 29A-29C). The first and second signal contacts and the first and second power contacts (e.g., together contacts 2954) of sensor electronics module 2850 are configured to electrically contact the first and second sensor contacts and the first and second battery contacts (e.g., see contacts 2908, 2910, 2928, 2929 of FIGS. 29A-29C) of base 2802, respectively, when sensor electronics module 2850 is properly secured to base 2802.

To secure sensor electronics module 2850 to base 2802, securement feature 2852 of sensor electronics module 2850 can be inserted into first retaining member 2842 of base 2802 such that sensor electronics module 2850 is disposed at an elevated angle with respect to base 2802, as shown in FIG. 28A. Sensor electronics module 2850 can then be pivoted toward base 2802, substantially about mated first retaining member 2842 and securement feature 2852, until retention feature 2856 and second retaining member 2844 mate with one another (e.g., snap together into a retaining orientation), thereby securing sensor electronics module 2850 to base 2802, as shown in FIGS. 28B-28C. In some embodiments, a force required to secure sensor electronics module 2850 to base 2802 and, thereby, seal contacts 2908, 2910, 2928, 2929 within first cavity 2820 can be less than for some other toe-in concepts (see, e.g., FIGS. 23A-27B) at least because first sealing member 2824 is disposed around a circumference of securement feature 2852, rather than on a portion of base 2802 or on a cover that is laterally spaced from securement feature 2852.

In some embodiments, second retaining member 2844 is an integral part of base 2802 and is not configured to be separable from base 2802. In such embodiments, second retaining member 2844 can be configured to release retention feature 2856 by, for example, applying enough force to second retaining member 2844 to sufficiently deflect and thereby decouple it from second retention feature 2856. However, in other embodiments, similar to those previously described in connection with at least FIGS. 23A-24D, second retaining member 2844 can be disposed on a frangible tab 2862 of base 2802 that is configured to separate from base 2802, thereby decoupling second retaining member 2844 from retention feature 2856 and so decoupling sensor electronics module 2850 from base 2802.

FIGS. 29A-29C illustrate a variation and/or embodiment of an analyte sensor system similar to that of FIGS. 28A-28C, which is described in more detail below. FIG. 29A is an exploded perspective view of an example base 2902 and a sensor electronics module 2950 configured to be secured within base 2902, according to some embodiments. FIG. 29B is a perspective view of portions of base 2902 of FIG. 29A. FIG. 29C is a perspective view of a bottom of base 2902 of FIG. 29A. Discussion follows with respect to FIGS. 29A-29C.

An analyte sensor system 2900 can comprise base 2902 and sensor electronics module 2950. Base 2902 is configured to receive a battery 2918 within a cavity in a bottom surface of base 2902. Base 2902 can also include a cover 2960 (shown as transparent for illustrative purposes) configured to be attached to and/or disposed on a bottom side of base 2902 and shaped and sized to secure battery 2918 within base 2902. Cover 2960 can be secured to the bottom surface of base 2902 utilizing any suitable method, for example, snaps, adhesive, friction fittings, heat-staking, and/or laser, heat or ultra-sonic welding along weld line 2912.

As shown in FIG. 29B, base 2902 can comprise a plurality of conductive traces 2966, which can be formed utilizing any suitable process, for example, laser direct structuring (LDS) of base 2902 or overmolding of a conductive elastomer. Conductive traces 2966 may be utilized to ultimately route electrical signals from the analyte sensor to sensor electronics module 2950 and/or power from battery 2918 to sensor electronics module 2950 and/or to the analyte sensor. As illustrated in at least FIG. 29B, according to some embodiments, those of conductive traces 2966 utilized to ultimately route electrical signals from the analyte sensor to sensor electronics module 2950 can be disposed at least a predetermined distance away from those of conductive traces 2966 utilized to ultimately route power from battery 2918 to sensor electronics module 2950 and/or to the analyte sensor. At least one advantage of such a disposition of conductive traces 2966 is reduced signal interference between the electrical signal traces and the power traces. Base 2902 further includes a first plurality of conductive contacts 2937, each in electrical contact with a respective one of conductive traces 2966. Conductive contacts 2937 can comprise conductive elastomeric contacts (e.g. pucks), springs, tabs, posts, pogo pins, flat conductive pads or traces, or any other suitable conductive materials and/or structures. A sealing member 2925 (shown as transparent for illustrative purposes in FIG. 29B) is disposed over conductive traces 2966 and around at least a portion of conductive contacts 2937. Sealing member 2925 can, for example, include an overmolded component such as an overmolded gasket, an overmolded elastomeric feature, and/or an ultraviolet curable silicone that may be coupled to or assembled with base 2902.

Base 2902 further includes a first retaining member 2942, which, similar to first retaining member 2842 of FIGS. 28A-28B, can comprise a cap or hood and can be disposed, for example, at a first end of base 2902. Furthermore, in some instances, first retaining member 2942 can be a separate component apart from base 2902, as shown in FIG. 29A. As shown in FIG. 29B, first retaining member 2942 further comprises a second plurality of conductive contacts 2938, each configured to electrically contact a respective one of conductive contacts 2937 of base 2902 when first retaining member 2942 is secured to base 2902, for example by adhesive, welding or any other suitable method. First retaining member 2942 further comprises a second plurality of conductive traces 2967, which, like conductive traces 2966 of base 2902, can be formed utilizing any suitable process, for example, laser direct structuring (LDS) of first retaining member 2942 or overmolding of a conductive elastomer. First retaining member 2942 further comprises a sensor contact 2908, a second sensor contact 2910, a first battery contact 2928 and a second battery contact 2929, each electrically coupled to a respective one of conductive contacts 2938 via a respective one of conductive traces 2967. As shown in the figures, contacts 2908, 2910, 2928, 2929 can be disposed immediately adjacent to one another (e.g., disposed along a straight or curvilinear line) and may comprise conductive elastomeric contacts (e.g. pucks), springs, tabs, posts, pogo pins, flat conductive pads or traces, or any other suitable conductive materials and/or structures.

First retaining member 2942 further includes a sealing member 2924 (e.g., disposed on an inner surface of first retaining member 2942), which can extend over and thereby seal conductive traces 2967, around each of conductive contacts 2937, and which also surrounds and creates one continuous seal around contacts 2908, 2910, 2928, 2929. Sealing member 2924 can, for example, be composed of or include an overmolded component such as an overmolded gasket, an overmolded elastomeric feature, and/or an ultraviolet curable silicone that may be coupled to or assembled with first retaining member 2942.

Sensor electronics module 2950 includes a securement feature 2952 configured to mate with first retaining member 2942. Securement feature 2952 comprises a plurality of contacts 2954, which can include a first signal contact configured to make electrical contact with first sensor contact 2908, a second signal contact configured to make electrical contact with second sensor contact 2910, a first power contact configured to make electrical contact with first battery contact 2928, and a second power contact configured to make electrical contact with second battery contact 2929. Accordingly, the first and second signal contacts on securement feature 2952 of sensor electronics module 2950 are configured to receive the sensor signal from the analyte sensor, while the first and second power contacts are configured to receive power from battery 2918 when sensor electronics module 2950 is properly secured to base 2902. Such contacts 2954 on securement feature 2952 of sensor electronics module 2950 can comprise conductive elastomeric contacts (e.g. pucks), springs, tabs, posts, pogo pins, flat conductive pads or traces, or any other suitable conductive materials and/or structures. It is contemplated that including signal contacts 2954 into securement feature 2952 can increase space efficiency of sensor electronics module 2950 and minimize the overall height and/or area of sensor electronics module 2950.

When sensor electronics module 2950 is secured to base 2902, sealing member 2924 is configured to press against the facing surface of securement feature 2952 of sensor electronics module 2950, thereby forming a first cavity 2920 between base 2902 (e.g., first retaining member 2942) and sensor electronics module 2950 (e.g., first retention feature 2952). Accordingly, when sensor electronics module 2950 is secured to base 2902, sealing member 2924 is configured to surround and create a continuous seal around first and second sensor contacts 2908, 2910, first and second battery contacts 2928, 2929, the first and second signal contacts and the first and second power contacts of sensor electronics module 2950 (e.g., contacts 2854).

Base 2902 can be configured to physically and/or mechanically couple with sensor electronics module 2950 utilizing one or more retaining features. For example, base 2902 can have a raised perimeter 2904 configured to at least partially surround sensor electronics module 2950 as sensor electronics module 2950 is physically and/or mechanically coupled to base 2902, thereby guiding sensor electronics module 2950 into position during such physical and/or mechanical coupling.

To accomplish, affect and/or support such physical and/or mechanical coupling, base 2902 can further include a second retaining member (not shown in FIGS. 29A-29C but having similar structure, function and location as second retaining member 2344, 2444 of FIGS. 23A-24D), while sensor electronics module 2950 can further include a retention feature 2956 configured to mate with the second retaining member. Second retaining member 2942 and retention feature 2956 can have similar or the same structure, function and locations as second retaining member 2344 and retention feature 2356 of FIGS. 23A-23C, respectively.

While not shown in FIGS. 29A-29B, the second retaining member can be disposed on base 2902, for example as described in connection with FIGS. 23A-23C, rather than on a cover, for example as described in connection with FIGS. 24A-24D. In some embodiments, the second retaining member is an integral part of base 2902 and is not configured to be separable from base 2902. In some other embodiments, base 2902 may comprise a frangible tab similar to that previously described in connection with at least FIGS. 23A-24D and the second retaining member can be disposed on the frangible tab. Sensor electronics module 2950 can be secured to and decoupled from base 2902 substantially as previously described in connection with at least FIGS. 23A-24D.

Example Over-the-Top Embodiments

Several "over the top" embodiments utilizing a sensor electronics module configured to be disposed over, surround and/or shroud an underlying base are described in connection with FIGS. 30A-37D below.

While not shown in FIGS. 30A-37D, bases 3002-3702 can comprise an analyte sensor (e.g., analyte sensor 104 of FIG. 1, analyte sensor 212 of FIG. 2, analyte sensor 1016 of FIG. 10A) configured to generate a sensor signal indicative of an analyte (e.g., glucose) concentration of a host, while sensor electronics modules 3050-3750 can include sensor electronics (e.g., sensor electronics 106 of FIGS. 1 and/or 2) as described herein and may include at least a wireless transceiver configured to transmit a wireless signal based at least in part on the sensor signal generated by the analyte sensor.

In some embodiments, an analyte sensor base assembly may include base 3002-3702 configured to attach to a skin of a host and one or more of the analyte sensor as described above and configured to generate a sensor signal indicative of an analyte concentration level of the host, at least one battery at least as will be described below, at least one sensor contact 3008-3708 and/or 3010-3710, at least one battery contact 3028-3738 and/or 3029-3729, a sealing member 3024-3724 and/or 3325, 3525 3725 configured to provide a seal around at least the at least one battery contact 3028-3738 and/or 3029-3729, and/or any other features associated with and/or configured to couple with base 3002-3702 at least as described below.

Figure 30A:
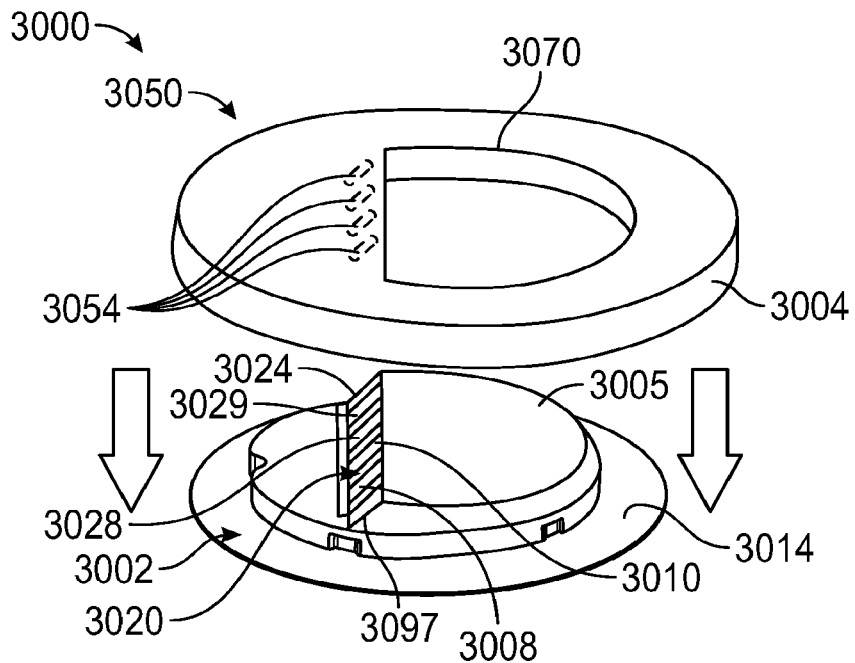
FIG. 30A is an exploded perspective view of an example base and a sensor electronics module configured to be secured over or on the base, according to some embodiments.
Figure 30B:
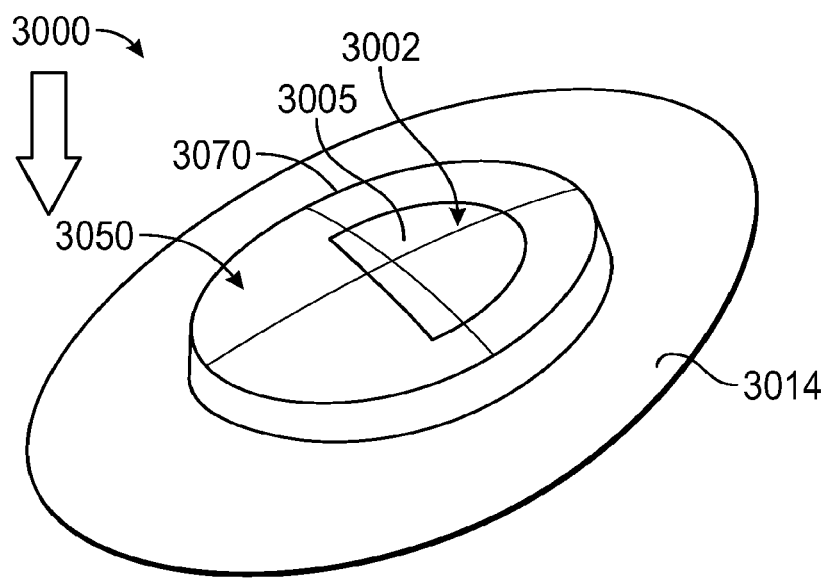
FIG. 30B is a perspective assembled view of the sensor electronics module secured to the base of FIG. 30A.

FIG. 30A is an exploded perspective view of an example base 3002 and a sensor electronics module 3050 configured to be secured over or on base 3002, according to some embodiments. FIG. 30B is a perspective assembled view of sensor electronics module 3050 secured to base 3002 of FIG. 30A. Discussion follows with respect to FIGS. 30A-30B below.

As shown in the figures, analyte sensor system 3000 comprises base 3002 and sensor electronics module 3050. Base 3002 can be configured to attach to the skin of the host, for example, utilizing an adhesive pad 3014, which can be disposed on a back surface of base 3002. Adhesive pad 3014 can have substantially similar features and function as previously described for adhesive pad 2314 of FIGS. 23A-23C.

As shown in the figures, sensor electronics module 3050 can have a raised perimeter 3004 configured to at least partially surround base 3002 as sensor electronics module 3050 is physically and/or mechanically coupled to base 3002, thereby guiding sensor electronics module 3050 into position during such physical and/or mechanical coupling.

Sensor electronics module 3050 can further include an aperture 3070. In some embodiments, aperture 3070 can be shaped such that there are a limited number of orientations between sensor electronics module 3050 and base 3002 that allow securing of one to the other. For example, aperture 3070 may have a shape that is symmetrical about at least one axis parallel to a top surface of sensor electronics module 3050 but that is asymmetrical about at least one other axis parallel to the top surface of sensor electronics module 3050. Such partially symmetrical shapes of aperture 3070 can make it easier for a host to secure sensor electronics module 3050 to base 3002 in the proper orientation.

Base 3002 can have an outer perimeter or shape that compliments an inner perimeter or shape of raised perimeter 3004 of sensor electronics module 3050. Base 3002 can further have a raised portion 3005 having an outer perimeter or shape that compliments an inner perimeter or shape of aperture 3070. Accordingly, when sensor electronics module 3050 is secured over a top of base 3002, base 3002 is configured to fit securely within raised perimeter 3004 of sensor electronics module 3050 and raised portion 3005 is configured to fit securely within aperture 3070. In some embodiments, a battery may be located in a cavity (not shown in FIGS. 30A-30B) within raised portion 3005 of base 3002. In some embodiments, when properly secured, a top surface of raised portion 3005 may sit substantially flush with a top surface of sensor electronics module 3050, thereby providing tactile feedback that sensor electronics module 3050 is properly secured to base 3002. However, the present disclosure is not so-limited and the top surface of raised portion 3005 may sit at an elevated or reduced position compared to the top surface of sensor electronics module 3050. Accordingly, the use of aperture 3070 in sensor electronics module 3050 and raised portion 3005 of base 3002 allow analyte sensor system 3000 to have a significantly reduced thickness or depth compared to other analyte sensor systems.

Base 3002 can further comprise a first sensor contact 3008 and a second sensor contact 3010, each electrically connected to a respective terminal of the analyte sensor, and a first battery contact 3028 and a second battery contact 3029, each electrically connected to a respective terminal of the battery. FIG. 30A illustrates contacts 3008, 3010, 3028, 3029 disposed on a sloped surface 3097 of raised portion 3005 of base 3002. Advantages of disposing contacts 3008, 3010, 3028, 3029 disposed on sloped surface 3097 included but are not limited to space efficiency and a lower profile of sensor electronics module 3050. However, the present disclosure is not so limited and contacts 3008, 3010, 3028, 3029 can be disposed on any suitable surface of base 3002. Base 3002 can further comprise a first sealing member 3024 configured to surround and seal each of contacts 3008, 3010, 3028, 3029 within a first cavity 3020 formed between facing surfaces of base 3002 and sensor electronics module 3050 and first sealing member 3024. Sealing member 3024 can, for example, include an overmolded component such as an overmolded gasket, an overmolded elastomeric feature, and/or an ultra-violet curable silicone.

Sensor electronics module 3050 can comprise a plurality of contacts 3054, disposed on an inner surface facing base 3002, which can include a first signal contact configured to make electrical contact with first sensor contact 3008, a second signal contact configured to make electrical contact with second sensor contact 3010, a first power contact configured to make electrical contact with first battery contact 3028, and a second power contact configured to make electrical contact with second battery contact 3029. Such first and second power contacts can be configured to receive power from the battery, while such first and second signal contacts can be configured to receive the sensor signal from the analyte sensor. In some alternative embodiments, first sealing member 3024 can alternatively be disposed on the same surface of sensor electronics module 3050 as contacts 3054, facing base 3002, to form first cavity 3020.

Sensor electronics module 3050 can be secured to base 3002 by pressing sensor electronics module 3050 against base 3002 in a direction substantially perpendicular to a bottom surface of base 3002 until one or more retention features (not shown in FIGS. 30A-30B) of sensor electronics module 3050 couple with one or more corresponding retaining members (not shown in FIGS. 30A-30B) of base 3002. In some embodiments, the retaining members of base 3002 may be the same members or features utilized to secure base 3002 to an applicator (not shown) for initial deployment to the skin of the host. Sensor electronics module 3050 can be decoupled from base 3002 by pulling sensor electronics module 3050 perpendicularly away from base 3002 while pushing against raised portion 3005 of base 3002 with sufficient force to cause decoupling.

Figure 31B:
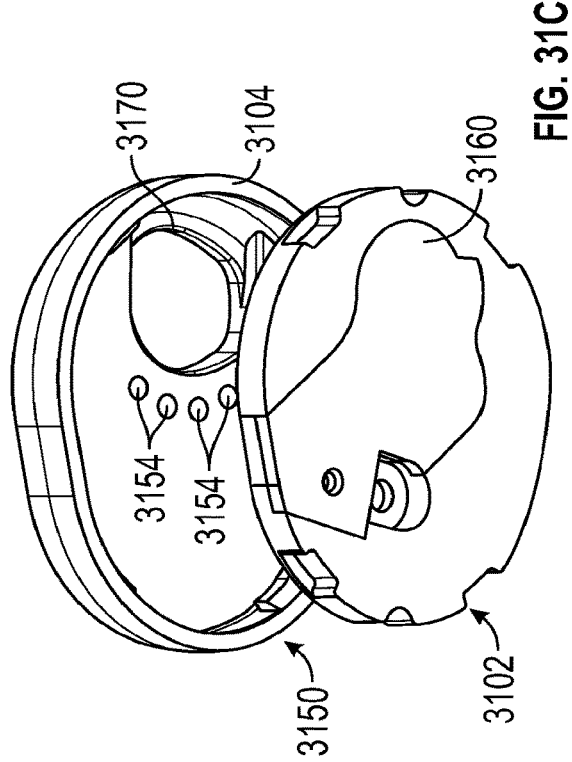
FIG. 31B is a perspective view of a battery disposed on a cover of the base of FIG. 31A.
Figure 31C:
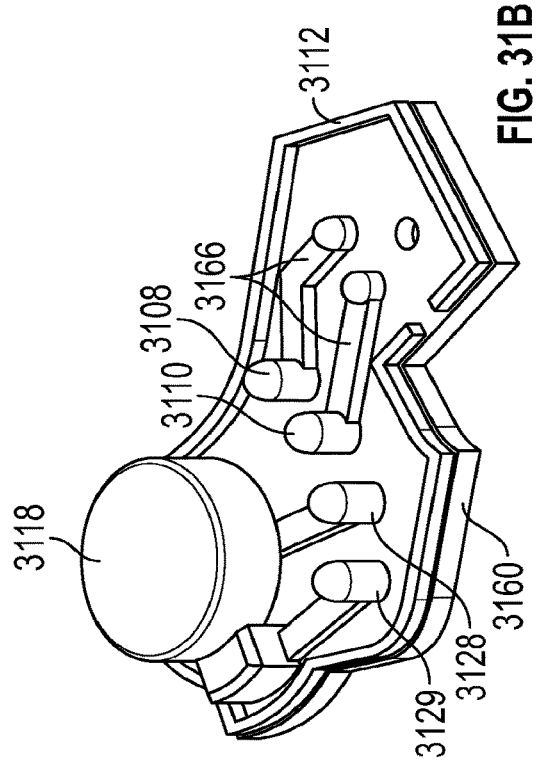
FIG. 31C is a perspective bottom view of the base and the sensor electronics module of FIG. 31A.
Figure 31A:
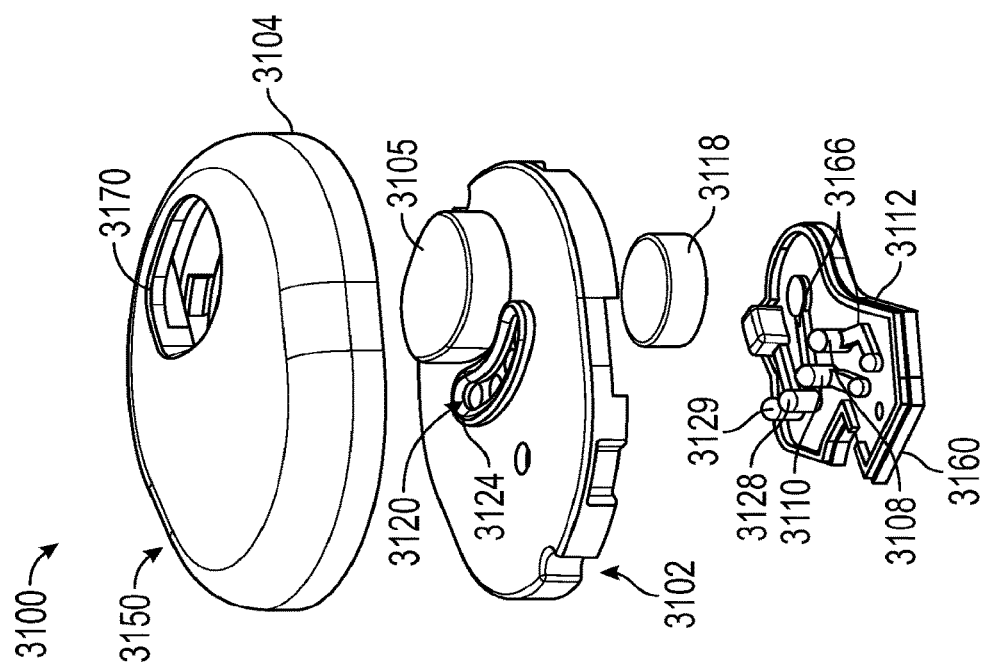
FIG. 31A is an exploded perspective view of an example base and a sensor electronics module configured to be secured over or on the base, according to some embodiments.

An embodiment similar to that described in connection with FIGS. 30A-30C is shown in FIGS. 31A-31C and described below. FIG. 31A is an exploded perspective view of an example base 3102 and a sensor electronics module 3150 configured to be secured over or on base 3102, according to some embodiments. FIG. 31B is a perspective view of a battery 3118 disposed on a cover 3160 of base 3102 of FIG. 31A. FIG. 31C is a perspective bottom view of base 3102 and sensor electronics module 3150 of FIG. 31A. Discussion follows with respect to FIGS. 31A-31C below.

As shown in the figures, analyte sensor system 3100 comprises base 3102 and sensor electronics module 3150. As shown in the figures, sensor electronics module 3150 can have a raised perimeter 3104 configured to at least partially surround base 3102 as sensor electronics module 3150 is physically and/or mechanically coupled to base 3102, thereby guiding sensor electronics module 3150 into position during such physical and/or mechanical coupling.

Sensor electronics module 3150 further includes an aperture 3170. Similar to aperture 3070 of FIGS. 30A-30C, aperture 3170 can be shaped such that there are a limited number of orientations between sensor electronics module 3150 and base 3102 that allow them to be secured to one another, making it easier for a host to secure sensor electronics module 3150 to base 3102 in the proper orientation.

Base 3102 can have an outer perimeter or shape that compliments an inner perimeter or shape of raised perimeter 3104 of sensor electronics module 3150. Base 3102 can further have a raised portion 3105 having an outer perimeter or shape that compliments an inner perimeter or shape of aperture 3170. Accordingly, when sensor electronics module 3150 is secured over a top of base 3102, base 3102 is configured to fit securely within raised perimeter 3104 of sensor electronics module 3150 and raised portion 3105 is configured to fit securely within aperture 3170.

As shown in FIG. 31A, a battery 3118 may be located in a cavity within raised portion 3105 of base 3102. As previously described in connection with FIGS. 30A-30C, when properly secured, a top surface of raised portion 3105 may sit substantially flush with, at an elevated position compared to, or at a lowered position compared to a top surface of sensor electronics module 3150, thereby providing tactile feedback that sensor electronics module 3150 is properly secured to base 3102.

Base 3102 is shown having a cover 3160 configured to be attached to and/or disposed on a bottom side of base 3102. Cover 3160 can comprise a plurality of conductive traces 3166, which can be formed utilizing any suitable process, for example, laser direct structuring (LDS) of cover 3160 or overmolding of a conductive elastomer. Conductive traces 3166 may be utilized to ultimately route electrical signals from the analyte sensor to sensor electronics module 3150 and/or power from battery 3118 to sensor electronics module 3150 and to the analyte sensor. Cover 3160 may be further configured to receive battery 3118. Cover 3160 can be secured to the bottom surface of base 3102 utilizing any suitable method, for example, snaps, adhesive, friction fittings, heat-staking, and/or laser, heat or ultra-sonic welding along weld line 3112. As shown in FIG. 31D, once secured to base 3102, cover 3160 may secure battery 3118 within a cavity in the bottom surface of base 3102.

As shown in FIGS. 31A-31B, a first sensor contact 3108 and a second sensor contact 3110 are each electrically coupled to a respective terminal of the analyte sensor in base 3102 via at least some of conductive traces 3166 on cover 3160. A first battery contact 3128 and a second battery contact 3129 are also each electrically coupled to a respective terminal of battery 3118 via at least some other of conductive traces 3166 on cover 3160. Contacts 3108, 3110, 3128, 3129 can comprise conductive elastomeric contacts (e.g. pucks), springs, tabs, posts, pogo pins, flat conductive pads or traces, or any other suitable conductive materials and/or structures.

Base 3102 further comprises a first sealing member 3124. When cover 3160 is secured to base 3102, each of contacts 3108, 3110, 3128, 3129 can protrude through first sealing member 3124.

As shown in FIG. 31C, a facing (e.g., bottom) surface of sensor electronics module 3150 further comprises a plurality of contacts 3154, which can include a first signal contact configured to make electrical contact with first sensor contact 3108, a second signal contact configured to make electrical contact with second sensor contact 3110, a first power contact configured to make electrical contact with first battery contact 3128, and a second power contact configured to make electrical contact with second battery contact 3129. Accordingly, the first and second signal contacts on the bottom surface of sensor electronics module 3150 are configured to receive the sensor signal from the analyte sensor, while the first and second power contacts are configured to receive power from battery 3118 when sensor electronics module 3150 is properly secured to base 3102. Such contacts on sensor electronics module 3150 can comprise conductive elastomeric contacts (e.g. pucks), springs, tabs, posts, pogo pins, flat conductive pads or traces, or any other suitable conductive materials and/or structures.

When sensor electronics module 3150 is secured to base 3102, sealing member 3124 is configured to press against the facing surface of sensor electronics module 3150, thereby forming a first cavity 3120 between base 3102 and sensor electronics module 3150. Accordingly, sealing member 3124 is configured to surround and create a continuous seal around first and second sensor contacts 3108, 3110, first and second battery contacts 3128, 3129, the first and second signal contacts and the first and second power contacts of sensor electronics module 3150 within first cavity 3120. Sealing member 3124 can, for example, include an overmolded component such as an overmolded gasket, an overmolded elastomeric feature, and/or an ultra-violet curable silicone that may be coupled to or assembled with base 3102.

Sensor electronics module 3150 can be secured to and decoupled from base 3102 in similar fashions to that previously described in connection with FIGS. 30A-30C.

Figure 32:
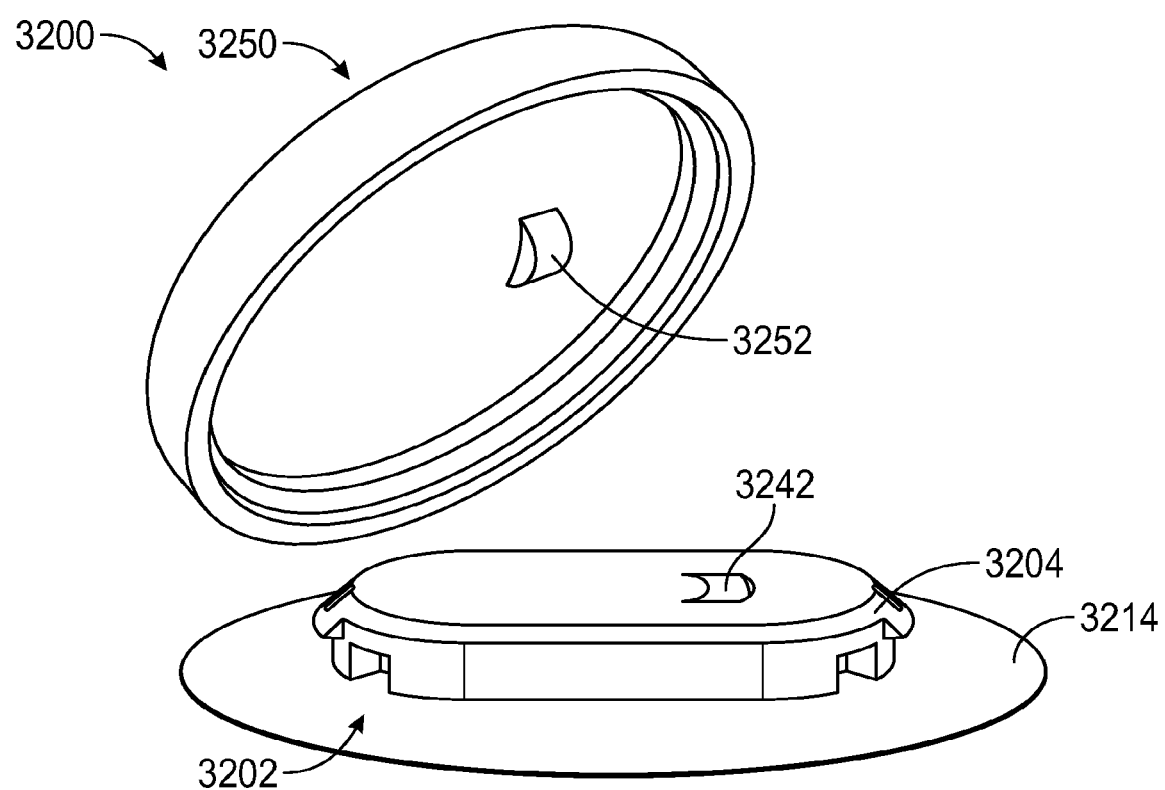
FIG. 32 is a perspective view of an example base and a sensor electronics module configured to be secured over or on the base, according to some embodiments.

FIG. 32 is a perspective view of an example base 3202 and a sensor electronics module 3250 configured to be secured over or on base 3202, according to some embodiments. Analyte sensor system 3200 comprises base 3202 and sensor electronics module 3250.

Base 3202 can be configured to attach to the skin of the host, for example, utilizing an adhesive pad 3214, which can be disposed on a back surface of base 3202. Adhesive pad 3214 can have substantially similar features and function as previously described for adhesive pad 2314 of FIGS. 23A-23C.

Sensor electronics module 3250 is illustrated as having a raised perimeter 3204 configured to at least partially surround base 3202 as sensor electronics module 3250 is physically and/or mechanically coupled to base 3202, thereby guiding sensor electronics module 3250 into position during such physical and/or mechanical coupling.

Sensor electronics module 3250 can further include a protrusion 3252 extending away from an underside of sensor electronics module 3250 and configured to mate within a corresponding recess 3242 in a top surface of base 3204 when sensor electronics module 3250 is properly oriented and secured to base 3202. Utilizing protrusion 3252 and recess 3242 can allow the host to properly orient and align sensor electronics module 3250 with respect to base 3202 without direct line of sight of the aligning/securing process.

When sensor electronics module 3250 is secured over a top of base 3202, base 3202 is configured to fit securely within raised perimeter 3204 of sensor electronics module 3250 and protrusion 3252 is configured to fit securely within recess 3242.

Further aspects of analyte sensor system 3200 are discussed in connection with a similar embodiment as shown in FIGS. 33A-33C below. Accordingly, analyte sensor system 3200 can be considered to have similar or the same features as those described for analyte sensor system 3300 of FIGS. 33A-33D.

FIG. 33A is an exploded perspective view of an example base 3302 and a sensor electronics module 3350 configured to be secured over or on base 3302, according to some embodiments. FIG. 33B is a perspective view of a battery 3318 disposed on a cover 3360 of base 3302 of FIG. 33A. FIG. 33C is an exploded perspective bottom view of cover 3360 and base 3302 of FIG. 33A. And FIG. 33D is a perspective bottom view of cover 3360 secured to base 3302 of FIG. 33A. Discussion follows with respect to FIGS. 33A-33D below.

As shown in the figures, analyte sensor system 3300 comprises base 3302 and sensor electronics module 3350. Sensor electronics module 3350 can have a raised perimeter 3304 configured to at least partially surround base 3302 as sensor electronics module 3350 is physically and/or mechanically coupled to base 3302, thereby guiding sensor electronics module 3350 into position during such physical and/or mechanical coupling.

Sensor electronics module 3350 further includes a protrusion 3352 and base 2202 further includes a recess 3342, similar to and having substantially the same functionality as protrusion 3252 and recess 3242 of FIG. 32, respectively.

In some embodiments, base 3302 can have an outer perimeter or shape that compliments an inner perimeter or shape of raised perimeter 3304 of sensor electronics module 3350. However, the present disclosure is not so-limited and base 3302 can have any outer perimeter or shape that will fit securely within raised perimeter 3304 of sensor electronics module 3350.

Base 3302 is shown having a cover 3360 configured to be attached to and/or disposed on a bottom side of base 3302. Cover 3360 can comprise a plurality of conductive traces 3366, which can be formed utilizing any suitable process, for example, laser direct structuring (LDS) of cover 3360 or overmolding of a conductive elastomer. Conductive traces 3366 may be utilized to ultimately route electrical signals from the analyte sensor to sensor electronics module 3350 and/or power from battery 3318 to sensor electronics module 3350 and/or to the analyte sensor. Cover 3360 can be secured to the bottom surface of base 3302 utilizing any suitable method, for example, snaps, adhesive, friction fittings, heat-staking, and/or laser, heat or ultra-sonic welding along weld line 3312. Once secured to base 3302, cover 3360 may secure battery 3318 within a cavity in the bottom surface of base 3302.

As shown in FIGS. 33A-33B, a first sensor contact 3308 and a second sensor contact 3310 are each electrically coupled to a respective terminal of the analyte sensor in base 3302 via at least some of conductive traces 3366 on cover 3360. A first battery contact 3328 and a second battery contact 3329 are also each electrically coupled to a respective terminal of battery 3318 via at least some other of conductive traces 3366 on cover 3360. Contacts 3308, 3310, 3328, 3329 can comprise conductive elastomeric contacts (e.g. pucks), springs, tabs, posts, pogo pins, flat conductive pads or traces, or any other suitable conductive materials and/or structures.

Base 3302 further comprises a first sealing member 3324 and a second sealing member 3325. When cover 3360 is secured to base 3302, contacts 3308 and 3310 can protrude through first sealing member 3324 and contacts 3328 and 3329 can protrude through second sealing member 3325.

As shown in FIG. 33A, a facing (e.g., bottom) surface of sensor electronics module 3350 further comprises a plurality of contacts 3354, which can include a first signal contact configured to make electrical contact with first sensor contact 3308, a second signal contact configured to make electrical contact with second sensor contact 3310, a first power contact configured to make electrical contact with first battery contact 3328, and a second power contact configured to make electrical contact with second battery contact 3329. Accordingly, the first and second signal contacts on the bottom surface of sensor electronics module 3350 are configured to receive the sensor signal from the analyte sensor, while the first and second power contacts are configured to receive power from battery 3318 when sensor electronics module 3350 is properly secured to base 3302. Such contacts on sensor electronics module 3350 can comprise conductive elastomeric contacts (e.g. pucks), springs, tabs, posts, pogo pins, flat conductive pads or contacts, or any other suitable conductive materials.

When sensor electronics module 3350 is secured to base 3302, first sealing member 3324 is configured to press against the facing surface of sensor electronics module 3350, thereby forming a first cavity 3320a between base 3302 and sensor electronics module 3350, while second sealing member 3325 is configured to press against the facing surface of sensor electronics module 3350, thereby forming a second cavity 3320b between base 3302 and sensor electronics module 3350. Accordingly, first sealing member 3324 is configured to surround and create a continuous seal around first and second sensor contacts 3308, 3310 and the first and second signal contacts of 3354 within first cavity 3320a and the first and second power contacts of sensor electronics module 3350 within first cavity 3320a, while second sealing member 3325 is configured to surround and create a continuous seal around first and second battery contacts 3328, 3329 and the first and second power contacts of 3354 within second cavity 3320b. First and second sealing members 3324, 3325 can, for example, include overmolded components such as overmolded gaskets, overmolded elastomeric features, and/or ultra-violet curable silicone that may be coupled to or assembled with base 3302.

Sensor electronics module 3350 can be secured to and decoupled from base 3302 in similar fashions to that previously described in connection with FIGS. 30A-30C.

Omni-Directional Over-the-Top Embodiments

FIGS. 34-37D illustrate several embodiments of analyte sensor systems in which a sensor electronics module having a substantially circular profile is configured to be omni-directionally secured to a base also having a substantially circular profile.

Figure 34:
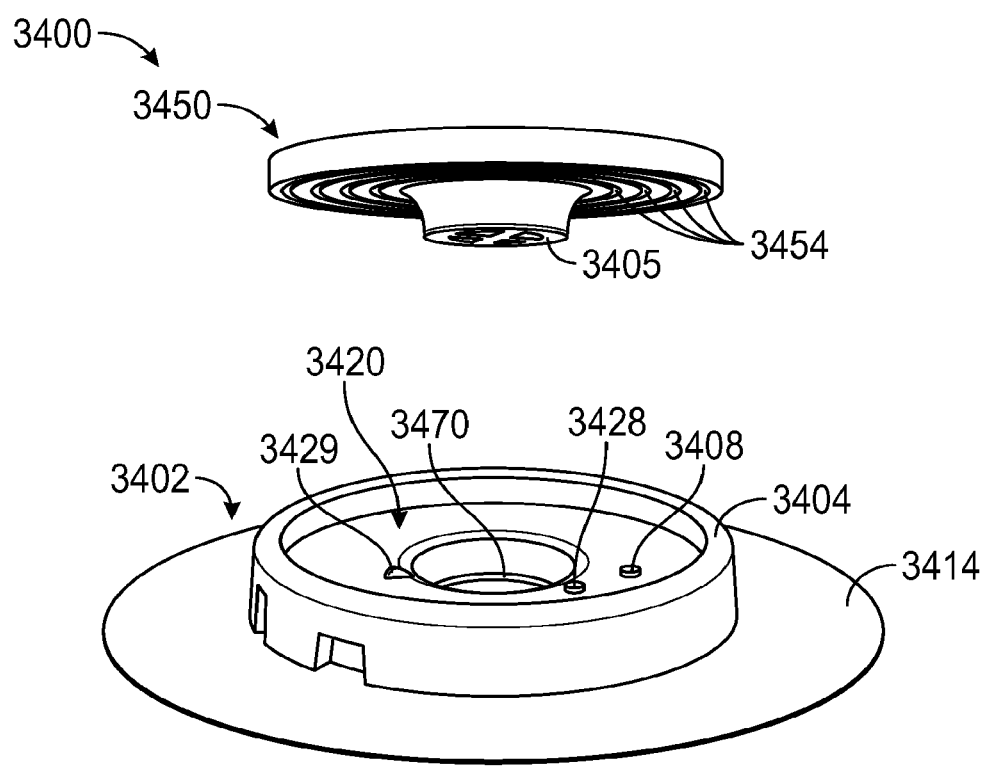
FIG. 34 is an exploded perspective view of an example base and a sensor electronics module configured to be secured over or on the base, according to some embodiments.

FIG. 34 is an exploded perspective view of an example base 3402 and a sensor electronics module 3450 configured to be secured over or on base 3402, according to some embodiments.

Analyte sensor system 3400 comprises base 3402 and sensor electronics module 3450. As illustrated, base 3402 and sensor electronics module 3450 can each have a substantially circular profile, which allows for omni-directional alignment of one with respect to the other.

Base 3402 can be configured to attach to the skin of the host, for example, utilizing an adhesive pad 3414, which can be disposed on a back surface of base 3402. Adhesive pad 3414 can have substantially similar features and function as previously described for adhesive pad 2314 of FIGS. 23A-23C.

Base 3402 can have a raised perimeter 3404 configured to at least partially surround sensor electronics module 3450 as sensor electronics module 3450 is physically and/or mechanically coupled to base 3402, thereby guiding sensor electronics module 3450 into position during such physical and/or mechanical coupling. In some embodiments, raised perimeter 2404 can have a substantially circular perimeter. Base 3402 can further include an aperture 3470, which, in some embodiments, can have a substantially circular shape.

Sensor electronics module 3450 can have a substantially circular outer perimeter or shape that compliments an inner perimeter or shape of raised perimeter 3404 of base 3450. Sensor electronics module 3450 can further have a raised portion 3405 having a substantially circular outer perimeter or shape that compliments an inner perimeter or shape of aperture 3470. Accordingly, when sensor electronics module 3450 is secured over a top of base 3402, sensor electronics module 3450 is configured to fit securely within raised perimeter 3404 of base 3402 and raised portion 3405 is configured to fit securely within aperture 3470. In some embodiments, when properly secured, a bottom surface of raised portion 3405 may sit substantially flush with a bottom surface of base 3402. However, the present disclosure is not so-limited and the bottom surface of raised portion 3405 may sit at an elevated or reduced position compared to the bottom surface of base 3402. Accordingly, at least some of the substantially circular shape and/or perimeters of sensor electronics module 3450, raised portion 3405, raised perimeter 3404 of base 3402 and/or of aperture 3470 allow for omni-directional mounting of sensor electronics module 3450 to base 3402. It is contemplated that the omni-directional mounting can increase convenience to the user when installing the sensor electronics module 3450 without first having to align it.

Base 3402 can further comprise a first sensor contact 3408 and a second sensor contact (not shown in FIG. 34 but substantially similar to first sensor contact 3408), each configured to be electrically connected to a respective terminal of the analyte sensor, and a first battery contact 3428 and a second battery contact 3429, each configured to be electrically connected to a respective terminal of a battery (not shown in FIG. 34) disposed within base 3402. Base 3402 can further comprise a first sealing member (not shown in FIG. 34 but substantially similar to first sealing member 3524 of FIGS. 35A-35D) configured to surround and seal the first and second sensor contacts 3408 and the first and second battery contacts 3428 within a first cavity 3420 formed between facing surfaces of base 3402 and sensor electronics module 3450 and the first sealing member. The first sealing member can, for example, include an overmolded component such as an overmolded gasket, an overmolded elastomeric feature, and/or an ultra-violet curable silicone.

Sensor electronics module 3450 can comprise a plurality of concentrically-circular contacts 3454 disposed on an inner surface facing base 3402. In some embodiments, contacts 3454 may each have a substantially ring-like form and may each be annularly spaced apart from one another. As shown, contacts 3454 may be centered about raised portion 3405, which allows contacts 3454 to make electrical contact with respective ones of the first and second sensor contacts 3408 and the first and second battery contacts 3428 of base 3402 when sensor electronics module 3450 is mounted to base 3402. Due to the annular form of each of contacts 3454, it is contemplated that sensor electronics module 3450 can be mounted onto base 3402 in any orientation. Each contact 3454 can be configured to make contact with one of sensor contacts or battery contacts at any point along the respective contact 3454. Contacts 3454 can be formed utilizing any suitable process, for example, laser direct structuring (LDS) of base 3502 or overmolding of a conductive elastomer. Contacts 3454 can include a first signal contact configured to make electrical contact with first sensor contact 3408, a second signal contact configured to make electrical contact with the second sensor contact (not shown in FIG. 34), a first power contact configured to make electrical contact with first battery contact 3428, and a second power contact configured to make electrical contact with the second battery contact (not shown in FIG. 34). Such first and second power contacts can be configured to receive power from the battery, while such first and second signal contacts can be configured to receive the sensor signal from the analyte sensor. In some alternative embodiments, the first sealing member (not shown in FIG. 34) can alternatively be disposed on the same surface, or an adjacent surface, of sensor electronics module 3450 as contacts 3454, facing base 3402 to form first cavity 3420.

Sensor electronics module 3450 can be secured to base 3402 by pressing sensor electronics module 3450 against base 3402 in a direction substantially perpendicular to a bottom surface of base 3402 until one or more retention features of sensor electronics module 3450 snap into one or more corresponding retaining members of base 3402. In some embodiments, the retaining members of base 3402 may be the same members or features utilized to secure base 3402 to an applicator (not shown) for initial deployment to the skin of the host. Sensor electronics module 3450 can be decoupled from base 3402 by pulling sensor electronics module 3450 perpendicularly away from base 3402 while anchoring base 3402 with sufficient force to cause decoupling.

An embodiment similar to that described in connection with FIG. 34 is shown in FIGS. 35A-35D and described below. FIG. 35A is an exploded perspective view of an example base 3502 and a sensor electronics module 3550 configured to be secured over or on base 3502, according to some embodiments. FIG. 35B is an exploded perspective bottom view of base 3502 and sensor electronics module 3550 of FIG. 35A. FIG. 35C is a plan view of a bottom of base 3502 of FIG. 35A. FIG. 35D is a perspective cutaway view of sensor electronics module 3550 secured to base 3502 of FIG. 35A.

Analyte sensor system 3500 comprises base 3502 and sensor electronics module 3550. As illustrated, base 3502 and sensor electronics module 3550 can each have a substantially circular profile, which allows for omni-directional alignment therebetween. Base 3502 includes a battery 3518 configured to power the analyte sensor and/or sensor electronics module 3550. Battery 3518 can be disposed in a cavity through a top side of base 3502. In some embodiments, battery 3518 may be secured in its cavity utilizing conductive epoxy or another suitable adhesive compound.

Base 3502 can have a raised perimeter 3504 configured to at least partially surround sensor electronics module 3550 as sensor electronics module 3550 is physically and/or mechanically coupled to base 3502, thereby guiding sensor electronics module 3550 into position during such physical and/or mechanical coupling. In some embodiments, raised perimeter 2404 can have a substantially circular perimeter. In contrast to base 3402 of FIG. 34, in some embodiments, base 3502 may not include an aperture similar to aperture 3470.

Sensor electronics module 3550 can have a substantially circular outer perimeter or shape that compliments an inner perimeter or shape of raised perimeter 3504 of base 3550. In contrast to sensor electronics module 3450 of FIG. 34, in some embodiments, sensor electronics module 3550 may not have a raised portion similar to raised portion 3405, since base 3502 may not include an aperture similar to aperture 3470. However, when sensor electronics module 3550 is secured over a top of base 3502, sensor electronics module 3550 is similarly configured to fit securely within raised perimeter 3504 of base 3502. The substantially circular shape and/or perimeter of sensor electronics module 3550 and raised perimeter 3504 of base 3502 allow for omni-directional mounting of sensor electronics module 3550 to base 3502.

Base 3502 can further comprise a first sensor contact 3508 and a second sensor contact 3510, each electrically connected to a respective terminal of the analyte sensor, and a first battery contact 3528 and a second battery contact 3529, each electrically connected to a respective terminal of battery 3518. Base 3502 can further comprise a first sealing member 3524 configured to surround and seal each of first and second sensor contacts 3508, 3510 and first and second battery contacts 3528, 3529 within a first cavity 3520 formed between facing surfaces of base 3502 and sensor electronics module 3550 and first sealing member 3524. In some embodiments, first sealing member 3524 can be disposed on a surface of base 3202 facing sensor electronics module 3550, on a sidewall of raised perimeter 3504 of base 3202, or both. In some embodiments, base 3502 can further comprise a second sealing member 3525 disposed within a perimeter of first sealing member 3524 and around a through-hole 3540 of base 3202. First and/or second sealing members 3524, 3525 can, for example, include overmolded components such as overmolded gaskets, overmolded elastomeric features, and/or ultra-violet curable silicone.

Base 3502 is further illustrated as including a plurality of conductive contacts 3566, which can be formed utilizing any suitable process, for example, laser direct structuring (LDS) of base 3502 or overmolding of a conductive elastomer. Conductive traces 3566 may be utilized to ultimately route electrical signals from the analyte sensor to sensor electronics module 3550 and/or power from battery 3518 to sensor electronics module 3550 and to the analyte sensor.

Sensor electronics module 3550 can comprise a plurality of concentrically-circular contacts 3554 disposed on an inner surface facing base 3502. In some embodiments, contacts 3554 may each have a substantially ring-like form and may each be annularly spaced apart from one another, which allows contacts 3554 to make electrical contact with respective ones of first and second sensor contacts 3508, 3510 and first and second battery contacts 3528, 3529 of base 3502 when sensor electronics module 3550 is mounted to base 3502. Due to the annular form of each of contacts 3554, it is contemplated that sensor electronics module 3550 can be mounted onto base 3502 in any orientation. Each contact 3554 can be configured to make contact with one of sensor contacts or battery contacts at any point along the respective contact 3554. Contacts 3554 can be formed utilizing any suitable process, for example, laser direct structuring (LDS) of base 3502 or overmolding of a conductive elastomer. Contacts 3554 can include a first signal contact configured to make electrical contact with first sensor contact 3508, a second signal contact configured to make electrical contact with second sensor contact 3510, a first power contact configured to make electrical contact with first battery contact 3528, and a second power contact configured to make electrical contact with second battery contact 3529. Such first and second power contacts can be configured to receive power from the battery, while such first and second signal contacts can be configured to receive the sensor signal from the analyte sensor. In some alternative embodiments, one or both of first and second sealing members 3524, 3525 can alternatively be disposed on the same surface, or an adjacent surface, of sensor electronics module 3550 as contacts 3554, facing base 3502, to form first cavity 3520.

Sensor electronics module 3550 can be secured to base 3502 by pressing sensor electronics module 3550 against base 3502 in a direction substantially perpendicular to a bottom surface of base 3502 until one or more retention features of sensor electronics module 3550 snap into one or more corresponding retaining members of base 3502. In some embodiments, the retaining members of base 3502 may be the same members or features utilized to secure base 3502 to an applicator (not shown) for initial deployment to the skin of the host. Sensor electronics module 3550 can be decoupled from base 3502 by pulling sensor electronics module 3550 perpendicularly away from base 3502 while anchoring base 3502 with sufficient force to cause decoupling.

Figure 36:
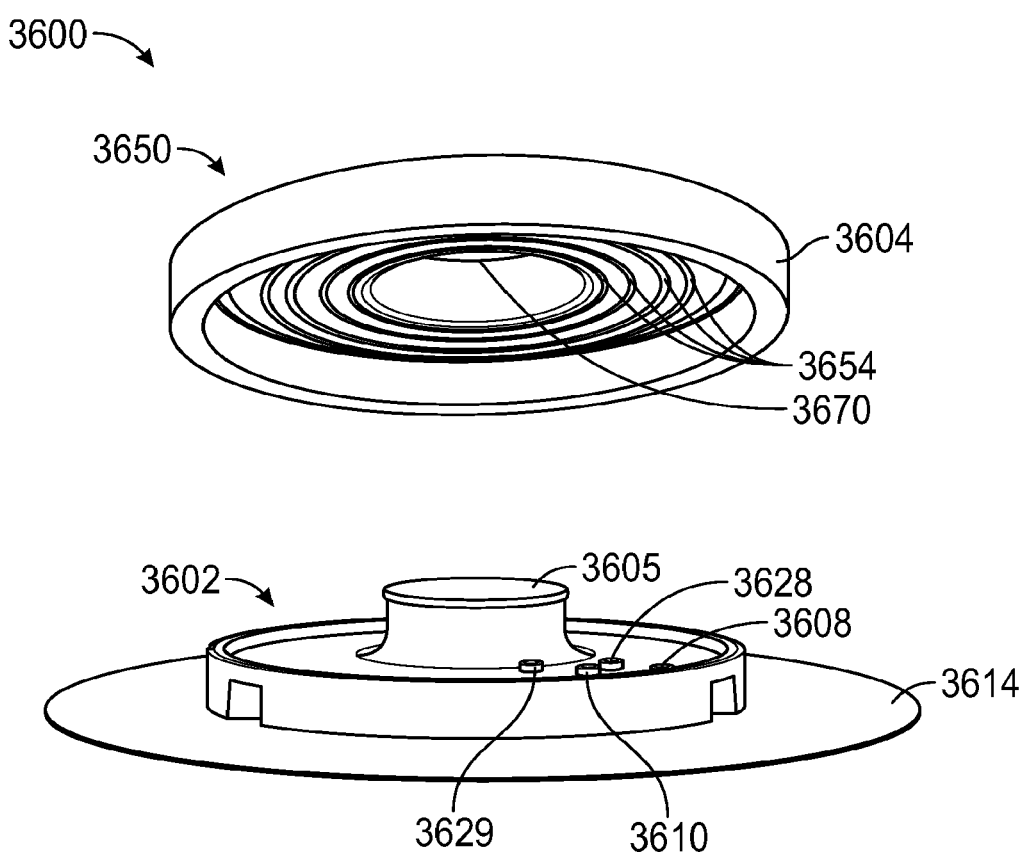
FIG. 36 is an exploded perspective view of an example base and a sensor electronics module configured to be secured over or on the base, according to some embodiments.

FIG. 36 is an exploded perspective view of an example base 3602 and a sensor electronics module 3650 configured to be secured over or on base 3602, according to some embodiments.

Analyte sensor system 3600 comprises base 3602 and sensor electronics module 3650. As illustrated, base 3602 and sensor electronics module 3650 can each have a substantially circular profile, which allows for omni-directional alignment therebetween.

Base 3602 can be configured to attach to the skin of the host, for example, utilizing an adhesive pad 3614, which can be disposed on a back surface of base 3602. Adhesive pad 3614 can have substantially similar features and function as previously described for adhesive pad 2314 of FIGS. 23A-23C.

Sensor electronics module 3650 can have a raised perimeter 3604 configured to at least partially surround base 3602 as sensor electronics module 3650 is physically and/or mechanically coupled to base 3602, thereby guiding sensor electronics module 3650 into position during such physical and/or mechanical coupling. In some embodiments, raised perimeter 3604 can have a substantially circular perimeter. Sensor electronics module 3650 can further include an aperture 3670, which, in some embodiments, can have a substantially circular shape.

Base 3602 can have a substantially circular outer perimeter or shape that compliments the inner perimeter or shape of raised perimeter 3604 of sensor electronics module 3650. Base 3602 can further have a raised portion 3605 having a substantially circular outer perimeter or shape that compliments an inner perimeter or shape of aperture 3670. Accordingly, when sensor electronics module 3650 is secured over a top of base 3602, base 3602 is configured to fit securely within raised perimeter 3604 of sensor electronics module 3650 and raised portion 3605 is configured to fit securely within aperture 3670. In some embodiments, when properly secured, a top surface of raised portion 3605 may sit substantially flush with a top surface of sensor electronics module 3650. However, the present disclosure is not so-limited and the top surface of raised portion 3605 may sit at an elevated or reduced position compared to the top surface of sensor electronics module 3650. Accordingly, at least some of the substantially circular shapes and/or perimeters of sensor electronics module 3650, raised portion 3605 of base 3602, raised perimeter 3604 of sensor electronics module 3650 and/or of aperture 3670 allow for omni-directional mounting of sensor electronics module 3650 to base 3602.

Base 3602 can further comprise a first sensor contact 3608 and a second sensor contact 3610, each electrically connected to a respective terminal of the analyte sensor, and a first battery contact 3628 and a second battery contact 3629, each electrically connected to a respective terminal of a battery (not shown in FIG. 36) disposed within base 3602. Base 3602 can further comprise a first sealing member (not shown in FIG. 36 but substantially similar to first sealing member 3724 of FIGS. 37A-37D) configured to surround and seal each of first and second sensor contacts 3608 and first and second battery contacts 3628 within a first cavity 3620 formed between facing surfaces of base 3602 and sensor electronics module 3650 and the first sealing member. The first sealing member can, for example, include an overmolded component such as an overmolded gasket, an overmolded elastomeric feature, and/or an ultra-violet curable silicone.

Sensor electronics module 3650 can comprise a plurality of concentrically-circular contacts 3654 disposed on an inner surface facing base 3602. In some embodiments, contacts 3654 may each have a substantially ring-like form and may each be annularly spaced apart from one another. As shown, contacts 3654 may be centered about aperture 3670, which allows contacts 3654 to make electrical contact with respective ones of first and second sensor contacts 3608, 3610 and first and second battery contacts 3628, 3729 of base 3602 when sensor electronics module 3650 is mounted to base 3602. Due to the annular form of each of contacts 3654, it is contemplated that sensor electronics module 3650 can be mounted onto base 3602 in any orientation. Each contact 3654 can be configured to make contact with one of sensor contacts or battery contacts at any point along the respective contact 3654. Contacts 3654 can be formed utilizing any suitable process, for example, laser direct structuring (LDS) of base 3502 or overmolding of a conductive elastomer. Contacts 3654 can include a first signal contact configured to make electrical contact with first sensor contact 3608, a second signal contact configured to make electrical contact with second sensor contact 3610, a first power contact configured to make electrical contact with first battery contact 3628, and a second power contact configured to make electrical contact with second battery contact 3629. Such first and second power contacts can be configured to receive power from the battery, while such first and second signal contacts can be configured to receive the sensor signal from the analyte sensor. In some alternative embodiments, the first sealing member (not shown in FIG. 36) can alternatively be disposed on the same surface, or an adjacent surface, of sensor electronics module 3650 as contacts 3654 facing base 3602 to form first cavity 3620.

Sensor electronics module 3650 can be secured to base 3602 by pressing sensor electronics module 3650 against base 3602 in a direction substantially perpendicular to a bottom surface of base 3602 until one or more retention features of sensor electronics module 3650 snap into one or more corresponding retaining members of base 3602. In some embodiments, the retaining members of base 3602 may be the same members or features utilized to secure base 3602 to an applicator (not shown) for initial deployment to the skin of the host. Sensor electronics module 3650 can be decoupled from base 3602 by pulling sensor electronics module 3650 perpendicularly away from base 3602 while pressing down on raised portion 3605 of base 3602 with sufficient force to cause decoupling.

Figure 37A:
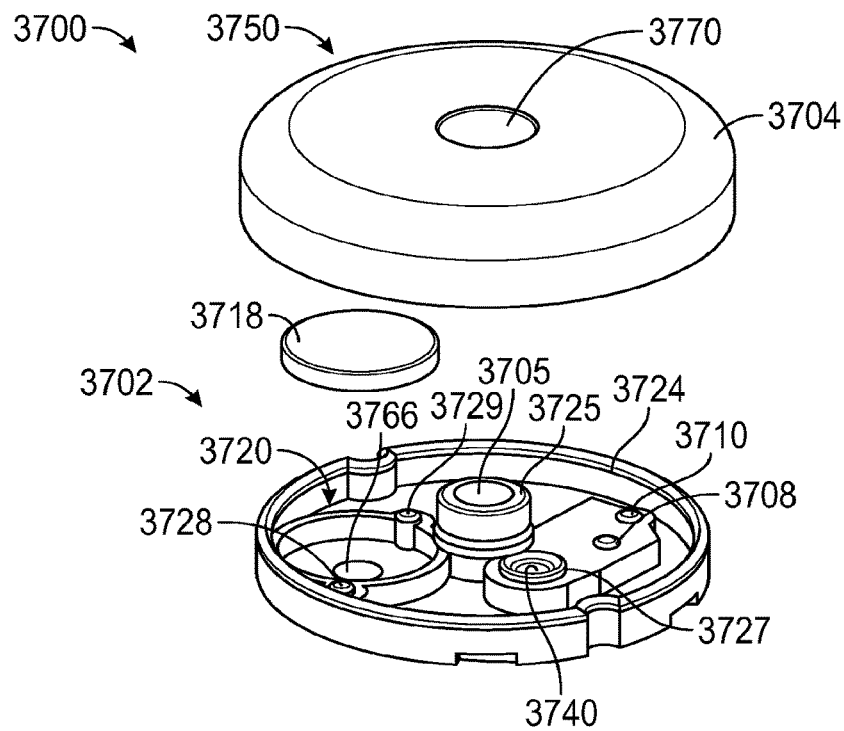
FIG. 37A is an exploded perspective view of an example base and a sensor electronics module configured to be secured over or on the base, according to some embodiments.
Figure 37B:
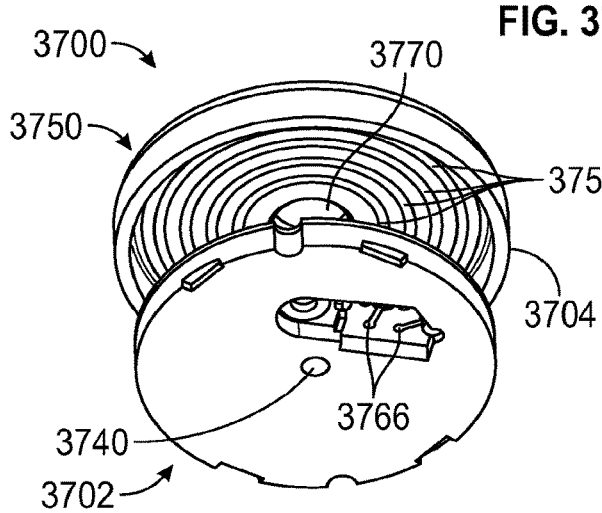
FIG. 37B is an exploded perspective bottom view of the base and the sensor electronics module of FIG. 37A.
Figure 37C:
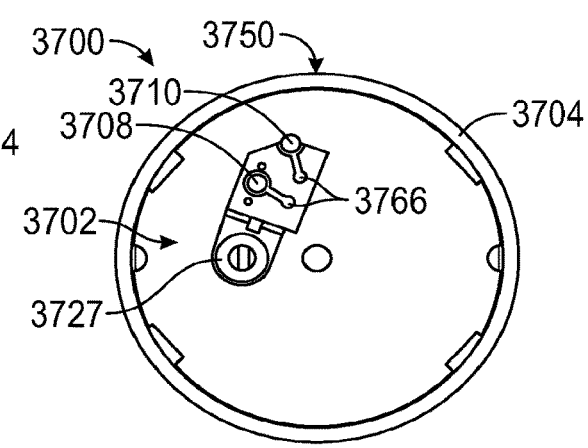
FIG. 37C is a plan view of a bottom of the base of FIG. 37A.
Figure 37D:
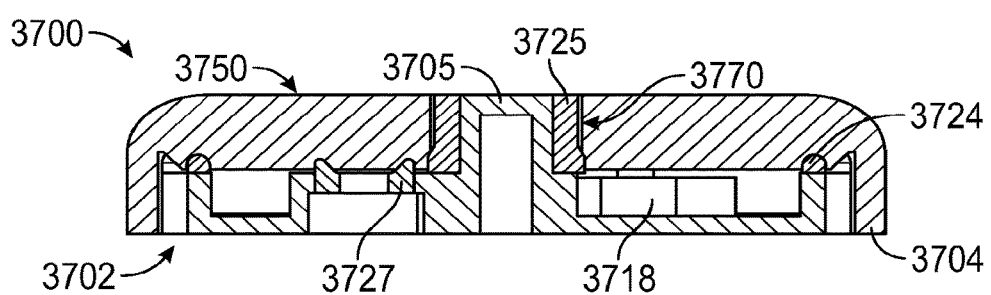
FIG. 37D is a side cutaway view of the sensor electronics module secured to the base of FIG. 37A.

An embodiment similar to that described in connection with FIG. 36 is shown in FIGS. 37A-37D and described below. FIG. 37A is an exploded perspective view of an example base 3702 and a sensor electronics module 3750 configured to be secured over or on base 3702, according to some embodiments. FIG. 37B is an exploded perspective bottom view of base 3702 and sensor electronics module 3750 of FIG. 37A. FIG. 37C is a plan view of a bottom of base 3702 of FIG. 37A. FIG. 37D is a side cutaway view of sensor electronics module 3750 secured to base 3702 of FIG. 37A.

Analyte sensor system 3700 comprises base 3702 and sensor electronics module 3750. As illustrated, base 3702 and sensor electronics module 3750 can each have a substantially circular profile, which allows for omni-directional alignment therebetween. While not shown in FIGS. 37A-35D, base 3702 can comprise an analyte sensor (e.g., analyte sensor 104 of FIG. 1, analyte sensor 212 of FIG. 2, analyte sensor 1016 of FIG. 10A) configured to generate a sensor signal indicative of an analyte (e.g., glucose) concentration of a host. Base 3702 further comprises a battery 3718 configured to power the analyte sensor and/or sensor electronics module 3750. Battery 3718 can be disposed in a cavity through a top side of base 3702. In some embodiments, battery 3718 may be secured in its cavity utilizing conductive epoxy or another suitable adhesive compound.

While not shown in FIGS. 37A-37D, sensor electronics module 3750 can include sensor electronics (e.g., sensor electronics 106 of FIGS. 1 and/or 2) as described herein and may include at least a wireless transceiver configured to transmit a wireless signal based at least in part on the sensor signal generated by the analyte sensor.

Sensor electronics module 3750 can have a raised perimeter 3704 configured to at least partially surround base 3702 as sensor electronics module 3750 is physically and/or mechanically coupled to base 3702, thereby guiding sensor electronics module 3750 into position during such physical and/or mechanical coupling. In some embodiments, raised perimeter 2404 can have a substantially circular perimeter. Sensor electronics module 3750 can further include an aperture 3770, which, in some embodiments, can have a substantially circular shape.

Base 3702 can have a substantially circular outer perimeter or shape that compliments an inner perimeter or shape of raised perimeter 3704 of sensor electronics module 3750. Base 3702 can further have a raised portion 3405 having a substantially circular outer perimeter or shape that compliments an inner perimeter or shape of aperture 3770. Accordingly, when sensor electronics module 3750 is secured over a top of base 3702, sensor electronics module 3750 is configured to fit securely within raised perimeter 3704 of base 3702, while raised portion 3705 of base 3702 is configured to fit securely within aperture 3770. The substantially circular shape and/or perimeter of at least some of sensor electronics module 3750, aperture 3770, raised perimeter 3704 of sensor electronics module 3750, and raised portion 3705 of base 3702 allow for omni-directional mounting of sensor electronics module 3750 to base 3702.

Base 3702 can further comprise a first sensor contact 3708 and a second sensor contact 3710, each electrically connected to a respective terminal of the analyte sensor, and a first battery contact 3728 and a second battery contact 3729, each electrically connected to a respective terminal of battery 3718. Base 3702 can further comprise a first sealing member 3724 configured to surround and seal each of first and second sensor contacts 3708, 3710 and first and second battery contacts 3728, 3729 within a first cavity 3720 formed between facing surfaces of base 3702 and sensor electronics module 3750 and first sealing member 3724. In some embodiments, first sealing member 3724 can be disposed on a surface of base 3202 facing sensor electronics module 3750, on a sidewall of base 3202, or both. In some embodiments, base 3703 can further comprise a second sealing member 3725 disposed within a perimeter of first sealing member 3724 and around a sidewall of raised portion 3705 of base 3702. In some embodiments, base 3702 can further comprise a third sealing member 3727 disposed within a perimeter of first sealing member 3724 and around a through-hole 3740 of base 3202. First, second and/or third sealing members 3724, 3725, 3727 can, for example, include overmolded components such as overmolded gaskets, overmolded elastomeric features, and/or ultra-violet curable silicone.

Base 3702 is further illustrated as including a plurality of conductive contacts 3766, which can be formed utilizing any suitable process, for example, laser direct structuring (LDS) of base 3702 or overmolding of a conductive elastomer. Conductive traces 3766 may be utilized to ultimately route electrical signals from the analyte sensor to sensor electronics module 3750 and/or power from battery 3718 to sensor electronics module 3750 and to the analyte sensor.

Sensor electronics module 3750 can comprise a plurality of concentrically-circular contacts 3754 disposed on an inner surface facing base 3702. In some embodiments, contacts 3754 may each have a substantially ring-like form and may each be annularly spaced apart from one another, centered about aperture 3770, which allows contacts 3754 to make electrical contact with respective ones of first and second sensor contacts 3708, 3710 and first and second battery contacts 3728, 3729 of base 3702 when sensor electronics module 3750 is mounted to base 3702. Due to the annular form of each of contacts 3754, it is contemplated that sensor electronics module 3750 can be mounted onto base 3702 in any orientation. Each contact 3754 can be configured to make contact with one of sensor contacts or battery contacts at any point along the respective contact 3754. Contacts 3754 can be formed utilizing any suitable process, for example, laser direct structuring (LDS) of base 3702 or overmolding of a conductive elastomer. Contacts 3754 can include a first signal contact configured to make electrical contact with first sensor contact 3708, a second signal contact configured to make electrical contact with second sensor contact 3710, a first power contact configured to make electrical contact with first battery contact 3728, and a second power contact configured to make electrical contact with second battery contact 3729. Such first and second power contacts can be configured to receive power from battery 3718, while such first and second signal contacts can be configured to receive the sensor signal from the analyte sensor. In some alternative embodiments, one or more of first, second and/or third sealing members 3724, 3725, 3727 can alternatively be disposed on the same surface, or an adjacent surface, of sensor electronics module 3750 as contacts 3754 facing base 3702 to form first cavity 3720.

Sensor electronics module 3750 can be secured to base 3702 by pressing sensor electronics module 3750 against base 3702 in a direction substantially perpendicular to a bottom surface of base 3702 until one or more retention features of sensor electronics module 3750 snap into one or more corresponding retaining members of base 3702. In some embodiments, the retaining members of base 3702 may be the same members or features utilized to secure base 3702 to an applicator (not shown) for initial deployment to the skin of the host. Sensor electronics module 3750 can be decoupled from base 3702 by pulling sensor electronics module 3750 perpendicularly away from base 3702 while pushing down on raised portion 3705 of base 3702 with sufficient force to cause decoupling.

Slider Embodiments

FIGS. 38A-39C illustrate several embodiments of analyte sensor systems in which a base includes a rail along which a sensor electronics module, having a channel configured to accommodate the rail, can be slid over and secured onto the base.

While not shown in FIGS. 38A-39C, bases 3802-3902 can comprise an analyte sensor (e.g., analyte sensor 104 of FIG. 1, analyte sensor 212 of FIG. 2, analyte sensor 1016 of FIG. 10A) configured to generate a sensor signal indicative of an analyte (e.g., glucose) concentration of a host, while sensor electronics modules 3850-3950 can include sensor electronics (e.g., sensor electronics 106 of FIGS. 1 and/or 2) as described herein and may include at least a wireless transceiver configured to transmit a wireless signal based at least in part on the sensor signal generated by the analyte sensor.

In some embodiments, an analyte sensor base assembly may include base 3802-3902 configured to attach to a skin of a host and one or more of the analyte sensor as described above and configured to generate a sensor signal indicative of an analyte concentration level of the host, at least one battery at least as will be described below, at least one sensor contact 3808-3908 and/or 3810-3910, at least one battery contact 3828-3938 and/or 3829-3929, a sealing member 3824-3924 and/or 3925 configured to provide a seal around at least the at least one battery contact 3828-3938 and/or 3829-3929, and/or any other features associated with and/or configured to couple with base 3802-3902 at least as described below.

Figure 38A:
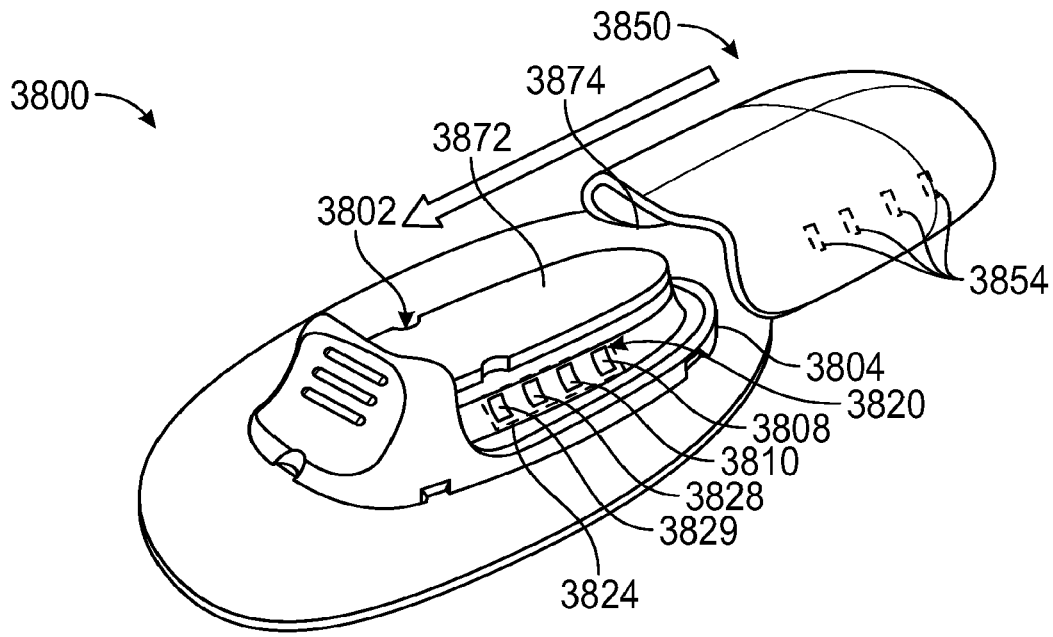
FIG. 38A is a perspective view of an example base and a sensor electronics module configured to be slid over and secured to the base, according to some embodiments.
Figure 38B:
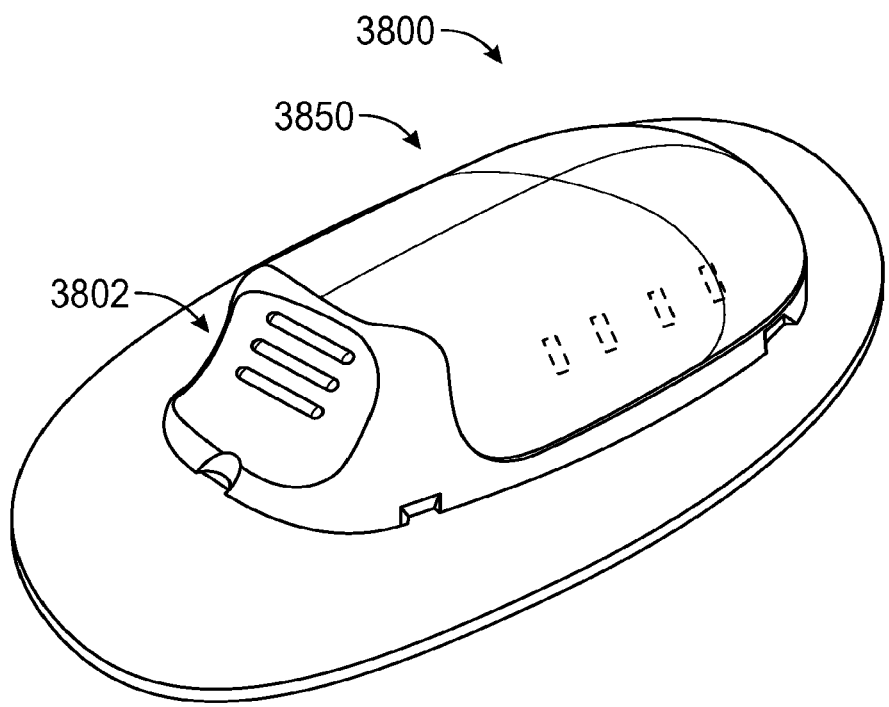
FIG. 38B is a perspective view of the sensor electronics module secured to the base of FIG. 38A.

FIG. 38A is a perspective view of an example base 3802 and a sensor electronics module 3850 configured to be slid over and secured to base 3802, according to some embodiments. FIG. 38B is a perspective view of sensor electronics module 3850 secured to base 3802 of FIG. 38A. Discussion follows with respect to FIGS. 38A-38B below.

As shown in the figures, analyte sensor system 3800 comprises base 3802 and sensor electronics module 3850. Base 3802 can be configured to attach to the skin of the host, for example, utilizing an adhesive pad 3814, which can be disposed on a back surface of base 3802. Adhesive pad 3814 can have substantially similar features and function as previously described for adhesive pad 2314 of FIGS. 23A-23C.

In some embodiments, base 3802 can be configured to slide over and physically and/or mechanically couple with sensor electronics module 3850 utilizing one or more retaining features. For example, base 3802 can have a raised central rail 3872 configured to guide sensor electronics module 3850 into position during physical and/or mechanical coupling to base 3802. In some embodiments, rail 3872 can have a substantially constant width along its length. However, the present disclosure is not so limited and rail 3872 can have a width that tapers along its length such that rail 3872 is substantially wedge-shaped, having a first width at a first end of rail 3872 and a second width smaller than the first width at a second end of rail 3872 opposite the first end. Such a tapered width of rail 3872 may facilitate easy mating of sensor electronics module 3850 with base 3802 and a good seal around one or more components and/or electrical contacts disposed thereon. Sensor electronics module 3850 can further comprise a channel 3874 having a shape that compliments an outer perimeter or shape of rail 3872 of base 3802.

While not shown in FIGS. 38A-38B, to accomplish, affect and/or support such physical and/or mechanical coupling, base 3802 can further include at least one of a first and a second retaining member (e.g., see at least retaining members 3944 of FIG. 39A-39C), while sensor electronics module 3850 can further include at least one of a first and a second retention feature (e.g., see at least retention features 3956 of FIG. 39A-39C) configured to mate with the first and second retaining members, respectively. Such at least one retaining member(s) and retention feature(s) can prevent sensor electronics module 3850 from undesirably backing out from the secured position with respect to base 3802, as shown in FIG. 38, and as further described in connection with FIGS. 39A-39C below.

FIG. 38A illustrates base 3802 as having a first sensor contact 3808 and a second sensor contact 3810, each electrically coupled to a respective terminal of the analyte sensor, and a first battery contact 3828 and a second battery contact 3829, each electrically coupled to a respective terminal of a battery (not shown in FIGS. 38A-38B but see e.g., battery 3918 of FIGS. 39A-39C).

Sensor electronics module 3850 can comprise a plurality of contacts 3854 disposed on an inner surface of channel 3874. In some embodiments, contacts 3854 can include a first signal contact configured to make electrical contact with first sensor contact 3808, a second signal contact configured to make electrical contact with second sensor contact 3810, a first power contact configured to make electrical contact with first battery contact 3828 and a second power contact configured to make electrical contact with second battery contact 3829. Such first and second power contacts can be configured to receive power from the battery, while such first and second signal contacts can be configured to receive the sensor signal from the analyte sensor.

Base 3802 can further include a first sealing member 3824 configured to surround and seal first and second sensor contacts 3808, 3810, first and second battery contacts 3828, 3829, the first and second signal contacts and the first and second power contacts within a first cavity 3820. While first sealing member 3824 is illustrated as being disposed on a sidewall of rail 3874, the present disclosure is not so limited and first sealing member 3824 could alternatively be disposed on an inner surface of channel 3874 of sensor electronics module 3850, surrounding contacts 3854, and similarly configured to form first cavity 3820.

Sensor electronics module 3850 can be secured to base 3802 by aligning channel 3874 of sensor electronics module 3850 with rail 3872 of base 3802 and sliding sensor electronics module 3850 in a direction parallel to the host's body until sensor electronics module 3850 reaches the end of its travel along rail 3872, is seated against at least a portion of base 3802, and the at least one retaining member(s) and retention feature(s) (not shown in FIGS. 38A-38B) are engaged with one another. In some embodiments, such aligning and securing of sensor electronics module 3850 to base 3802 can be accomplished by the host with a single hand, having at least one finger against base 3802 and at least one other finger against sensor electronics module 3850 and pressing the fingers closer to one another until sensor electronics module 3850 is properly secured to base 3802.

An embodiment similar to that described in connection with FIGS. 38A-38B is shown in FIGS. 39A-39C and described below. FIG. 39A is a perspective view of an example base 3902 and a sensor electronics module 3950 configured to be slid over and secured to base 3902, according to some embodiments. FIG. 39B is another perspective view of base 3902 of FIG. 39A. FIG. 39C is an exploded perspective bottom view of base 3902 and sensor electronics module 3950 of FIG. 39A. Discussion follows with respect to FIGS. 39A-39C below.

As shown in the figures, analyte sensor system 3900 comprises base 3902 and sensor electronics module 3950. Base 3902 is configured to receive a battery 3918 within a cavity in a bottom surface of base 3902. Base 3902 can also include a cover 3960 configured to be attached to and/or disposed on a bottom side of base 3902. Cover 3960 may be shaped and sized to secure battery 3918 within base 3902. Cover 3960 can be secured to the bottom surface of base 3902 utilizing any suitable method, for example, snaps, adhesive, friction fittings, heat-staking, and/or laser, heat or ultra-sonic welding along weld line 3912.

As shown in FIG. 39B, base 3902 can comprise a plurality of conductive traces 3966, which can be formed utilizing any suitable process, for example, laser direct structuring (LDS) of base 3902 or overmolding of a conductive elastomer. Conductive traces 3966 may be utilized to ultimately route electrical signals from the analyte sensor to sensor electronics module 3950 and/or power from battery 3918 to sensor electronics module 3950 and to the analyte sensor.

Base 3902 further includes a first sensor contact 3908 and a second sensor contact 3910, each electrically coupled to a respective terminal of the analyte sensor in base 3902 via at least some of conductive traces 3966. Contacts 3908, 3910 can be disposed immediately adjacent to one another. Base 3902 further includes a first battery contact 3928 and a second battery contact 3929, each electrically coupled to a respective terminal of battery 3918 via at least some other of conductive traces 3966 on cover 3960. Contacts 3928, 3929 can be similarly disposed immediately adjacent to one another. Contacts 3908, 3910, 3928, 3929 are illustrated as being disposed on a sidewall of base 3902 and configured to face a mating surface of sensor electronics module 3950. However, the present disclosure is not so-limited and contacts 3908, 3910, 3928, 3929 can be disposed on any suitable surface of base 3902. Contacts 3908, 3910, 3938, 3929 can comprise conductive elastomeric contacts (e.g. pucks), springs, tabs, posts, pogo pins, flat conductive pads or traces, or any other suitable conductive materials and/or structures.

Base 3902 further includes a sealing member 3924, which can extend over and thereby seal conductive traces 3966 and which also surrounds and creates a single continuous seal around contacts 3908, 3910 to form a first cavity 3920a, and another single continuous seal around contacts 3928, 3929 on base 2302 to form a second cavity 3920b. Sealing member 3924 can, for example, include an overmolded component such as an overmolded gasket, an overmolded elastomeric feature, and/or an ultra-violet curable silicone that may be coupled to a surface of base 3902 utilizing any suitable method.

Sensor electronics module 3950 can comprise a plurality of contacts 3954 disposed on a surface (e.g., a sidewall) of sensor electronics module 3950 configured to face the mating surface of sensor electronics module 3950 on which contacts 3908, 3910, 3928, 3929 are disposed. Contacts 3954 can comprise conductive elastomeric contacts (e.g. pucks), springs, tabs, posts, pogo pins, flat conductive pads or traces, or any other suitable conductive materials and/or structures. In some embodiments, contacts 3954 can include a first signal contact configured to make electrical contact with first sensor contact 3908, a second signal contact configured to make electrical contact with second sensor contact 3910, a first power contact configured to make electrical contact with first battery contact 3928 and a second power contact configured to make electrical contact with second battery contact 3929. Such first and second power contacts can be configured to receive power from battery 3918, while such first and second signal contacts can be configured to receive the sensor signal from the analyte sensor.

In some embodiments, base 3902 can be configured to slide over and physically and/or mechanically couple with sensor electronics module 3950 utilizing one or more retaining features. For example, base 3902 can have a raised central rail 3972 configured to guide sensor electronics module 3950 into position during physical and/or mechanical coupling to base 3902. In some embodiments, rail 3972 can have a substantially constant width along its length. However, the present disclosure is not so limited and rail 3972 can have any suitable shape, width or widths along its length. To accomplish, affect and/or support such physical and/or mechanical coupling, base 3902 can further include at least one retaining member 3944. Retaining member(s) 3944 can comprise snaps, hooks, deflectable tabs or any other suitable type of retaining member(s).

Sensor electronics module 3950 can further comprise a channel 3974 having a shape that compliments an outer perimeter or shape of rail 3972 of base 3902, and at least one retention feature 3956 configured to mate with retaining member(s) 3944. In some embodiments, retention feature(s) 3956 can comprise recesses configured to accept retaining member(s) 3944. Such retaining member(s) 3944 and retention feature(s) 3956 can substantially immobilize sensor electronics module 3950 to base 3902 and prevent sensor electronics module 3950 from undesirably backing out from such a secured position.

In some embodiments, base 3902 can have a break line 3964 defining a first portion of base 3902, on which retaining member(s) 3944 are disposed, from a second portion of base 3902 disposed on an opposite side of break line 3964 from the first portion. Accordingly, the first portion of base 3902 can comprise a frangible tab configured to separate from the second portion of base 3902 along break line 3964 when the first portion of base 3902 is sufficiently bent, flexed or otherwise deflected from its resting position shown in FIG. 39A, and similar to that previously described in connection with FIGS. 24A-24D.

Sensor electronics module 3950 can be secured to base 3902 by aligning channel 3974 of sensor electronics module 3950 with rail 3972 of base 3902 and sliding sensor electronics module 3950 in a direction parallel to the host's body until sensor electronics module 3950 reaches the end of its travel along rail 3972, is seated against at least a portion of base 3902, and retaining member(s) 3944 and retention feature(s) 3956 are engaged with one another. In some embodiments, such aligning and securing of sensor electronics module 3950 to base 3902 can be accomplished by the host with a single hand, having at least one finger against base 3902 and at least one other finger against sensor electronics module 3950 and pressing the fingers closer to one another until sensor electronics module 3950 is properly secured to base 3902.

Methods of Manufacture Related to the Above-Described Embodiments

Figure 40:
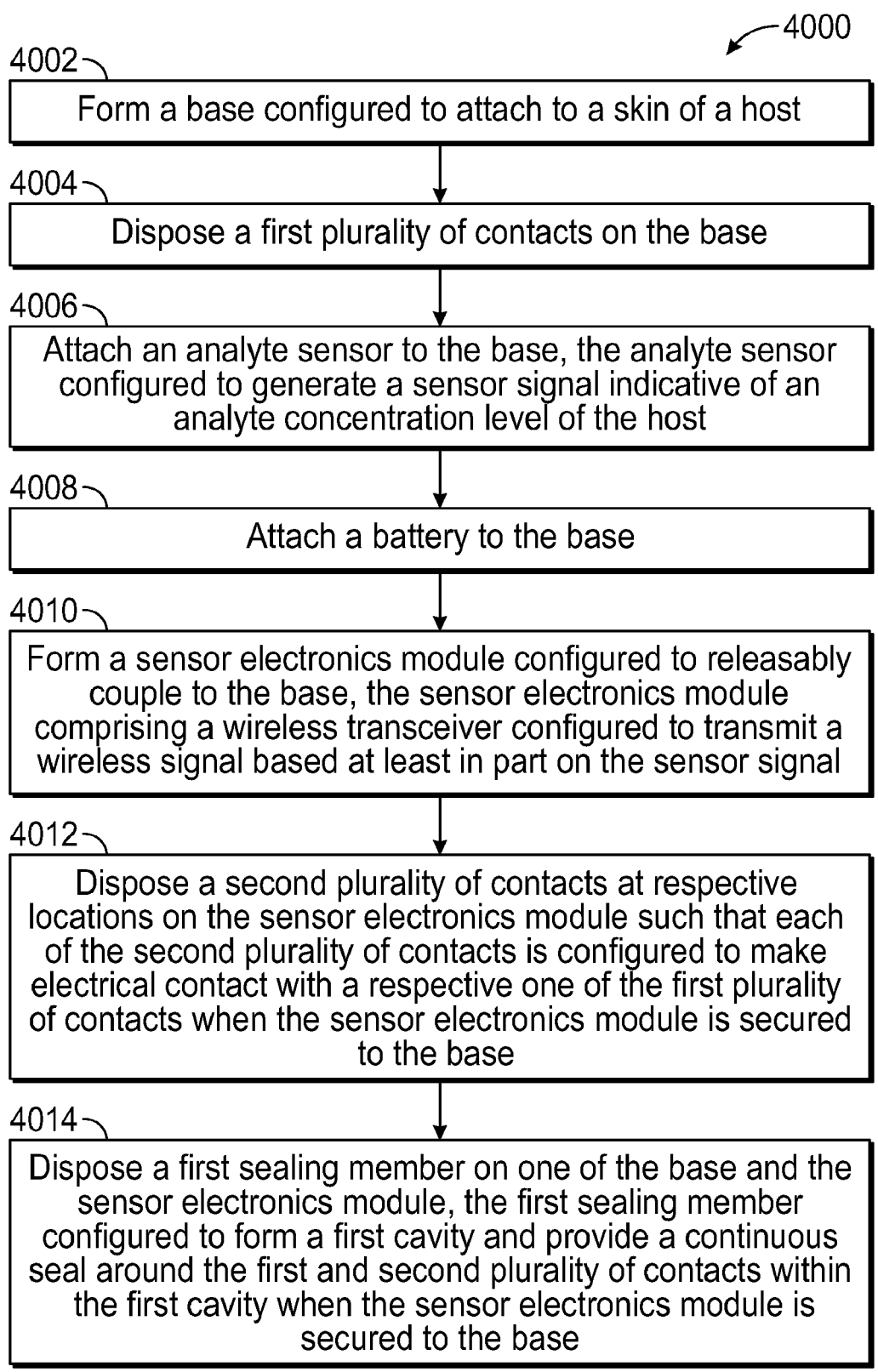
FIG. 40 is a flowchart for a method for fabricating and/or manufacturing an analyte sensor system, according to some embodiments.

Several example methods of fabricating disposable analyte sensor bases having one or more batteries disposed therein and reusable sensor electronics modules configure to releasably couple to the bases are provided below in connection with FIG. 40.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

An example method 4000 for fabricating an analyte sensing apparatus and/or system will now be described in connection with FIG. 40 below. Method 4000 may correspond at least to the previous description in connection with FIGS. 1-39C.

Block 4002 includes forming a base configured to attach to a skin of a host. For example, a base can be formed according to the description related to at least any of bases 1002-3902 as previously described in connection with any of FIGS. 10A-39C.

Block 4004 includes disposing a first plurality of contacts on the base. For example, any of bases 2302-3902 can have disposed thereon at least a first plurality of contacts including first sensor contact 2308-3908 and second sensor contact 2310-3910, as previously described in connection with FIGS. 23A-39C. In some embodiments, the first plurality of contacts can further include first battery contact 2328-3228, 3428-3828 and second battery contact 2329-3229, 3429-3829, as previously described in connection with FIGS. 23A-32 and 34-38B.

Block 4006 includes attaching an analyte sensor to the base, the analyte sensor configured to generate a sensor signal indicative of an analyte concentration level of the host. For example, analyte sensor 104 can be attached to any of at least bases 2302-3902. As previously described, analyte sensor 104 is configured to generate a sensor signal indicative of an analyte concentration level of the host.

Block 4008 includes attaching a battery to the base. For example, a battery, such as any battery described in connection with at least FIGS. 10A-39C, can be attached to the respective base 1002-3902, as previously described in connection with at least FIGS. 10A-39C.

Block 4010 includes forming a sensor electronics module configured to releasably couple to the base, the sensor electronics module comprising a wireless transceiver configured to transmit a wireless signal based at least in part on the sensor signal. For example, a sensor electronics module can be formed according to the description related to at least any of sensor electronics modules 2350-3950 as previously described in connection with any of FIGS. 23A-39C.

Block 4012 includes disposing a second plurality of contacts at respective locations on the sensor electronics module such that each of the second plurality of contacts is configured to make electrical contact with a respective one of the first plurality of contacts when the sensor electronics module is secured to the base. For example, any of sensor electronics modules 2350-3950 can have disposed thereon at least a second plurality of contacts 2354-3954, including a first signal contact configured to make electrical contact with first sensor contact 2308-3908 and a second signal contact configured to make electrical contact with the second sensor contact 2310-3910 when sensor electronics module 2350-3950 is secured to base 2302-3902, as previously described in connection with FIGS. 23A-39C. In some embodiments, the second plurality of contacts 2354-3954 can further include a first power contact configured to make electrical contact with first battery contact 2328-3228, 3428-3828 and a second power contact configured to make electrical contact with second battery contact 2329-3229, 3429-3829 when sensor electronics module 2350-3950 is secured to base 2302-3902, as previously described in connection with FIGS. 23A-32 and 34-38B.

Block 4014 includes disposing a first sealing member on one of the base and the sensor electronics module, the first sealing member configured to form a first cavity and provide a continuous seal around the first and second plurality of contacts within the first cavity when the sensor electronics module is secured to the base. For example, first sealing member 2324-3924 can be disposed on at least one of base 2302-3902 and sensor electronics module 2350-3950, as previously described in connection with at least FIGS. 23A-39C, such that first sealing member 2324-3924 is configured to form a first cavity 2320-3920 and provide a continuous seal around the first and second plurality of contacts within first cavity 2320-3920 when sensor electronics module 2350-3950 is secured to base 2302-3902.

In some embodiments, base 2302-3902 is configured to be disposable. In some embodiments, sensor electronics module 2350-3950 is configured to be reusable. In some embodiments, the battery is configured to provide power to analyte sensor 104 and to sensor electronics module 2350-3950. In some embodiments, the first and second signal contacts are configured to receive the sensor signal via first 2308-3908 and second 2310-3910 sensor contacts and the first and second power contacts are configured to receive power from the battery when sensor electronics module 2350-3950 is secured to base 2302-3902. In some embodiments, each of second plurality of contacts 2654 are in direct electrical contact with one of analyte sensor 104 and the battery.

In some embodiments, method 4000 may further comprise electrically coupling first 2308-3908 and second 2310-3910 sensor contacts to respective terminals of analyte sensor 104. In some embodiments, method 400 may further comprise electrically coupling first battery contact 2328-3228, 3428-3828 and second battery contact 2329-3229, 3429-3829 to respective terminals of the battery.

In some embodiments, method 4000 may further comprise forming a first retaining member 2342-3942 and a second retaining member 2344-3944 on base 2302-3902, and forming, on sensor electronics module 2350-3950, a first retention feature 2352-3952 configured to mate with first retaining member 2342-3942 and a second retention feature 3956 configured to mate with the second retaining member 2344-3944 when sensor electronics module 2350-3950 is secured to base 2302-3902, thereby releasably coupling sensor electronics module 2350-3950 to base 2302-3902. In some embodiments, second retaining member 2344-3944 is frangible and configured to be separable from base 2302-3902. In some embodiments, second plurality of contacts 2854-2954 are disposed on first retention feature 2852, 2952. In some embodiments, first retaining member 2842, 2942 comprises a hood and the first plurality of contacts 2908, 2910, 2928, 2929 are disposed within the hood. In some embodiments, first sealing member 2824 is disposed around a circumference of securement feature 2852 such that first cavity 2820 is disposed within the hood. In some embodiments, first sealing member 2924 is disposed on an inner surface of the hood.

In some embodiments, method 4000 may further comprise securing cover 2460, 2560, 2960, 3160, 3360, 3960 to a bottom of base 2402, 2502, 2902, 3160, 3360, 3902. Such a cover can be configured to secure the battery within the respective base. In some embodiments, method 4000 may further comprise disposing a first plurality of conductive traces 2466, 3166, 3366, on cover 2460, 3160, 3360 such that at least some of first plurality of contacts are coupled to one of analyte sensor 104 and the battery via first plurality of conductive traces 2466, 3166, 3366 when cover 2460, 3160, 3360 is secured to the bottom of base 2402, 3102, 3302.

In some embodiments, method 4000 may further comprise disposing a first plurality of conductive traces 2366, 2566-2666, 2866-3066, 3466-3966 on base 2302, 2502-2026, 2802-3002, 3402-3902 such that at least some of the first plurality of contacts are electrically coupled to one of analyte sensor 104 and the battery via first plurality of conductive traces 2366, 2566-2666, 2866-3066, 3466-3966. In some embodiments, first sealing member 2524-2624, 2924, 3824-3924 extends over first plurality of conductive traces 2566-2666, 2966, 3866-3966, thereby sealing first plurality of conductive traces 2566-2666, 2966, 3866-3966 from moisture ingress. In some embodiments, first sealing member 2666 extends over battery 2618, thereby sealing battery 2618 from moisture ingress.

In some embodiments, method 4000 may further comprise forming an aperture 3070-3170, 3670-3770 in sensor electronics module 3050-3150, 3650-3750, and forming a raised portion 3005-3105, 3605-3705 on base 3002-3102, 3602-3702 configured to fit within aperture 3070-3170, 3670-3770, wherein an outer perimeter of the raised portion compliments an inner perimeter of the aperture. In some embodiments, first plurality of contacts 3008, 3010, 3028, 3029 are disposed on raised portion 3005. In some embodiments, aperture 3070-3170 is symmetrical about at least one axis parallel to a top surface of sensor electronics module 3050-3150 and asymmetrical about at least one other axis parallel to the top surface of sensor electronics module 3050-3150. In some embodiments, the battery is disposed within raised portion 3005-3105, 3605 of base 3002-3102, 3602. In some embodiments, a top surface of raised portion 3005-3105, 3605-3705 sits substantially flush with a top surface of sensor electronics module 3050-3150, 3650-3750 when the sensor electronics module is secured to base 3002-3102, 3602-3702.

In some embodiments, method 4000 may include forming a recess 3242-3342 in a top surface of base 3202-3302 and forming a protrusion 3252-3352 configured to mate with recess 3242-3342 such that mating of protrusion 3252-3352 with recess 3242-3342 aligns sensor electronics module 3250-3350 for securing with base 3202-3302.

In some embodiments, method 4000 may further comprise forming a third plurality of contacts on base 3302, 3902, forming a fourth plurality of contacts at locations on sensor electronics module 3350, 3950 such that each of the fourth plurality of contacts is configured to make electrical contact with a respective one of the third plurality of contacts when sensor electronics module 3350, 3950 is secured to base 3302, 3902, and disposing a second sealing member 3325, 3925 on one of base 3302, 3902 and sensor electronics module 3350, 3950. Second sealing member 3325, 3925 is configured to form a second cavity 3320*b*, 3920*b* and provide a continuous seal around the third and fourth plurality of contacts within the second cavity when sensor electronics module 3350, 3950 is secured to base 3302, 3902. In some embodiments, the third plurality of contacts comprises first battery contact 3328, 3928 and second battery contact 3329, 3929. In some embodiments, method 4000 further comprises electrically coupling first 3328, 3928 and second 3329, 3929 battery contacts to respective terminals of the battery. In some embodiments, fourth plurality of contacts 3354, 3954 comprises a first power contact configured to make electrical contact with first battery contact 3328, 3928 and a second power contact configured to make electrical contact with second battery contact 3329, 3929 when sensor electronics module 3350, 3950 is secured to base 3302, 3902.

In some embodiments, second plurality of contacts 3454-3754 comprise concentric, circular contacts. In some embodiments, concentric, circular contacts 3454-3754 are disposed around a center of sensor electronics module 3450-3750. In some embodiments, each of second plurality of contacts 3454-3754 are configured to make electrical contact with the respective one of the first plurality of contacts when sensor electronics module 3450-3750 is secured to base 3402-3702 in any of a plurality of radial orientations.

In some embodiments, method 4000 may further comprise forming an aperture 3470 in base 3402 and forming a raised portion 3405 on sensor electronics module 3450 configured to fit within aperture 3470, wherein an outer perimeter of raised portion 3405 compliments an inner perimeter of aperture 3470. In some embodiments, aperture 3470 and raised portion 3405 each have a substantially circular shape.

In some embodiments, method 4000 may further comprise forming raised rail 3872-3972 on base 3802-3902 and forming channel 3874-3974 having a shape that compliments a shape of raised rail 3872-3972 on sensor electronics module 3850-3950. In some embodiments, raised rail 3872-3972 can have a constant width along its length. In some embodiments, a width of raised rail 3872-3972 tapers along its length. In some embodiments, first plurality of contacts 3808, 3810, 3828, 3829 are disposed on a sidewall of raised rail 3872 and second plurality of contacts 3854 is disposed on a sidewall of channel 3874. In some embodiments, first 3908, 3910 and third 3928, 3929 plurality of contacts are disposed on a sidewall of base 3902 and the second and fourth plurality of contacts 3954 are disposed on a sidewall of sensor electronics module 3950.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An analyte sensor assembly, comprising:
    a base configured to attach to a skin of a host, the base having a bottom side configured to face towards the skin of the host and a top side configured to face opposite the bottom side, the base comprising:
        an analyte sensor configured to generate a sensor signal indicative of an analyte concentration level of the host;
        at least one battery;
        at least one sensor contact;
        at least one battery contact; and
        a cover configured to secure to the bottom side of the base and secure the at least one battery to the base;
    a sensor electronics module configured to releasably couple to the base, the sensor electronics module comprising:
        a facing surface configured to face the top side of the base;
        at least one signal contact configured to make electrical contact with the at least one sensor contact; and
        at least one power contact configured to make electrical contact with the at least one battery contact; and
    a sealing member configured to provide a seal between the facing surface and the base and around at least the at least one battery contact and the at least one power contact when the sensor electronics module is releasably coupled to the base.

2. The assembly of claim 1, wherein the sealing member is further configured to provide the seal around at least the at least one sensor contact.

3. The assembly of claim 1, comprising at least two sensor contacts and at least two battery contacts, wherein the sealing member is configured to provide the seal around the at least two sensor contacts and the at least two battery contacts.

4. The assembly of claim 1, wherein the base further comprises a plurality of conductive traces configured to electrically connect the at least one battery to the at least one battery contact.

5. The assembly of claim 1, wherein the base further comprises a plurality of conductive traces configured to electrically connect the analyte sensor to the at least one sensor contact.

6. The assembly of claim 1, wherein the base is disposable.

7. The assembly of claim 1, wherein the at least one battery is configured to provide power to the analyte sensor and to the sensor electronics module.

8. The assembly of claim 1, wherein the base further comprises
    a first retaining member configured to mate with a securement feature of the sensor electronics module; and
    a second retaining member configured to mate with a retention feature of the sensor electronics module.

9. The assembly of claim 8, wherein the second retaining member is frangible and configured to be separable from the base.

10. The assembly of claim 8, wherein the securement feature comprises a protrusion or a toe, and the first retaining member comprises a recess, a ledge, a hook, or a slit.

11. The assembly of claim 1, wherein the sealing member is an overmolded elastomer.

12. The assembly of claim 1, wherein the sealing member is configured to provide a seal around at least the at least one sensor contact and the at least one signal contact when the sensor electronics module is releasably coupled to the base.

13. The assembly of claim 1, wherein the sealing member is a continuous sealing member.

14. The assembly of claim 1, wherein the sensor electronics module includes a wireless transceiver.

15. The assembly of claim 1, wherein the sensor electronics module is reusable.

16. The assembly of claim 1, wherein the cover is configured to secure to the bottom side of the base by snaps, adhesive, friction fittings, heat-staking, and/or laser, heat or ultra-sonic welding.

* * * * *